United States Patent
Cheng et al.

(10) Patent No.: US 8,609,675 B2
(45) Date of Patent: Dec. 17, 2013

(54) FUSED TRICYCLIC COMPOUNDS AS NOVEL MTOR INHIBITORS

(75) Inventors: Cliff C. Cheng, Cambridge, MA (US); Hongbo Zeng, Westford, MA (US); Gerald W. Shipps, Jr., Stoneham, MA (US); Yongqi Deng, Newton, MA (US); Zhaoyang Meng, Lansdale, PA (US); Lianyun Zhao, Blue Bell, PA (US); Yang Nan, Malden, MA (US); Binyuan Sun, Chestnut Hill, MA (US); Duan Liu, Arlington, MA (US); Panduranga A. Reddy, Walpole, MA (US); M. Arshad Siddiqui, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/379,685

(22) PCT Filed: Jun. 30, 2010

(86) PCT No.: PCT/US2010/040604
§ 371 (c)(1), (2), (4) Date: Mar. 22, 2012

(87) PCT Pub. No.: WO2011/002887
PCT Pub. Date: Jan. 6, 2011

(65) Prior Publication Data
US 2012/0178744 A1  Jul. 12, 2012

Related U.S. Application Data

(60) Provisional application No. 61/222,529, filed on Jul. 2, 2009.

(51) Int. Cl.
*A01N 43/54* (2006.01)
*C07D 491/00* (2006.01)

(52) U.S. Cl.
USPC .......................................... 514/267; 544/250

(58) Field of Classification Search
USPC ................... 514/228.5, 267; 544/251
See application file for complete search history.

(56) References Cited

U.S. PATENT DOCUMENTS

2008/0234262 A1  9/2008 Zask

FOREIGN PATENT DOCUMENTS

WO  2007009773  1/2007

OTHER PUBLICATIONS

Guertin, D.A., et al. "Defining the Role of mTOR in Cancer." Cancer Cell Review. (Jul. 2007), vol. 12, pp. 9-22.*
Bock, C., et al. "Managing drug resistance in cancer: lessons from HIV therapy." Nature. (Jul. 2012), vol. 12, pp. 494-501.*
Mayo Clinic. Available at: < http://www.mayoclinic.com/health/prostate-cancer-prevention/MC00027 >.*
Mayo Clinic. Available at: < http://www.mayoclinic.com/health/bladder-cancer/DS00177/DSECTION=preventon >.*
Mayo Clinic. Available at: < http://www.mayoclinic.com/health/pancreatic-cancer/DS00357 >.*
Elgemeie, G. et al., "Novel Synthesis of Mercaptopurine and Pentaaza-as-Indiance Analogues: Reaction of [Bis(methylthio)methylene]malononitrile and Ethyl 2-Cyano-3,3-bis(methylthio)acrylate with 5-Aminopyrazoles", Bull. Chem. Soc. Jpn., 67(3):738-741 (1994).

* cited by examiner

*Primary Examiner* — Noble Jarrell
*Assistant Examiner* — John S Kenyon
(74) *Attorney, Agent, or Firm* — Li Su; Laura M. Ginkel

(57) ABSTRACT

The present invention provides Fused Tricyclic Compounds of the Formula (I) wherein Q, $R^1$, $R^2$, $R^3$, and $R^4$ are as defined herein, and pharmaceutically acceptable salts of such Fused Tricyclic Compounds. The Fused Tricyclic Compounds are useful in the treatment of cancer and other proliferative disorders.

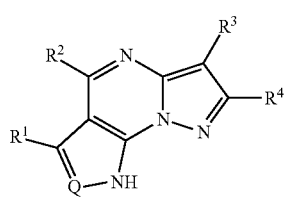

(I)

14 Claims, No Drawings

FUSED TRICYCLIC COMPOUNDS AS NOVEL MTOR INHIBITORS

FIELD OF THE INVENTION

This invention is directed to certain substituted dipyrazolo[1,5-a:4',3'-e]pyrimidines and pyrazolo[1,5-a]pyrrolo[3,2-e]pyrimidines (herein referred to as the "Fused Tricyclic Compounds") as inhibitors of mammalian Target Of Rapamycin (mTOR) kinase, which is also known as FRAP, RAFT, RAPT or SEP. The compounds are useful in the treatment of cancer and other proliferative disorders.

BACKGROUND OF THE INVENTION

The mammalian target of rapamycin (mTOR) is a central regulator of cell growth and proliferation and plays a gatekeeper role in the control of cell cycle progression. The mTOR signaling pathway, which integrates both extracellular and intracellular signals, is activated in certain cellular processes such as tumor formation, angiogenesis, insulin resistance, adipogenesis, and T-lymphocyte activation. In addition, the mTOR signaling pathway is deregulated in diseases such as cancer and type 2 diabetes. See Laplante et al., *J. Cell Science* 122, pp 3589-3593 (2009).

mTOR mediates mitogenic signals from PI3K/AKT through to the downstream targets S6K1 (ribosomal S6 kinase 1), 4E-BP1 (eukaryotic translation initiation factor 4E-binding protein) and AKT. Recently, it has been shown that mTOR exists in two complexes. Raptor-mTOR complex (mTORC1) is a rapamycin-sensitive complex that phosphorylates S6K1 and 4E-BP1. Rictor-mTOR complex (mTORC2) is a rapamycin-insensitive complex that phosphorylates AKT at Ser473. Although the precise mechanism by which rapamycin inhibits mTOR function is not well understood, rapamycin partially inhibits mTOR function through mTORC1. Since mTORC2 is involved in the regulation of cell survival, metabolism, proliferation, and cytoskeletal organization in a rapamycin-independent manner, complete inhibition of mTOR function through inhibition of both mTORC1 and mTORC2 may lead to a broader spectrum antitumor activity in the treatment of cancer or better efficacy. In addition, inhibition of both mTORC1 and mTORC2 may lead to better efficacy in treating other diseases than through inhibition of mTORC1 alone.

There exists a need in the art for small-molecule compounds having desirable physicochemical properties that are useful for treating cancer and other disorders associated with deregulated mTOR activity. Specifically, there exists a need for small molecule inhibitors of mTOR kinase that block signaling through mTORC1 and mTORC2 for treating cancer and other disorders.

SUMMARY OF THE INVENTION

In one aspect, the present invention provides compounds of Formula (I) (herein referred to as the "Fused Tricyclic Compounds"):

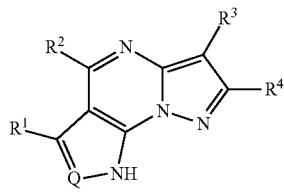

and pharmaceutically acceptable salts thereof, wherein

Q is N or C(H);

$R^1$ is H, halo, $-NR^5R^6$, $-OR^7$, $-SR^8$, $-CN$, alkyl, alkenyl, alkynyl, haloalkyl, cycloalkyl, aryl, heteroaryl, heterocyclyl, cycloalkylalkyl, arylalkyl, heteroarylalkyl, or heterocyclylalkyl, wherein said cycloalkyl, aryl, heteroaryl, heterocyclyl, cycloalkylalkyl, arylalkyl, heteroarylalkyl, or heterocyclylalkyl of $R^1$ is unsubstituted or substituted with one more moieties, which can be the same or different, each moiety being selected from the group consisting of halogen, alkyl, cycloalkyl, $-CF_3$, $-CN$, $-C(O)OH$, $-(CH_2)_x-C(O)OH$, $-OCF_3$, $-OR^2$, $-C(O)R^{10}$, $-NR^5R^6$, $-C(O_2)$-alkyl, $-C(O)NR^5R^6$, $-SR^8$, and $-S(O_2)R^7$;

$R^2$ is selected from the group consisting of heterocyclyl, spiroheterocyclyl, heterocyclenyl, cycloalkyl, cycloalkenyl, heteroaryl, aryl, heterocyclylalkyl, spiroheterocyclylalkyl, heterocyclenylalkyl, cycloalkylalkyl, cycloalkenylalkyl, heteroarylalkyl, arylalkyl, $-O$-heterocyclyl, $-S$-heterocyclyl, $-S(O)$-heterocyclyl, $-S(O)_2$-heterocyclyl, $-N(R^9)$-heterocyclyl, and -alkyl-$N(R^9)$-heterocyclyl, wherein said heterocyclyl, spiroheterocyclyl, heterocyclenyl, cycloalkyl, cycloalkenyl, heteroaryl, aryl, heterocyclylalkyl, spiroheterocyclylalkyl, heterocyclenylalkyl, cycloalkylalkyl, cycloalkenylalkyl, heteroarylalkyl, arylalkyl, $-O$-heterocyclyl, $-S$-heterocyclyl, $-S(O)$-heterocyclyl, $-S(O)_2$-heterocyclyl, $-N(R^9)$-heterocyclyl, or -alkyl-$N(R^9)$-heterocyclyl is unsubstituted or substituted with one to four moieties, which can be the same or different, each moiety being selected from group X;

X is alkyl, halo, $-CN$, $-NR^5R^6$, $SR^8$, $-OR^7$, $-C(O)$alkyl, -trihaloalkyl, -dihaloalkyl, -monohaloalkyl, $-C(O)_2$alkyl, $-C(O)_2H$, hydroxyalkyl, $-S(O)_2R^8$, hydroxyl, -alkyl-$C(O)_2H$, -alkyl($CO$)$N(CH_3)$—$O$—$CH_3$, $-C(O)_2$-alkyl, -alkyl-$C(O)$—$NH_2$, -alkyl-$CN$, $-C(O)$—$NR^5R^6$, -alkyl-$C(O)_2$alkyl, $-C(O)$-hydroxyalkyl, $-C(O)$-alkyl-$O$-alkyl, -alkyl($CO$)$N(H)$—$S(O)_2$-cycloalkyl, -alkyl($CO$)$N(H)$—$S(O)_2$—$CF_3$, -alkyl($CO$)$N(H)$—$S(O)_2$-alkyl, -alkyl-$C(O)$—$N($alkyl$)_2$, -alkyl-$N(H)$—$S(O)_2$-alkyl, -alkyl($CO$)$N(H)$—$S(O)_2$-cycloalkyl, $-C(O)$—$CO_2H$, $-C(O)$—$CH(OH)$—$CH_3$, $-C(O)CH(OH)CH_2OH$, $-C(O)_2$-alkyl-aryl, $-SO_2$—$CF_3$, or $-C(O)H$, or X is cycloalkyl, heterocyclyl, aryl, heteroaryl, heteroarylalkyl, $-NH$-heterocyclyl, $-C(O)$-heteroaryl, wherein each of said cycloalkyl, heterocyclyl, aryl, heteroaryl, heteroarylalkyl, $-NH$-heterocyclyl, $-C(O)$-heteroaryl of X is unsubstituted or substituted with one or more moieties, which can be the same or different, each moiety being selected from the group consisting of halogen, alkyl, cycloalkyl, $-CF_3$, $-CN$, $-C(O)OH$, $-SO_3H$, $-P(O)(OH)_2$, $-(CH_2)_x-C(O)OH$, $-OCF_3$, $-OR^7$, $-C(O)R^{10}$, $-NR^5R^6$, $-C(O_2)$-alkyl, $-C(O)NR^5R^6$, $-SR^8$, and $-S(O_2)R^7$;

R³ is H, halogen, alkenyl, alkynyl, —CF₃, —C(O)R¹⁰, aryl, cycloalkyl, cycloalkenyl, heteroaryl, heterocyclyl, heterocycloalkenyl, arylalkyl, cycloalkylalkyl, cycloalkenylalkyl, heteroarylalkyl, heterocyclylalkyl, heterocycloalkenylalkyl, wherein each of said aryl, cycloalkyl, cycloalkenyl, heteroaryl, heterocyclyl, heterocycloalkenyl, arylalkyl, cycloalkylalkyl, cycloalkenylalkyl, heteroarylalkyl, heterocyclylalkyl, heterocycloalkenylalkyl of R³ is unsubstituted or substituted with one or more moieties which can be the same or different, each moiety being selected from the group consisting of Y, halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷;

Y is aryl, cycloalkyl, cycloalkenyl, heteroaryl, heterocyclyl, or heterocycloalkenyl, wherein each of said cycloalkyl, cycloalkenyl, heteroaryl, heterocyclyl, or heterocycloalkenyl of Y is unsubstituted or substituted with one more moieties, which can be the same or different, each moiety being selected from the group consisting of halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷;

R⁴ is H, halo, —NR⁵R⁶, —OR⁷, —OR⁸, —SR⁹, —CN, alkyl, alkenyl, alkynyl, haloalkyl, cycloalkyl, aryl, heteroaryl, heterocyclyl, cycloalkylalkyl, arylalkyl, heteroarylalkyl, or heterocyclylalkyl;

each occurrence of R⁵ is independently H, alkyl, cycloalkyl, aryl, heteroaryl, or heterocyclyl;

each occurrence of R⁶ is independently H, alkyl, cycloalkyl, aryl, heteroaryl, or heterocyclyl, or R⁵ and R⁶ together with the nitrogen atom to which they are attached form a heterocyclyl ring;

each occurrence of R⁷ is independently H, alkyl, cycloalkyl, aryl, heteroaryl, or heterocyclyl;

each occurrence of R⁸ is independently H, alkyl, cycloalkyl, aryl, heteroaryl, or heterocyclyl;

each occurrence of R⁹ is independently H or alkyl;

R¹⁰ is alkyl, cycloalkyl, or aryl; and x is an integer from 1 to 4.

In another aspect, the invention provides a pharmaceutical composition comprising a Fused Tricyclic Compound, or a pharmaceutically acceptable salt thereof, and at least one pharmaceutically acceptable carrier.

In yet another aspect, the invention provides a method of treating a cancer, comprising administering a therapeutically effective amount of a Fused Tricyclic Compound or a pharmaceutically acceptable salt thereof to a patient, e.g., a human patient, in need thereof.

In still another aspect, the invention provides use of a Fused Tricyclic Compound or a pharmaceutically acceptable salt thereof for treating cancer.

In yet another aspect, the invention provides a method of treating a cancer, comprising administering an amount of a Fused Tricyclic Compound or a pharmaceutically acceptable salt thereof, and an amount of one or more of additional anticancer drugs to a patient in need thereof.

In still another aspect, the invention provides use of a Fused Tricyclic Compound or a pharmaceutically acceptable salt thereof and one or more of additional anticancer drugs for treating cancer.

In another aspect, the invention provides a method of treating a disease or disorder associated with dysregulated mTOR activity, comprising administering a therapeutically effective amount of a Fused Tricyclic Compound or a pharmaceutically acceptable salt thereof to a patient, e.g., a human patient, in need thereof.

DETAILED DESCRIPTION OF THE INVENTION

The present invention provides Fused Tricyclic Compounds, pharmaceutical compositions comprising at least one Fused Tricyclic Compound, and methods of using the Fused Tricyclic Compounds for treating cancer in a patient. In addition, the present invention provides methods of using the Fused Tricyclic Compounds for treating a disease or disorder associated with dysregulated mTOR activity in a patient.

DEFINITIONS AND ABBREVIATIONS

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)₂, —O—C(O)-alkyl, —O—C(O)-aryl, —O—C(O)-cycloalkyl, —SF₅, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_7$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

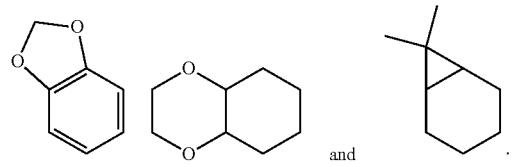

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such moiety is pyrrolidone:

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such moiety is pyrrolidinone:

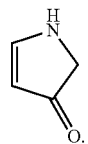

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

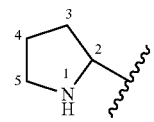

there is no —OH attached directly to carbons marked 2 and 5.

It should also be noted that tautomeric forms such as, for example, the moieties:

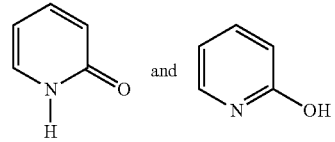 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g., from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. And any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Green's Protective Groups in Organic Synthesis* 4$^{th}$ Ed. (2007), Wiley, New York.

When any variable (e.g., aryl, heterocycle, $R^5$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1975) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as achiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For example, those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts of the compounds of Formula I, are intended to be included in the present invention.

The present invention further includes the compounds of Formula (I) in all their isolated forms. For example, the above-identified compounds are intended to encompass all forms of the compounds such as, any solvates, hydrates, stereoisomers, and tautomers thereof.

Compounds of Formula (I)

The present invention provides Fused Tricyclic Compounds having the Formula (I):

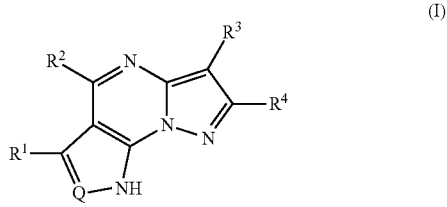

(I)

wherein Q, X, Y, $R^1$, $R^2$, $R^3$, $R^4$, $R^5$, $R^6$, $R^7$, $R^8$, $R^9$, $R^{10}$, and x are as defined above for the compound of Formula (I).

In one embodiment of the compound of Formula (I), $R^3$ is aryl, cycloalkyl, cycloalkenyl, heteroaryl, heterocyclyl, heterocycloalkenyl, wherein each of said aryl, cycloalkyl, cycloalkenyl, heteroaryl, heterocyclyl, or heterocycloalkenyl of $R^3$ is unsubstituted or substituted with one or more moieties which can be the same or different, each moiety being selected from the group consisting of Y, halogen, alkyl, cycloalkyl, —CF$_3$, —CN, —C(O)OH, —(CH$_2$)$_x$—C(O)OH, OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (I), $R^3$ is aryl or heteroaryl, wherein said aryl or heteroaryl of $R^3$ is unsubstituted or substituted with one or more moieties which can be the same or different, each moiety being selected from the group consisting of Y, halogen, alkyl, cycloalkyl, —CF$_3$, —CN, —C(O)OH, —(CH$_2$), —C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (I), R$^3$ is aryl or heteroaryl, wherein said aryl or heteroaryl of R$^3$ is unsubstituted or substituted with one or more Y groups.

In another embodiment of the compound of Formula (I), R$^3$ is aryl or heteroaryl, wherein the aryl or heteroaryl of R$^3$ is substituted with one Y group. In a specific embodiment, the Y group is aryl or heteroaryl, wherein said aryl or heteroaryl of Y is unsubstituted or substituted with one more moieties, which can be the same or different, each moiety being selected from the group consisting of halogen, alkyl, cycloalkyl, —CF$_3$, —CN, —C(O)OH, —(CH$_2$), —C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (I), R$^3$ is pyridyl, quinolinyl, or pyrazolyl, wherein said pyridyl, quinolinyl, or pyrazolyl is unsubstituted or substituted with one or more moieties which can be the same or different, each moiety being selected from the group consisting of Y, halogen, alkyl, cycloalkyl, —CF$_3$, —CN, —C(O)OH, —(CH$_2$)$_x$—C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (I), R$^3$ is quinolinyl, wherein said quinolinyl is unsubstituted or substituted with one or more halogen.

In another embodiment of the compound of Formula (I), R$^3$ is pyridyl substituted with one Y group, wherein said Y group is aryl or heteroaryl, wherein said aryl or heteroaryl of Y is unsubstituted or substituted with one or more alkyl.

In another embodiment of the compound of Formula (I), R$^3$ is pyrazolyl substituted with one Y group, wherein said Y group is aryl or heteroaryl, wherein said aryl or heteroaryl of Y is unsubstituted or substituted with one or more alkyl.

In another embodiment of the compound of Formula (I), R$^2$ is heterocyclyl, heterocyclenyl, cycloalkyl, cycloalkenyl, heterocyclylalkyl, heterocyclenylalkyl, cycloalkylalkyl, cycloalkenylalkyl, —O-heterocyclyl, —S-heterocyclyl, —S(O)-heterocyclyl, —S(O)$_2$-heterocyclyl, —N(R$^9$)-heterocyclyl, or —alkyl-N(R$^9$)-heterocyclyl, wherein said heterocyclyl, cycloalkyl, cycloalkenyl, heterocyclylalkyl, cycloalkylalkyl, cycloalkenylalkyl, —O-heterocyclyl, —S-heterocyclyl, —S(O)-heterocyclyl, -5(O)$_2$-heterocyclyl, —N(R$^9$)-heterocyclyl or —alkyl-N(R$^9$)-heterocyclyl of R$^2$ is unsubstituted or substituted with one to four moieties, which can be the same or different, each moiety being selected from the group X. For example, in particular instances of this embodiment, X can be alkyl, halo, —CN, —NR$^5$R$^6$, —SR$^8$, —OR$^7$, —C(O)alkyl, -trihaloalkyl, -dihaloalkyl, -monohaloalkyl, —C(O)$_2$alkyl, —C(O)$_2$H, hydroxyalkyl, —S(O)$_2$R$^8$, -alkyl-C(O)$_2$H, —C(O)—CH(OH)—CH$_3$, or —C(O)—CH(OH)—CH$_2$OH.

In another embodiment of the compound of Formula (I), R$^2$ is heterocyclyl, cycloalkyl, cycloalkenyl, heterocyclylalkyl, cycloalkylalkyl, —O-heterocyclyl, or —alkyl-N(H)-heterocyclyl, wherein said heterocyclyl, heterocyclylalkyl, —O-heterocyclyl, or —alkyl-N(H)-herocyclyl of R$^2$ is unsubstituted or substituted with one to four moieties, which can be the same or different, each moiety being selected from the group consisting of alkyl, —C(O)$_2$H, —S(O)$_2$CH$_3$, —CH$_2$C(O)$_2$H, —C(O)—CH(OH)—CH$_3$, and —C(O)—CH(OH)—CH$_2$OH.

In another embodiment of the compound of Formula (I), R$^2$ is 1,1-dioxo-tetrahydrothiopyranyl, cyclohexyl, cyclohexylmethyl, 1,1-dioxo-thiomorpholinyl, piperidinyl, piperidinylmethyl, piperidinyloxy, pyrrolidinyl, or cyclohexenyl.

In another embodiment of the compound of Formula (I), R$^1$ is H or alkyl.

In another embodiment of the compound of Formula (I), R$^4$ is H.

In another embodiment of the compound of Formula (I), Q is N.

In another embodiment of the compound of Formula (I), Q is C(H).

In one embodiment, one or more hydrogen atoms of a compound of Formula (I) is replaced with a deuterium atom.

In another embodiment, a compound of Formula (I) is in purified form.

In another aspect, the invention provides a compound of the Formula (Ia):

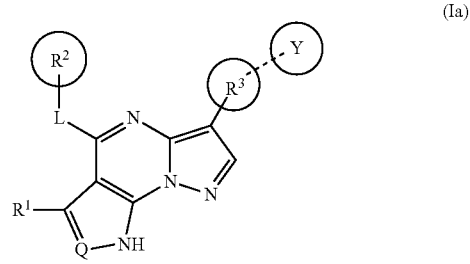

(Ia)

or a pharmaceutically acceptable salt thereof, wherein

Q is N or C(H);

L is —CH$_2$—, —CH$_2$—CH$_2$—, —CH$_2$—CH$_2$—CH$_2$—CH$_2$—, —NH—CH$_2$—, or —O—, or L is absent such that R$^2$ is bonded directly to the illustrated pyrimidine ring;

R$^1$ is H, halo, or alkyl;

R$^2$ is heterocyclyl, heterocyclenyl, cycloalkyl, or cycloalkenyl, wherein said heterocyclyl, heterocyclenyl, cycloalkyl, or cycloalkenyl of R$^2$ is unsubstituted or substituted with one to four moieties, which can be the same or different, each moiety being selected from the group X;

X is alkyl, halo, —CN, —NR$^5$R$^6$, SR$^8$, —OR$^7$, —C(O) alkyl, -trihaloalkyl, -dihaloalkyl, -monohaloalkyl, —C(O)$_2$alkyl, —C(O)$_2$H, hydroxyalkyl, —S(O)$_2$R$^8$, -alkyl-C(O)$_2$H, —C(O)—CH(OH)—CH$_3$, or —C(O)—CH(OH)—CH$_2$OH;

R$^3$ is aryl, cycloalkyl, cycloalkenyl, heteroaryl, heterocyclyl, heterocycloalkenyl, wherein each of said aryl, cycloalkyl, cycloalkenyl, heteroaryl, heterocyclyl, or heterocycloalkenyl of R$^3$ is unsubstituted or substituted with one or more moieties which can be the same or different, each moiety being selected from the group consisting of halogen, alkyl, cycloalkyl, CF$_3$, CN, —C(O)OH, (CH$_2$), —C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, —S(O$_2$)R$^7$; and Y is present or absent, wherein Y, if present, is aryl or heteroaryl, wherein said aryl or heteroaryl of Y is unsubstituted or substituted with one more moieties, which can be the same or different, each moiety being selected from the group consisting of halogen, alkyl, cycloalkyl, —CF$_3$, CN, —C(O) OH, —(CH$_2$)$_c$—C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$;

each occurrence of R$^5$ is independently H, alkyl, cycloalkyl, aryl, heteroaryl, or heterocyclyl;

each occurrence of R$^6$ is independently H, alkyl, cycloalkyl, aryl, heteroaryl, or heterocyclyl, or R$^5$ and R$^6$ together with the nitrogen atom to which they are attached form a heterocyclyl ring;

each occurrence of $R^7$ is independently H, alkyl, cycloalkyl, aryl, heteroaryl, or heterocyclyl;

each occurrence of $R^8$ is independently H, alkyl, cycloalkyl, aryl, heteroaryl, or heterocyclyl; each occurrence of $R^9$ is independently H or alkyl;

$R^{10}$ is alkyl, cycloalkyl, or aryl; and x is an integer from 1 to 4.

In some embodiments of the compound of Formula (Ia), $R^2$ is heterocyclyl, cycloalkyl, or cycloalkenyl, wherein said heterocyclyl, cycloalkyl, or cycloalkenyl of $R^2$ is unsubstituted or substituted with one to four moieties, which can be the same or different, each moiety being alkyl, —C(O)$_2$H, —S(O)$_2$CH$_3$, —CH$_2$C(O)$_2$H, —C(O)—CH(OH)—CH$_3$, or —C(O)—CH(OH)—CH$_2$OH.

In another embodiment of the compound of Formula (Ia), $R^2$ is 1,1-dioxo-tetrahydrothiopyranyl, cyclohexyl, 1,1-dioxo-thiomorpholinyl, piperidinyl, pyrrolidinyl or cyclohexenyl.

In another embodiment of the compound of Formula (Ia), $R^3$ is aryl or heteroaryl, wherein said aryl or heteroaryl of $R^3$ is unsubstituted or substituted with one or more moieties which can be the same or different, each moiety being selected from the group consisting of Y, halogen, alkyl, cycloalkyl, —CF$_3$, —CN, —C(O)OH, —(CH$_2$), —C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (Ia), $R^3$ is aryl or heteroaryl, wherein said aryl or heteroaryl of $R^3$ is substituted with one Y group. In specific instances of this embodiment, the Y group is aryl or heteroaryl, wherein said aryl or heteroaryl of Y is unsubstituted or substituted with one more moieties, which can be the same or different, each moiety being selected from the group consisting of halogen, alkyl, cycloalkyl, —CF$_3$, —CN, —C(O)OH, —(CH$_2$), —C(O)OH, OCF$_3$, -OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (Ia), $R^3$ is pyridyl, quinolinyl, or pyrazolyl, wherein said pyridyl, quinolinyl, or pyrazolyl is unsubstituted or substituted with one or more moieties which can be the same or different, each moiety being selected from the group consisting of Y, halogen, alkyl, cycloalkyl, —CF$_3$, —CN, —C(O)OH, —(CH$_2$)$_c$ —C(O)OH, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$. For example, $R^3$ can be quinolinyl, e.g., 3-quinolinyl, wherein said quinolinyl is unsubstituted or substituted with one or more halogen. In another example, $R^3$ is pyridyl e.g., 3-pyridyl, substituted with one Y group, wherein said Y group is aryl or heteroaryl, wherein said aryl or heteroaryl of Y is unsubstituted or substituted with one or more alkyl. In yet another example, $R^3$ is pyrazolyl substituted with one Y group, wherein said Y group is aryl or heteroaryl, wherein said aryl or heteroaryl of Y is unsubstituted or substituted with one or more alkyl.

In another embodiment of the compound of Formula (Ia), $R^2$ is heterocyclyl, cycloalkyl, or cycloalkenyl, wherein said heterocyclyl, cycloalkyl, or cycloalkenyl of $R^2$ is unsubstituted or substituted with one to four moieties, which can be the same or different, each moiety being alkyl, —C(O)$_2$H, —S(O)$_2$CH$_3$, —CH$_2$C(O)$_2$H, —C(O)—CH(OH)—CH$_3$, or —C(O)—CH(OH)—CH$_2$OH; and $R^3$ is pyridyl, quinolinyl, or pyrazolyl wherein said pyridyl, quinolinyl, or pyrazolyl is unsubstituted or substituted with one or more moieties which can be the same or different, each moiety being selected from the group consisting of Y, halogen, alkyl, cycloalkyl, —CF$_3$, —CN, —C(O)OH, —(CH$_2$)$_c$ —C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$.

In another embodiment of the compound of Formula (Ia), L is —CH$_2$ or —O—, or L is absent such that $R^2$ is bonded directly to the illustrated pyrimidine ring.

In another embodiment of the compound of Formula (Ia), Q is N.

In another embodiment of the compound of Formula (Ia), Q is C(H).

In some embodiments of the compound of Formula (I) and the compound of Formula (Ia), $R^2$ is selected from one of the following moieties:

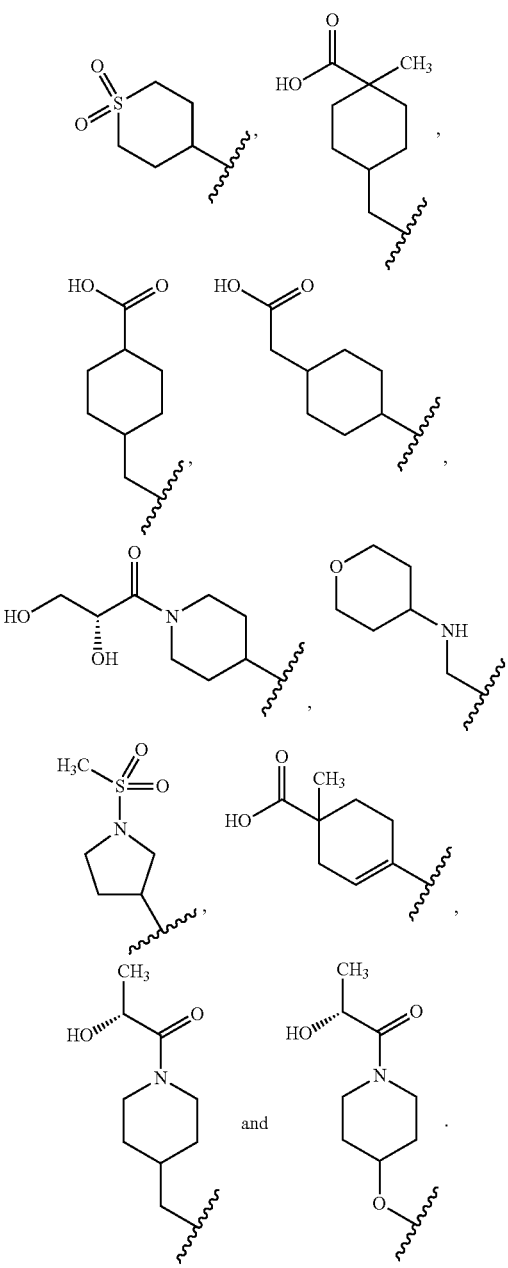

Non-limiting examples of the compounds of Formula (I) include compounds 1-37 as set forth below:

1
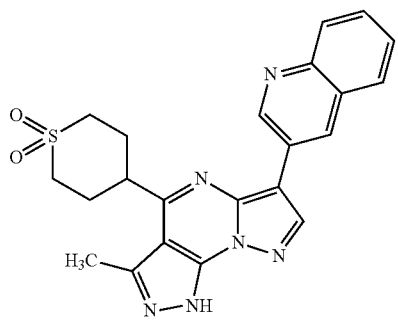
2
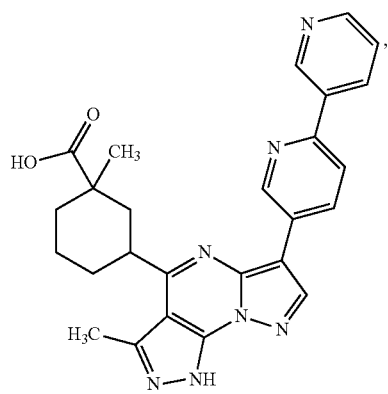
3
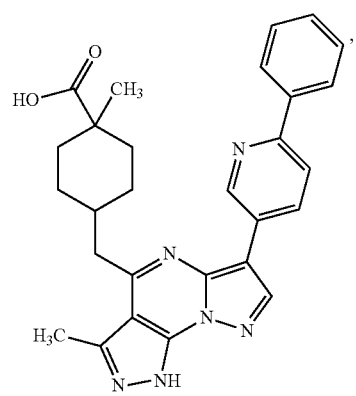
4
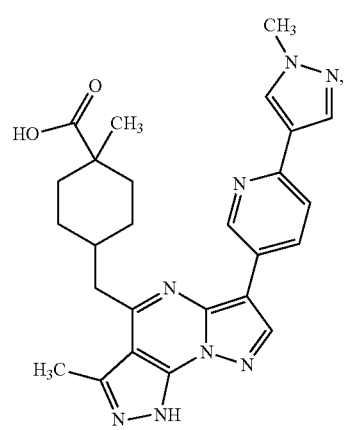
5
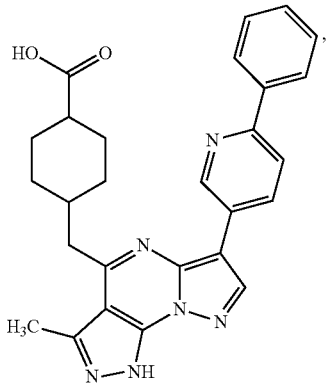
6
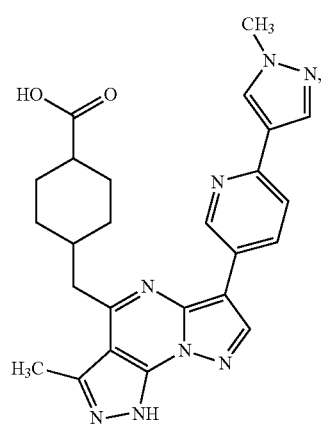
7
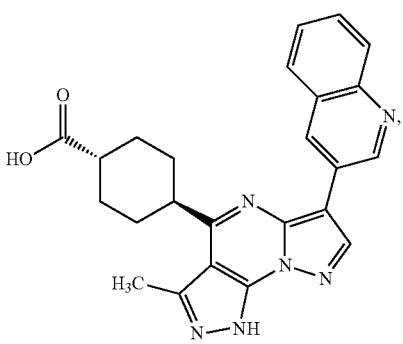
8
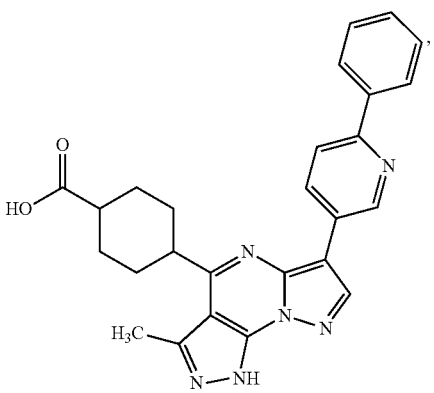

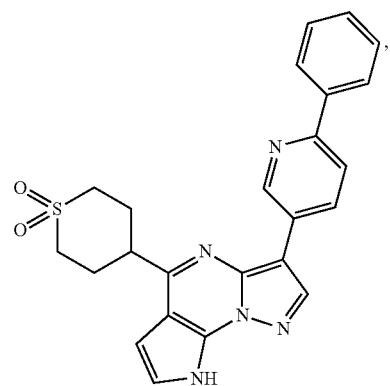
9
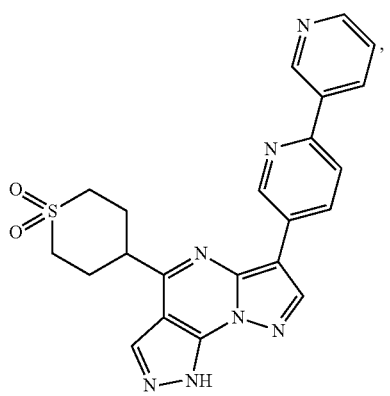
10
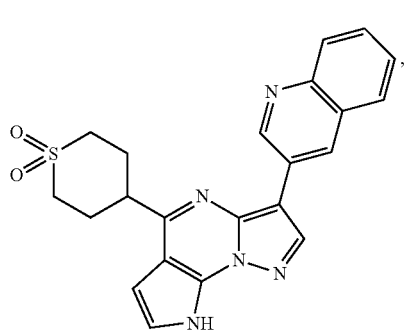
11
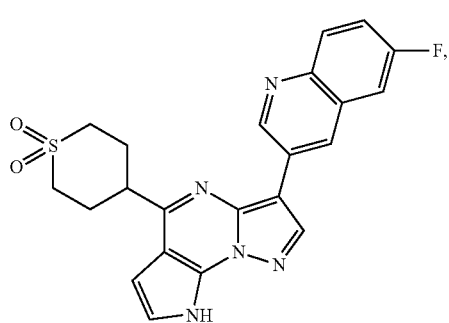
12
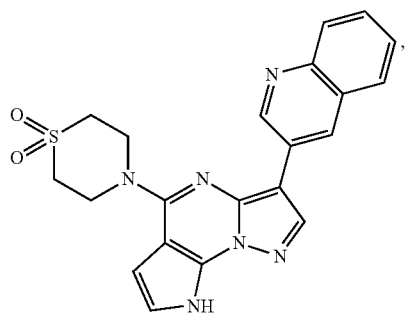
13
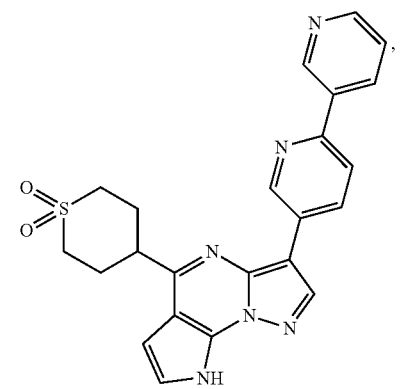
14
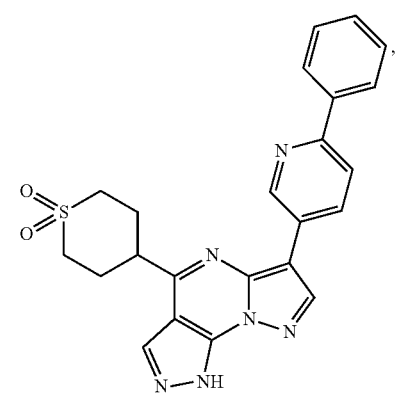
15
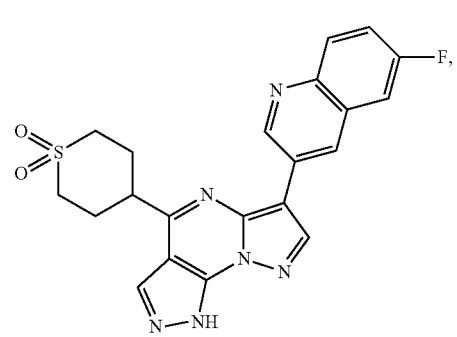
16

-continued
17
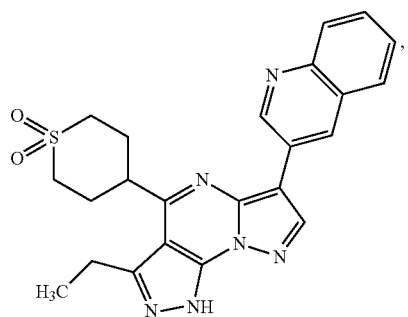
18
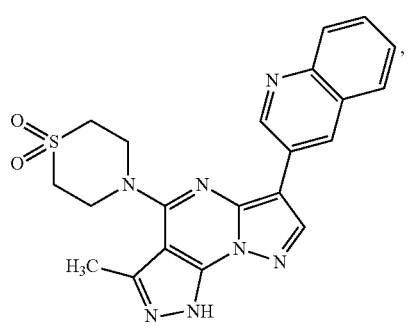
19
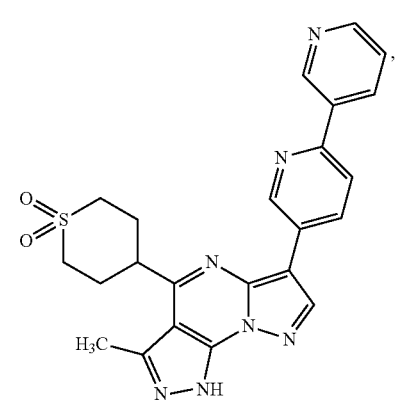
20
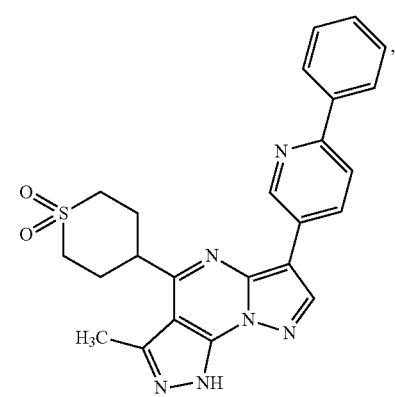
-continued
21
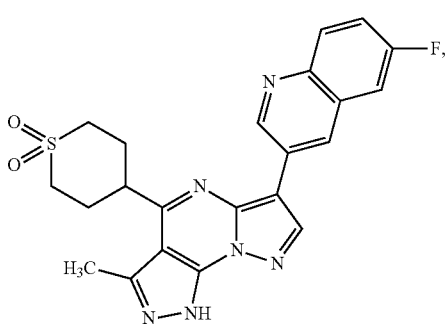
22
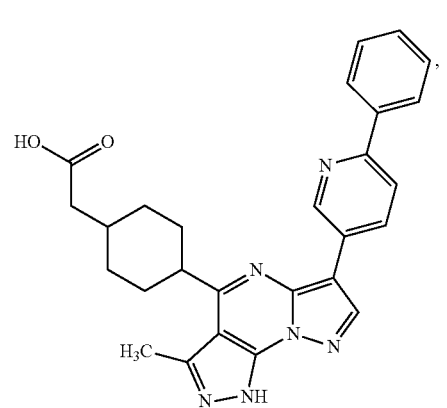
23
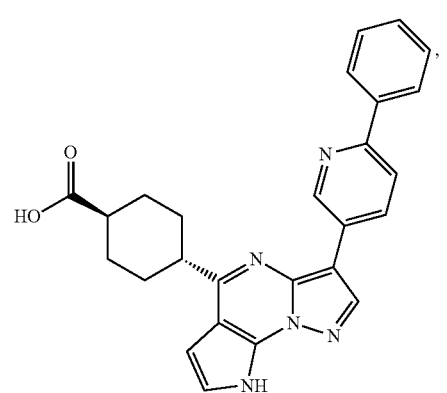
24
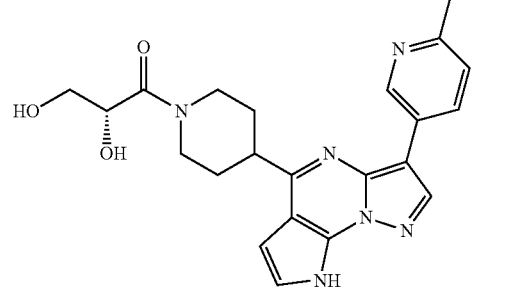

25
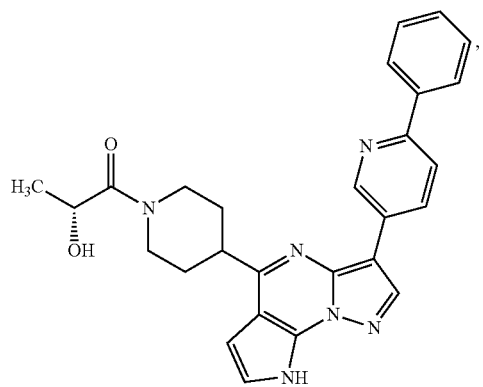
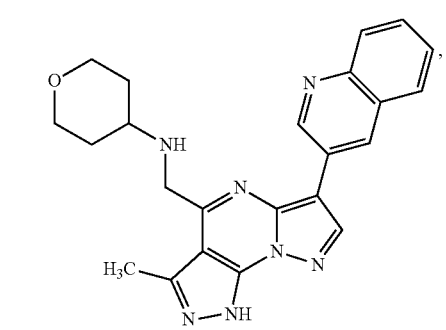
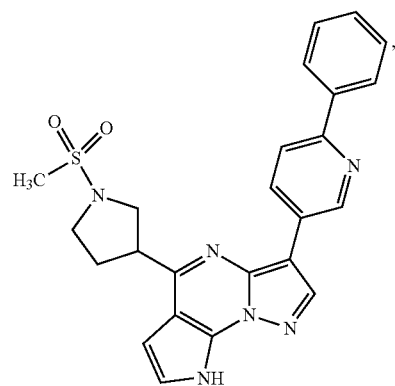
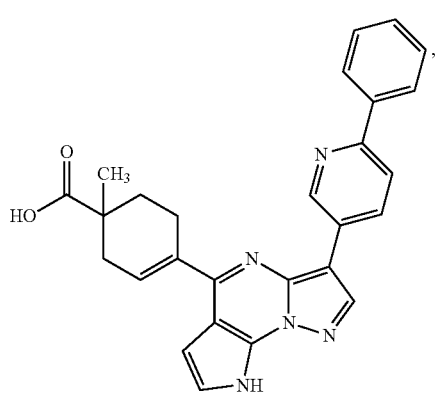
26
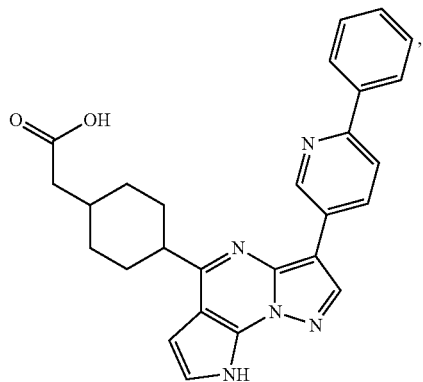
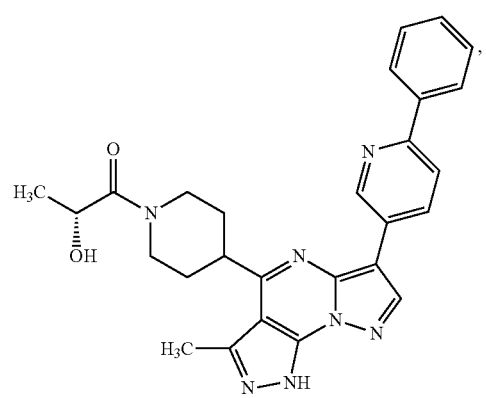
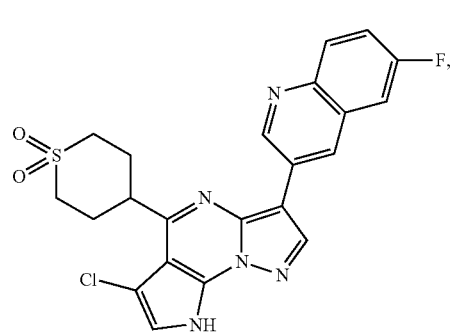
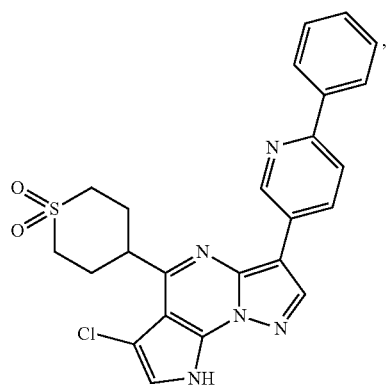

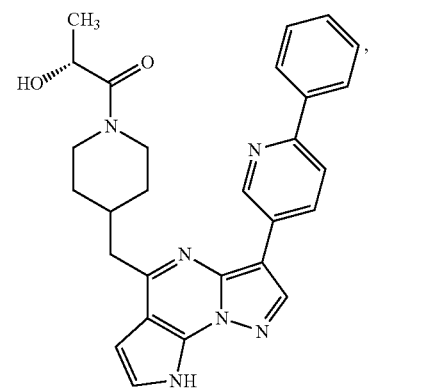

33

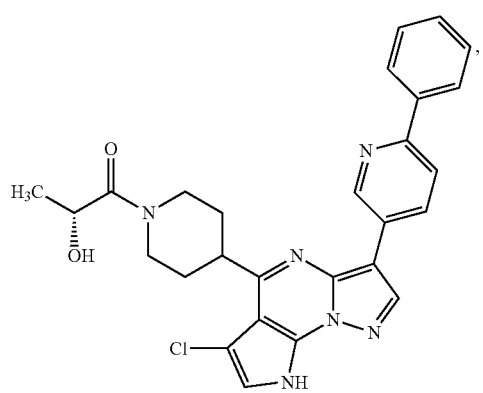

34

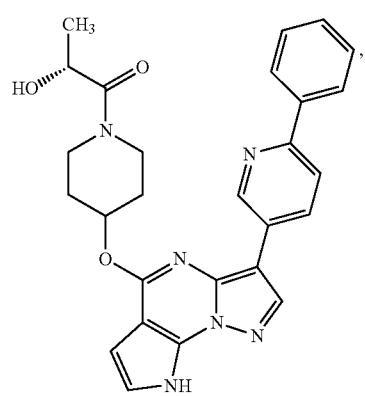

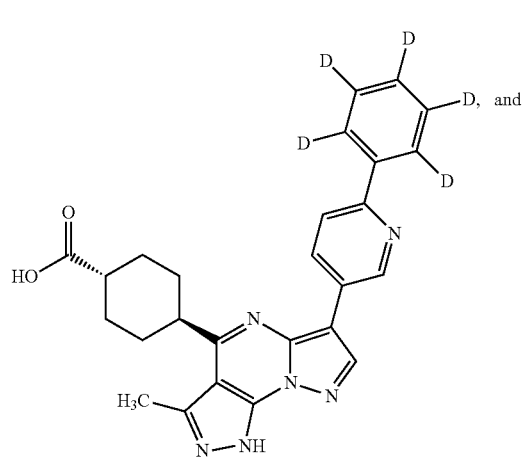

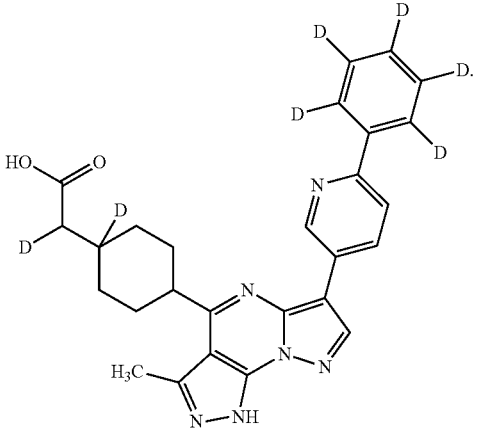

37 and pharmaceutically acceptable salts thereof.

The compounds according to the invention have pharmacological properties; in particular, the compounds of the present invention can be inhibitors, regulators or modulators of protein kinases, such as mTOR protein kinases. As inhibitors of mTOR, preferred compounds of the present invention can exhibit $IC_{50}$ values of less than about 5 µm, preferably about 0.001 to about 1.0 µm, and more preferably about 0.001 to about 0.1 µm. The assay methods are described in the Examples set forth below.

Methods for Making the Compounds of Formula (I)

The compounds of the Formula (I) can be prepared from known or readily prepared starting materials, following methods known to one skilled in the art of organic synthesis. Methods useful for making the compounds of Formula (I) are set forth in the Examples below. Alternative synthetic pathways and analogous structures will be apparent to those skilled in the art of organic synthesis. All stereoisomers and tautomeric forms of the compounds are contemplated.

EXAMPLES

Solvents, reagents, and intermediates that are commercially available were used as received. Reagents and intermediates that are not commercially available were preatee in the manner as described below. $^1$H NMR spectra were obtained on a Varian spectrometer (400 MHz and 500 MHz) are reported as ppm down field from $Me_4Si$ with number of protons, multiplicities, and coupling constants, in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. The retention time and observed parent ion are given. Flash column chromatography was performed using pre-packed normal phase silica from Biotage, Inc.

The following solvents, reagents and reaction conditions may be referred to by their abbreviations:

Aq: aqueous
g or gm: grams
psi: pounds per square inch
pH: concentration of hydronium ions in a solution ° C.: degrees Celsius
h: hours
THF: Tetrahydrofuran
Et$_2$O: diethyl ether
SEM: 2-(trimethylsilyl)ethoxymethyl
LC-MS: Liquid chromatography mass spectrometry
DCM: dichloromethane
N: Normal
ml: milliliter
NBS: N-Bromosuccinimide
NCS: N-Chlorosuccinimide
NIS: N-iodosuccinimide
rt: room temperature
MeOH: methanol
DIEA: diisopropylethylamine
EtOAc: ethyl acetate
EtOH: ethanol
DMF: dimethylformamide
WT %: weight percent
m/z: mass per charge
LiOH: lithium hydroxide
DMSO: dimethylsulfoxide
HPLC: high performance liquid chromatography
IPA: isopropanol
Ret: retention
$t_R$: retention time
RP: reverse phase
CH$_3$CN: acetonitrile
MeCN: acetonitrile
MeI: iodomethane
pTSA: para-toluene sulfonic acid
RT: retention time
NaOH: sodium hydroxide
CDI: N,N'-carbonyldiimidazole
mg: milligram
PMA: phosphomolybdic acid
CO$_2$: carbon dioxide
LiHMDS: Lithium bis(trimethylsilyl)amide
HMDS: hexamethyldisilazane
Pd/C: palladium on carbon
H$_2$: hydrogen gas
PdCl$_2$(dppf): [1,1'-bis(diphenylphosphino)ferrocene]dichloropalladium(II)
µmol: micromole
TFA: trifluoroacetic acid
NMP: N-methyl-2-pyrrolidone
min: minute
NaIO$_4$: sodium periodate
DME: dimethylethane
OsO$_4$: osmium tetroxide
Na$_2$S$_2$O$_3$: sodium thiosulfate
AcOH: acetic acid
NaBH$_3$CN: sodium cyanoborohydride
H$_2$O: water
BBN: 9-borabicyclo[3.3.1]nonane
CH$_2$Cl$_2$: dichloromethane
BOC: tertiary-butyloxycarbonyl
POCl$_3$: phosphorous oxychloride
NaHCO$_3$: sodium bicarbonate
NH$_4$Cl: ammonium chloride
Na$_2$SO$_4$: sodium sulphate
HCl: hydrogen chloride
M: Molar
mmol: millimolar
NH$_3$: ammonia
DIEA: diisopropylethylamine
Bu$_3$SnCN: tributyltin cyanide Pd[P(t-Bu)$_3$]$_2$: bis(tributyl)Phosphine)palladium
Pd(PPh$_3$)$_4$: tetrakis(triphenylphosphine)palladium
K$_2$CO$_3$: potassium carbonate
EDC: 1-ethyl-3-(3-dimethylaminopropyl)-carbodiimide
UV: ultraviolet
K$_3$PO$_4$: potassium phosphate
LDA: lithium diisopropylamide
Tf: trifluoromethanesulfonyl
NaH: sodium hydride Example 1

Preparation of Intermediate Compound Int-1g

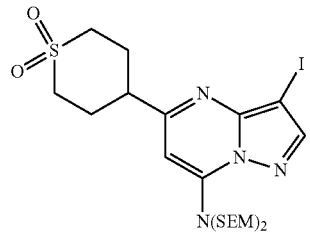

Step A—Synthesis of Ethyl 3-(3-ethoxy-3-oxopropanoyl)cyclopentanecarboxylate (Int-1a)

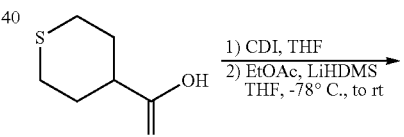

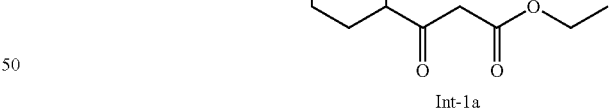

To a solution of tetrahydro-2H-thiopyran-4-carboxylic acid (2.0 g, 13.7 mmol) in THF (25 mL) was added CDI (2.66 g, 1.20 eq). The mixture was stirred at rt for 1 h. To a solution of LiHMDS (1.0 M in THF, 29 mL) in THF (30 mL) at −78° C. was added EtOAc (2.90 mL) dropwise. The mixture was stirred at −78° C. for 1 h, then the acid/CDI mixture was added through an addition funnel over 30 min at −78° C. The mixture was stirred at −78° C. for 1 h then allowed to warm up to rt over 2 h. The reaction was quenched with saturated NH$_4$Cl and extracted with diethyl ether. The combined organic layers were dried over Na$_2$SO$_4$, filtered and concentrated. The residue was purified by Biotage (CH$_2$Cl$_2$/EtOAc, Step B—Synthesis of 5-(Tetrahydro-2H-thiopyran-4-yl)pyrazolo[1,5-a]pyrimidin-7-ol (Int-1b)

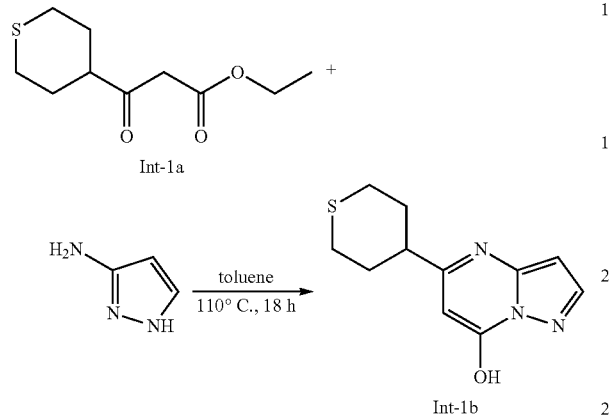

A mixture of ethyl 3-(3-ethoxy-3-oxopropanoyl)cyclopentanecarboxylate (1.51 g, 7.0 mmol) and 1H-pyrazol-3-amine (Int-1a, 0.60 g, 7.0 mmol) in toluene (10 mL) was heated at 110° C. under argon for 18 h and concentrated. The residue was triturated with EtOAc and the solid was collected by filtration and dried in high vacuum to give 1.53 g (93%) of the title compound as a white solid. LC/MS RT=1.13 Min (5 min method). Mass calculated for, M+H 236.08, observed 236.08.

Step C—Synthesis of 7-Chloro-5-(tetrahydro-2H-thiopyran-4-yl)pyrazolo[1,5-a]pyrimidine (Int-1c)

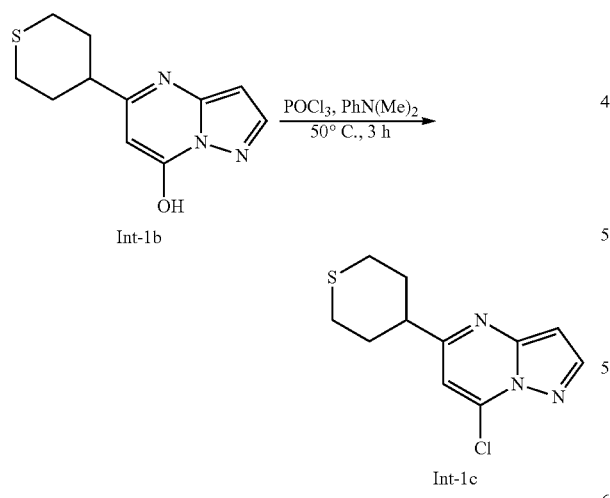

To a mixture of 5-(tetrahydro-2H-thiopyran-4-yl)pyrazolo[1,5-a]pyrimidin-7-ol (Int-1b, 1.50 g, 6.38 mmol) and dimethylaniline (2.0 mL, 15 mml) was added phosphoryl trichloride (20 mL). The mixture was heated at 50° C. for 5 h and concentrated. The residue was diluted with methylene chloride (50 mL) and quenched with saturated NaHCO₃ (50 mL). The mixture was separated and the aqueous layer was extracted with methylene chloride (50 mL×2). The combined organic layers were dried over Na₂SO₄, filtered and concentrated. The residue was purified by Biotage (CH₂Cl₂/EtOAc, 20:1 to 4:1). LC/MS RT=1.92 Min (5 min method). Mass calculated for, M+H 254.04, observed 254.04.

100:1 to 10:1) to give the title compound as a clear oil. LC/MS RT=1.73 min (5 min method). Mass calculated for, M+H 217.08, observed 217.08.

Step D—Synthesis of 5-(Tetrahydro-2H-thiopyran-4-yl)pyrazolo[1,5-a]pyrimidin-7-amine (Int-1d)

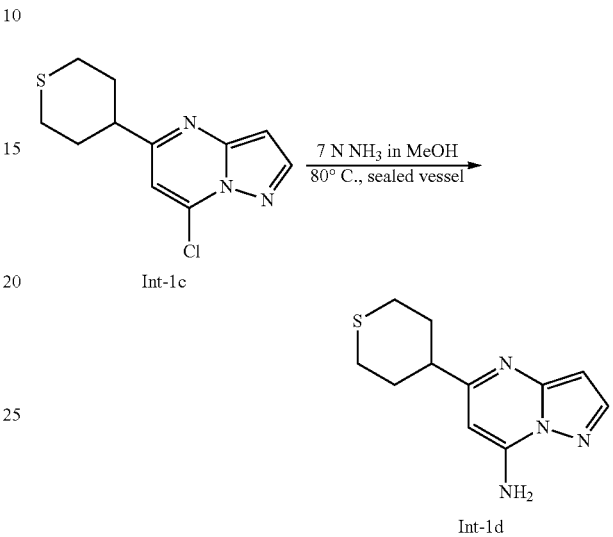

A mixture of 7-chloro-5-(tetrahydro-2H-thiopyran-4-yl)pyrazolo[1,5-a]pyrimidine (Int-1c, 1.52 g, 6.0 mmol) in a solution of ammonia in MeOH (7 N, 20 mL) was heated in sealed vessel at 80° C. for 5 h. The reaction mixture was cooled down and concentrated. The residue was dried in high vacuum and used for the next step without further purification. LC/MS RT=0.92 Min (5 min method). Mass calculated for, M+H 235.09, observed 235.09.

Step E—Synthesis of 5-(Tetrahydro-2H-thiopyran-4-yl)-N,N-bis((2-(trimethylsilyl)ethoxy)methyl)pyrazolo[1,5-a]pyrimidin-7-amine (Int-1e)

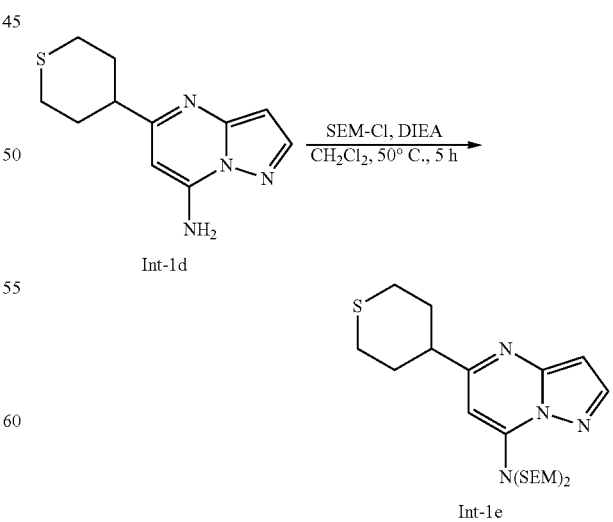

To a mixture of 5-(tetrahydro-2H-thiopyran-4-yl)pyrazolo[1,5-a]pyrimidin-7-amine (Int-1d, 1.41 g, 6.0 mmol) in CH$_2$Cl$_2$ (50 mL) was added DIEA (6.50 mL, 368 mmol) and SEM-Cl (3.30 mL, 18 mmol). The mixture was heated at 50° C. for 5 h under argon. The mixture was cooled down and quenched with saturated NaHCO$_3$ (100 mL) and extracted with CH$_2$Cl$_2$ (50 mL×3). The combined organic layers were dried over Na$_2$SO$_4$, filtered and concentrated. The residue was purified by Biotage (CH$_2$Cl$_2$/EtOAc, 20:1 to 5:1) to give the title compound as a light brown oil. LC/MS RT=2.95 Min (5 min method). Mass calculated for, M+H 495.26, observed 495.26.

Step F—5-(1,1-Dioxo-tetrahydro-2H-thiopyran-4-yl)-N,N-bis((2-(trimethylsilyl)ethoxy)methyl)pyrazolo[1,5-a]pyrimidin-7-amine (Int-1f)

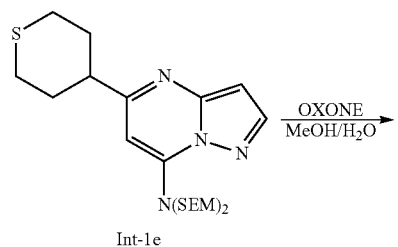

Int-1e

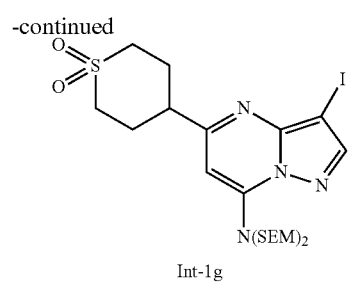

Int-1f

To a solution of 5-(tetrahydro-2H-thiopyran-4-yl)-N,N-bis((2-(trimethylsilyl)ethoxy)methyl)pyrazolo[1,5-a]pyrimidin-7-amine (Int-1e, 4.44 g, 9.0 mmol) in a 4:1 mixture of MeOH/H$_2$O (50 mL) was added NaHCO$_3$ (2.30 mg, 27 mmol) and OXONE (2.80 g, 27 mmol of active O). The mixture was stirred at rt for 6 h and diluted with water and extracted with EtOAc. The organic layer was washed with brine, dried over Na/SO$_4$, filtered and concentrated. The residue was purified by Biotage (CH$_2$Cl$_2$/EtOAc, 20:1 to 4:1) to give 3.25 g (68%) of the title compound as a light brown solid. LC/MS RT=2.72 Min (5 min method). Mass calculated for, M+H 527.25, observed 527.25.

Step G—3-Iodo-5-(1,1-dioxo-tetrahydro-2H-thiopyran-4-yl)-N,N-bis((2-(trimethylsilyl)ethoxy)methyl)pyrazolo[1,5-a]pyrimidin-7-amine (Int-1g)

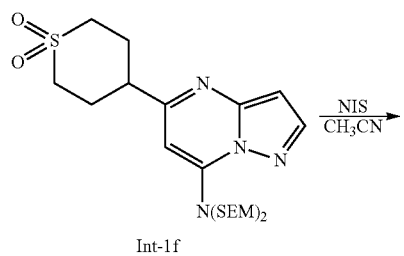

Int-1f

Int-1g

To a solution of 5-(1,1-dioxo-tetrahydro-2H-thiopyran-4-yl)-N,N-bis((2-(trimethylsilyl)ethoxy)methyl)pyrazolo[1,5-a]pyrimidin-7-amine (Int-1f, 3.20 g, 6.0 mmol) in CH$_3$CN (20 mL) was added NIS (1.35 g, 6.0 mmol). The mixture was stirred at rt for 1 h, diluted with EtOAc, washed with saturated Na$_2$S$_2$O$_3$ solution, dried over Na$_2$SO$_4$, filtered and concentrated. The residue was purified by Biotage (CH$_2$Cl$_2$/EtOAc, 20:1 to 5:1) to give 3.55 g (90%) of the title compound as a light brown solid. LC/MS RT=3.01 min (5 min method). Mass calculated for, M+H 653.14, observed 653.14.

Example 2

Preparation of Compound 1

Step A—Synthesis of 3-(Quinolin-3-yl)-5-(1,1-dioxo-tetrahydro-2H-thiopyran-4-yl)-N,N-bis((2-(trimethylsilyl)ethoxy)methyl)pyrazolo[1,5-c]pyrimidin-7-amine (Int-2a)

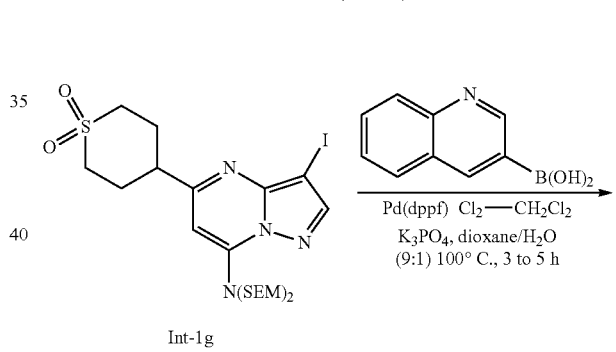

Int-1g

Int-2a

A mixture of 3-iodo-5-(1,1-dioxo-tetrahydro-2H-thiopyran-4-yl)-N,N-bis((2-(trimethylsilyl)ethoxy)methyl)pyrazolo[1,5-a]pyrimidin-7-amine (Int-1g, 654 mg, 1.0 mmol), 3-quinoline boronic acid (261 mg, 1.5 mmol), Pd(dppf)Cl$_2$-CH$_2$Cl$_2$ (82 mg, 0.10 mmol) and K$_3$PO$_4$ (640 mg, 3.0 mmol) in a 9:1 mixture of dioxane/H$_2$O (20 mL) was heated under argon at 100° C. for 3 h. The mixture was concentrated and purified by Biotage (CH$_2$Cl$_2$/EtOAc, 20:1 to 5:1) to give 586 mg (93%) of the title compound as a light brown solid. LC/MS RT=2.43 min (5 min method). Mass calculated for, M+H 654.29, observed 654.29.

Step B—Synthesis of 3-(Quinolin-3-yl)-5-(1,1-di-oxo-tetrahydro-2H-thiopyran-4-yl)-N,N-bis((2-(trimethylsilyl)ethoxy)methyl)pyrazolo[1,5-a]pyrimidin-7-amine (Int-2b)

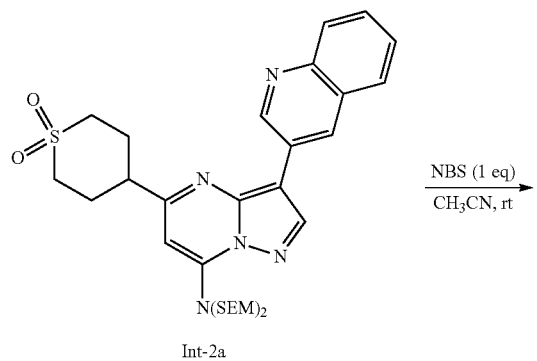

20:1 to 4:1) to give 210 mg (99%) of the title compound as a light brown solid. LC/MS RT=2.55 min (5 min method). Mass calculated for, M+H 732.20, observed 732.20.

Step C—Synthesis of 3-(Quinolin-3-yl)-5-(1,1-di-oxo-tetrahydro-2H-thiopyran-4-yl)-6-(1-ethoxyvinyl)-N,N-bis((2-(trimethylsilyl)ethoxy)methyl)pyrazolo[1,5-a]pyrimidin-7-amine (Int-2c)

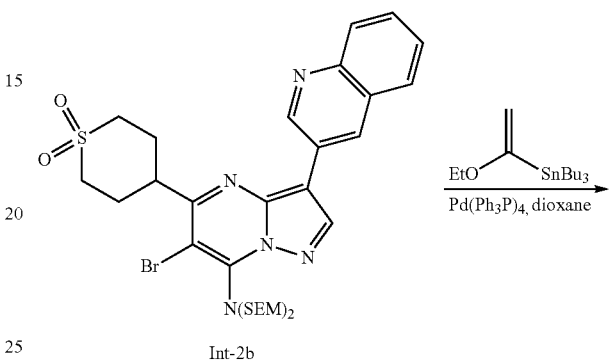

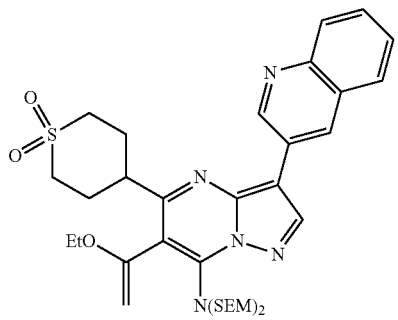

To a solution of 3-(quinolin-3-yl)-5-(1,1-dioxo-tetrahydro-2H-thiopyran-4-yl)-N,N-bis((2-(trimethylsilyl)ethoxy)methyl)pyrazolo[1,5-a]pyrimidin-7-amine (Int-2a, 190 mg, 0.29 mmol) in acetonitrile (5 mL) was added NBS (51 mg, 0.29 eq). The mixture was stirred at rt for 2 h and concentrated. The residue was purified by Biotage (CH$_2$Cl$_2$/EtOAc, A mixture of 3-(quinolin-3-yl)-5-(1,1-dioxo-tetrahydro-2H-thiopyran-4-yl)-N,N-bis((2-(trimethylsilyl)ethoxy)methyl)pyrazolo[1,5-a]pyrimidin-7-amine (Int-2b, 210 mg, 0.28 mmol), tributyl(1-ethoxyvinyl)stannane (310 mg, 0.84 mmol) and Pd(Ph$_3$P)$_4$ (31 mg, 0.028 mmol) in anhydrous dioxane (5.0 mL) was heated under argon at 100° C. for 24 h, cooled and concentrated. The residue purified by Biotage (CH$_2$Cl$_2$/EtOAc, 20:1 to 4:1) to give 169 mg (83%) of the title compound as a light brown solid. LC/MS RT=2.58 min (5 min method). Mass calculated for, M+H 724.33, observed 724.33.

Step D—Synthesis of 3-(Quinolin-3-yl)-5-(1,1-di-oxo-tetrahydro-2H-thiopyran-4-yl)-6-(1-ethoxyvinyl)-pyrazolo[1,5-a]pyrimidin-7-amine (Int-2d)

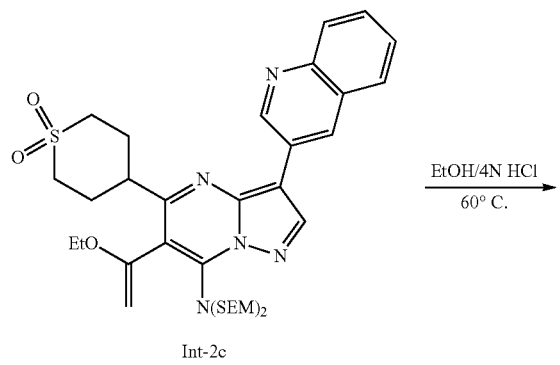

Int-2d 3-(quinolin-3-yl)-5-(1,1-dioxo-tetrahydro-2H-thiopyran-4-yl)-6-(1-ethoxyvinyl)-N,N-bis((2-(trimethylsilyl)ethoxy)methyl)pyrazolo[1,5-a]pyrimidin-7-amine (Int-2c, 169 mg, 0.23 mmol) in a 1:1 mixture of EtOH/4 N HCl (6.0 mL) was heated at 60° C. for 3 h and concentrated. The residue was purified by PrepLC to give 53 mg (53%) of the title compound (HCl salt) as a light yellow solid. LC/MS RT=2.95 min (10 min method). Mass calculated for, M+H 436.14, observed 436.14.

Step E—Synthesis of 3-(Quinolin-3-yl)-5-(1,1-di-oxo-tetrahydro-2H-thiopyran-4-yl)-6-methyl-dipyrazolo[1,5-a:4',3'-e]pyrimidine (Compound I)

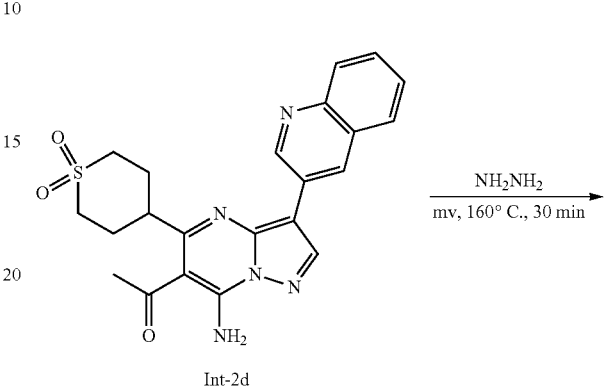

Int-2d

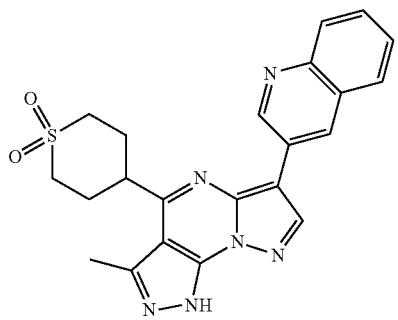

1

3-(quinolin-3-yl)-5-(1,1-dioxo-tetrahydro-2H-thiopyran-4-yl)-6-(1-ethoxyvinyl)-pyrazolo[1,5-a]pyrimidin-7-amine (Int-2d, 44 mg, 0.10 mmol) in hydrazine mono hydrate (2.0 mL) was heated at 160° C. by microwave for 30 min. The mixture was cooled and concentrated. The residue was purified by PrepLC to give 9.5 mg (22%) of the title compound (HCl salt) as a light yellow solid. LC/MS RT=2.76 min (10 min method). Mass calculated for, M+H 433.14, observed 433.14.

Example 3

Preparation of Compound 20 and Related Compounds 18, 19, and 21

Step A—Synthesis of Intermediate Int-3a

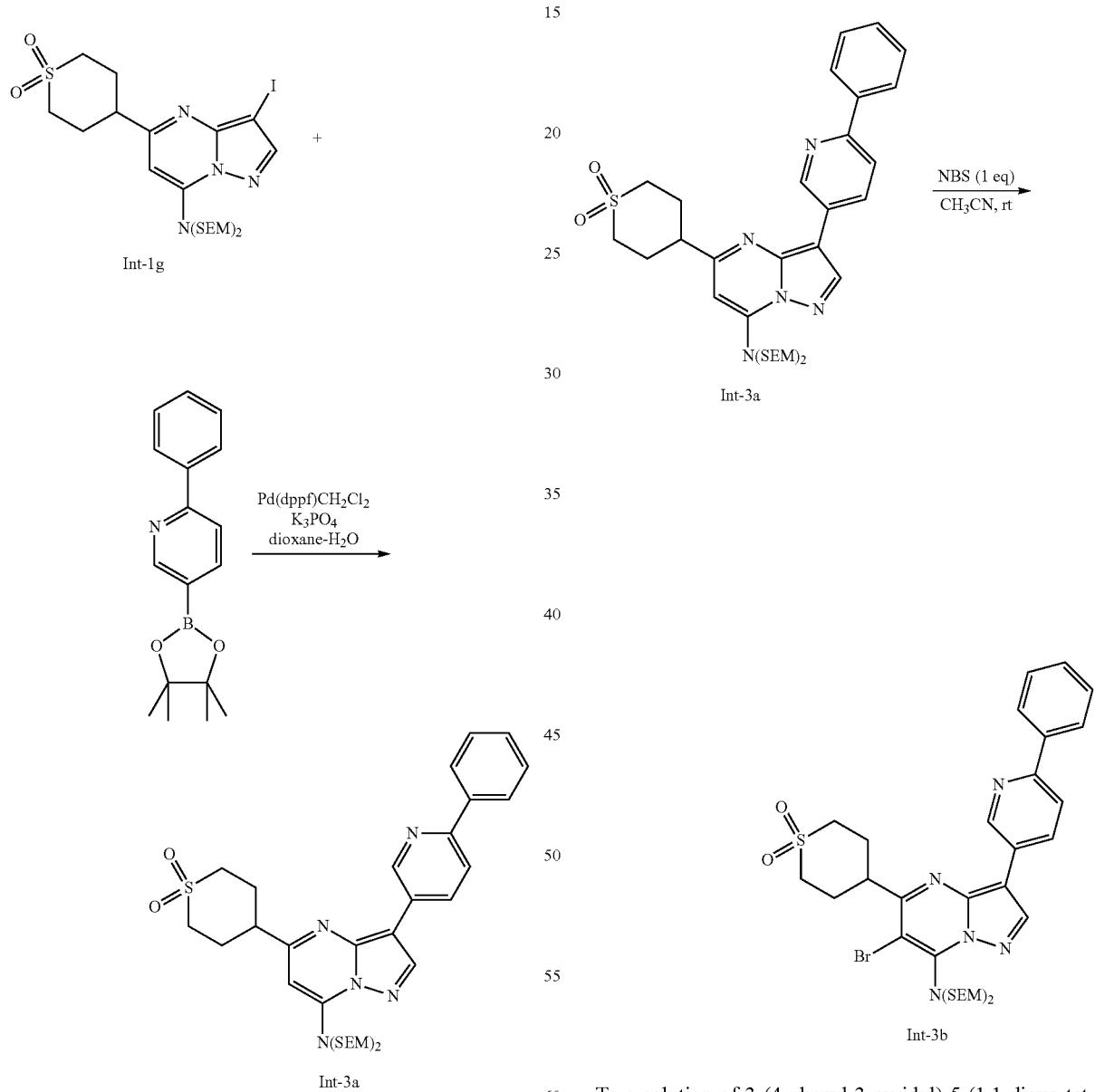

2-phenyl-5-(4,4,5,5-tetramethyl-1,3,2-dioxaborolan-2-yl) pyridine (616 mmol, 2.19 mg), $K_3PO_4$ (5.06 mmol, 1073 mg), and $PdCl_2(dppf)$ $CH_2Cl_2$ (0.17 mmol, 138 mg) was added to a solution of Int-1g (1.69 mmol, 1100 mg) in dioxane (15 mL) and $H_2O$ (3 mL). The resulting solution was stirred at 90° C. under argon overnight. The mixture was diluted with $H_2O$ and then extracted with ethyl acetate (x2). The combined organic layers were washed with brine and dried with $Na_2SO_4$. Evaporation and purification by column chromatography afforded Int-3a: LCMS $t_R$=2.69 min (5 min run, $UV_{254nm}$). Mass calculated for, M+679.3, observed m/z 680.3 (M+H).

Step B—Synthesis of 3-(Quinolin-3-yl)-5-(1,1-dioxo-tetrahydro-2H-thiopyran-4-yl)-N,N-bis((2-(trimethylsilyl)ethoxy)methyl)pyrazolo[1,5-a]pyrimidin-7-amine (Int-2b)

To a solution of 3-(4-phenyl-3-pyridyl)-5-(1,1-dioxo-tetrahydro-2H-thiopyran-4-yl)-N,N-bis((2-(trimethylsilyl) ethoxy)methyl)pyrazolo[1,5-a]pyrimidin-7-amine (Int-3a, 190 mg, 0.29 mmol) in acetonitrile (5 mL) was added NBS (51 mg, 0.29 eq). The mixture was stirred at rt for 2 h and concentrated. The residue was purified by Biotage ($CH_2Cl_2$/ EtOAc, 20:1 to 4:1) to give 210 mg (99%) of the title compound as a light brown solid (Int-3b). LC/MS $t_R$=2.55 (5 min method). Mass calculated for, M+H 757.20, observed 757.20 & 759.20 (doublet for Br).

Step C—Preparation of Int-3d

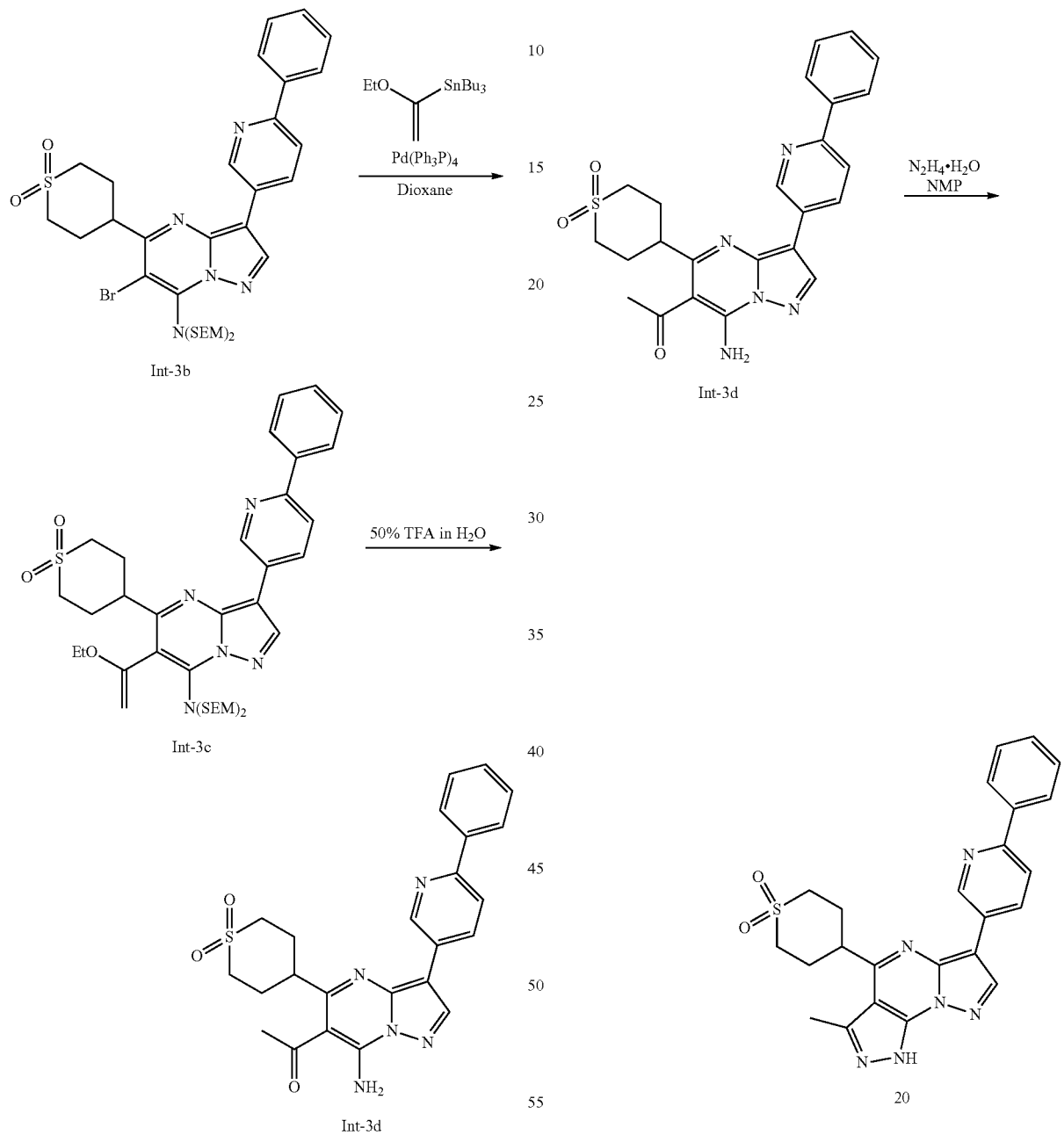

A degassed mixture of Int-3b (203 mg, 0.27 mmol), Pd(PPh₃)₄ (31 mg, 0.027 mmol), tributyl(vinyl)stannane (255 mg, 0.80 mmoL) in CH₃CN (6 mL) was heated at 150° C. under microwave condition for 60 min. The reaction mixture was cooled to room temperature, filtered through 9:1 SiO₂: KF plug and concentrated in vacuo. The crude was treated with 50% TFA in H₂O (4 mL) for 1 h. The reaction mixture was concentrated in vacuo. The crude compound Int-3c was treated with 50% TFA in H₂O (2 mL) for 1 h. Concentration and purification afforded compound Int-3d: LCMS $t_R$=3.58 min (5 min run, $UV_{254nm}$). Mass calculated for, M+469.0, observed m/z 470.0 (M+H).

Step D—Preparation of Compound 20

Int-3d (10.1 mg, 0.022 mmoL) was heated under microwave conditions with N₂H₄.H₂O (100 μL) and NMP (1 mL) first at 100° C. for 30 min and then at 200° C. for 1 h. Purification with prep-LC provided compound 20: LCMS $t_R$=3.00 Min (10 min run, $UV_{254nm}$). Mass calculated for, M+458.1, observed m/z 459.1 (M+H).

By essentially the analogous procedures detailed above for Steps A-D, compounds 18, 19, and 21 were prepared from Int-1g. LC/MS data for compounds 18, 19, and 21 are set forth below.

18

Compound 18: LCMS $t_R$=2.68 min (10 min run, $UV_{254nm}$).
Mass calculated for, M+433.1, observed m/z 434.1 (M+H).

19

Compound 19: LCMS $t_R$=2.53 min (10 min run, $UV_{254nm}$)
Mass calculated for, M+459.1, observed m/z 460.1 (M+H).

21

Compound 21: LCMS $t_R$=2.97 min (10 min run, $UV_{254nm}$).
Mass calculated for, M+450.1, observed m/z 451.1 (M+H).

Example 4

Preparation of Compounds 5 and 6

Step A—Synthesis of ethyl 4-(2-tert-butoxy-2-oxoethylidene)cyclohexanecarboxylate (Int-4a)

Int-4a

To a 250 mL round-bottom flask was charged 100 mL anhydrous THF followed by NaH (60% in mineral oil, 800 mg, 20 mmol). The resulting suspension was broken up by sonication and stirred at room temperature. To this suspension was added dropwise tert-butyl diethylphosphonoacetate (5.05 g, 20 mmol) in 10 mL THF. The resulting clear solution was stirred at room temperature for 30 minutes. After 30 minutes, the reaction was cooled to 0° C. in ice bath. While stirring at 0° C., ethyl 4-oxocyclohexanecarboxylate (3.10 g, 18.2 mmol) was added dropwise in 10 mL THF. Upon completion of addition, the reaction was warmed to room temperature and allowed to stir 18 hours. After 18 hours, the reaction was diluted with 200 mL DCM and washed with $H_2O$ and extracted twice more with DCM. The combined organics were dried over Na$_2$SO$_4$ and reduced in vacuo. The resulting oil was taken on without further purification.

Step B—Synthesis of ethyl 4-(2-tert-butoxy-2-oxoethyl)cyclohexanecarboxylate (Int-4b)

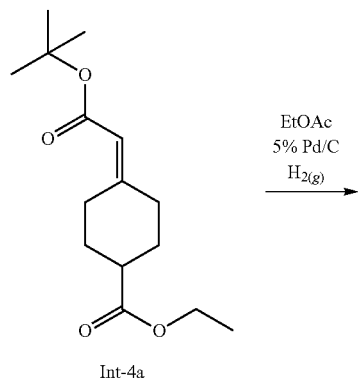

To a 250 mL round-bottom flask was charged ethyl 4-(2-tert-butoxy-2-oxoethylidene)cyclohexanecarboxylate (Int-4a, 5.38 g, 19.90 mmol) followed by EtOAc (100 mL). The flask was flushed with argon and then 5% palladium on carbon was added. The flask was sealed and degassed under vacuum. H$_2$ (g) was added in a balloon and the reaction was allowed to stir 18 hours under hydrogen atmosphere. After 18 hours, the reaction mixture was filtered through celite. The solvent was removed in vacuo and the resulting oil was taken on without further purification.

Step C—Synthesis of 2-(4-(ethoxycarbonyl)cyclohexyl)acetic acid (Int-4c)

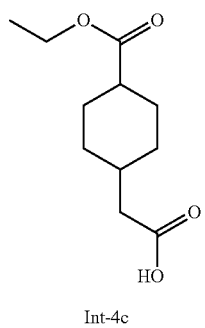

To a 100 mL round-bottom flask was charged ethyl 4-(2-tert-butoxy-2-oxoethyl)cyclohexanecarboxylate (Int-4b, 2.00 g, 7.40 mmol) and 4N HCl in 1,4-dioxane. The resulting solution was stirred at room temperature for 2 hours. At this point the solvent was removed in vacuo and the resulting residue was diluted with DCM and washed with H$_2$O. The organic layer was dried over Na$_2$SO$_4$ and reduced in vacuo. The resulting residue was taken on without further purification.

Step D—Synthesis of ethyl 4-(4-ethoxy-2,4-dioxobutyl)cyclohexanecarboxylate (Int-4-e)

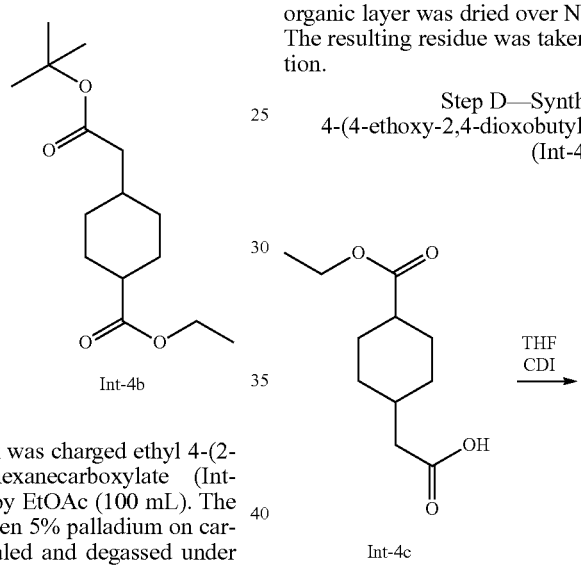

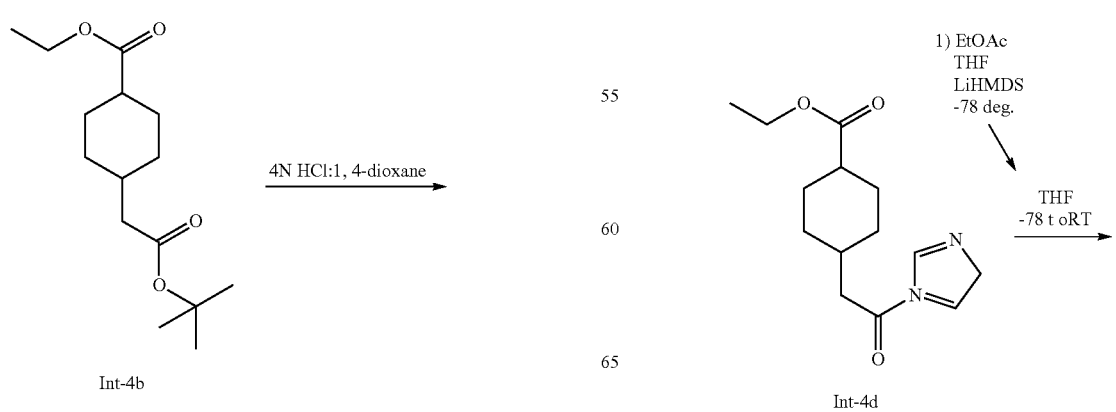

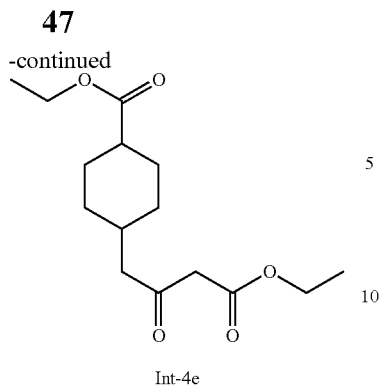

Int-4e

To a 100 mL round-bottom vessel was charged 2-(4-(ethoxycarbonyl)cyclohexyl)acetic acid (Int-4c, 4.03 g, 18.79 mmol) and THF (20 mL). To this solution was added N,N'-carbonyldiimidazole (3.66 g, 22.55 mmol). The resulting solution was allowed to stir 18 hours at room temperature. After 18 hours, in a separate 250 mL round-bottom vessel, 80 mL THF was added and the flask was flushed with argon. This solution was cooled to −78° C. in dry ice/IPA bath. To this solution was added LiHMDS (1.0 M in THF, 39.46 mmol, 39.46 mL). To the resulting solution was added dropwise dry EtOAc (40.4 mmol, 3.95 mL). This solution was allowed to stir at −78° C. for one hour. After one hour, the solution of crude ethyl 4-(2-(1H-imidazol-1-yl)-2-oxoethyl)cyclohexanecarboxylate (Int-4d) in THF was added dropwise. This solution was allowed to gradually warm to room temperature and the reaction was stirred overnight. After 18 hours, the reaction was quenched with saturated NH$_4$Cl$_{(aq)}$ and extracted with Et$_2$O (x3). The combined organics were dried over Na$_2$SO$_4$ and the residue was purified via silica gel chromatography to yield the title compound as clear oil. Yield=2.33 g.

Step E—Synthesis of ethyl 4-((7-hydroxypyrazolo[1,5-a]pyrimidin-5-yl)methyl)cyclohexanecarboxylate (Int-4f)

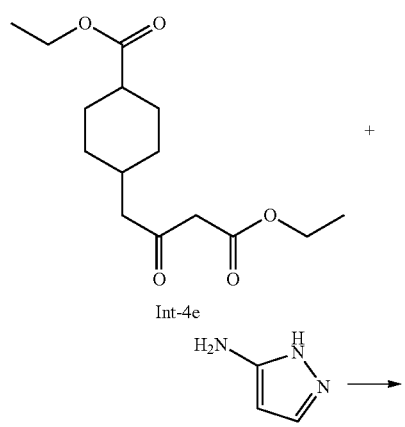

Int-4e

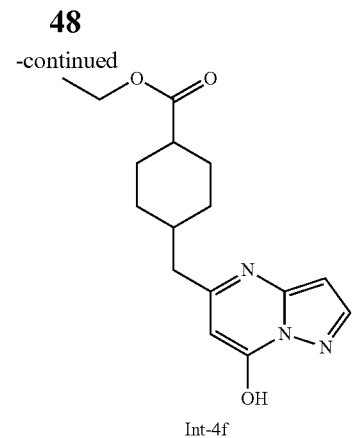

Int-4f

To a 50 mL round-bottom flask containing ethyl 4-(4-ethoxy-2,4-dioxobutyl)cyclohexanecarboxylate (Int-4e, 2.33 g, 8.19 mmol) was added 3-amino-1H-pyrazole (681 mg, 8.19 mmol). The flask was heated via heat gun to ensure mixing of the oils, and then the reaction was shaken at 100° C. for 18 hours. After 18 hours, the resulting solid was taken up in EtOH and then the solvent was removed in vacuo to dry product. The product was then pumped dry on high vacuum overnight to further dry the product. The compound was taken on without further purification.

Step F—Synthesis of ethyl 4-((7-chloropyrazolo[1,5-a]pyrimidin-5-yl)methyl)cyclohexanecarboxylate (Int-4g)

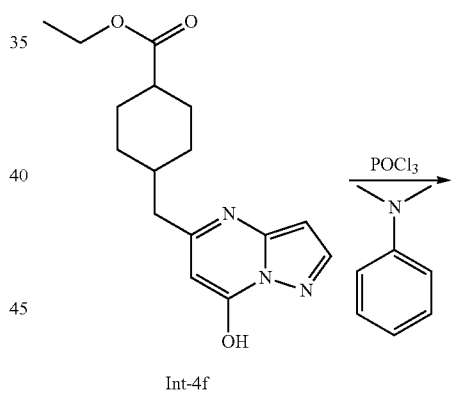

Int-4f

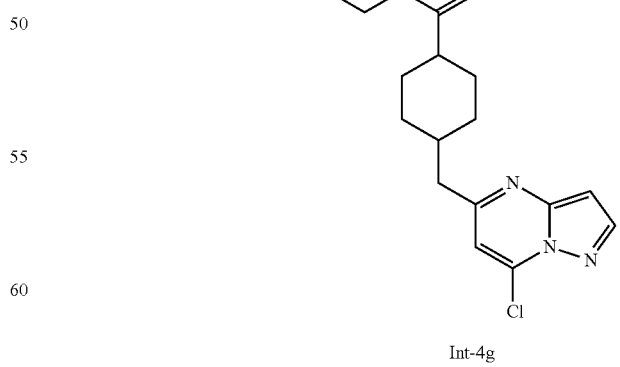

Int-4g

To a 100 mL round-bottom flask was charged ethyl 4-((7-hydroxypyrazolo[1,5-a]pyrimidin-5-yl)methyl)cyclohexanecarboxylate (Int-4f, 2.48 g, 8.19 mmol), N,N-dimethylaniline (4 mL) and POCl₃ (40 mL). The resulting solution was allowed to stir at room temperature for 18 hours. After 18 hours, the solvent was removed in vacuo. The residue was cooled to 0° C. in ice bath. The cooled residue was slowly quenched with saturated NaHCO₃ (aq), and then extracted with DCM (x3). The combined organic extracts were dried over Na₂SO₄ and the residue purified via silica gel chromatography to yield the title compound as clear oil. Yield=2.29 g.

Step G—Synthesis of ethyl 4-((7-aminopyrazolo[1,5-a]pyrimidin-5-yl)methyl)cyclohexanecarboxylate (Int-4h)

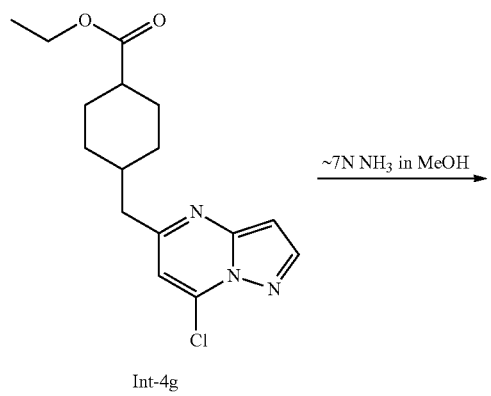

Int-4g

The combined organics were dried over Na₂SO₄ and then the solvent was removed in vacuo. The resulting solid was taken on without further purification.

Step H—Synthesis of ethyl 4-((7-(bis((2-(trimethylsilyl)ethoxy)methyl)amino)-pyrazolo[1,5-a]pyrimidin-5-yl)methyl)cyclohexanecarboxylate (Int-4i)

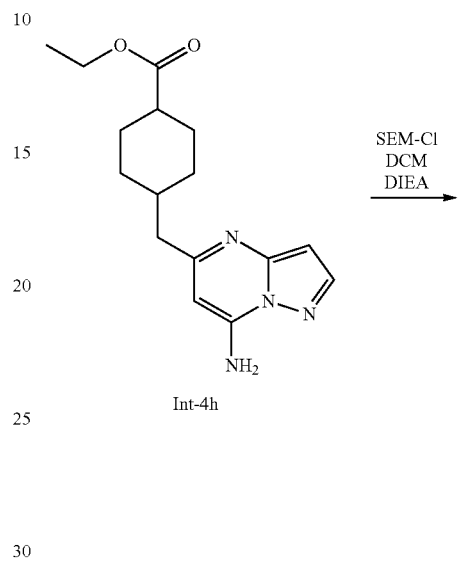

Int-4h

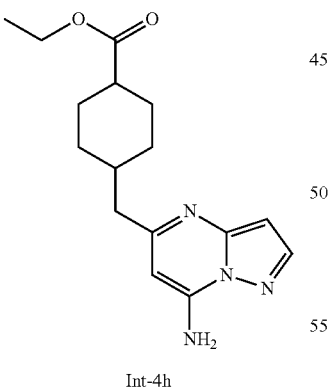

Int-4h

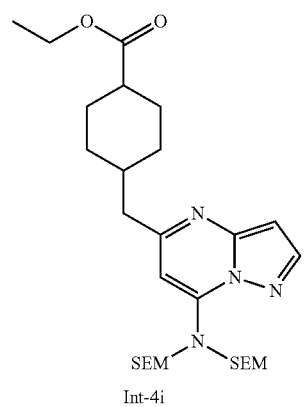

Int-4i

To a 10-20 mL microwave vessel was charged ethyl 4-((7-chloropyrazolo[1,5-a]pyrimidin-5-yl)methyl)cyclohexanecarboxylate (Int-4g, 2.29 g, 7.12 mmol). To this was added ~7N NH₃ in methanol (15 mL). The resulting solution was stirred at 90° C. for 4 hours. After 4 hours, the reaction was cooled to room temperature and diluted with DCM (100 mL). This solution was washed with H₂O and the organic layer was extracted. The aqueous phase was again extracted with DCM.

To a 100 mL round-bottom flask was added ethyl 4-((7-aminopyrazolo[1,5-a]pyrimidin-5-yl)methyl)cyclohexanecarboxylate (Int-4h, 7.12 mmol) and DCM (50 mL). To this suspension was added DIEA (3.72 mL, 21.36 mmol). To the resulting solution was added dropwise SEM-Cl (3.78 mL, 21.36 mmol) in 10 mL DCM. The reaction was allowed to stir at room temperature for 30 minutes. After 30 minutes, the reaction was reduced in vacuo and the residue purified via silica gel chromatography to yield the title compound. Yield=2.64 g.

Step I—Synthesis of ethyl 4-((7-(bis((2-(trimethylsilyl)ethoxy)methyl)amino)-3-iodopyrazolo[1,5-a]pyrimidin-5-yl)methyl)cyclohexanecarboxylate (Int-4j)

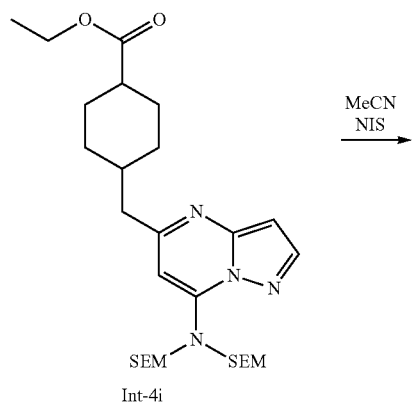

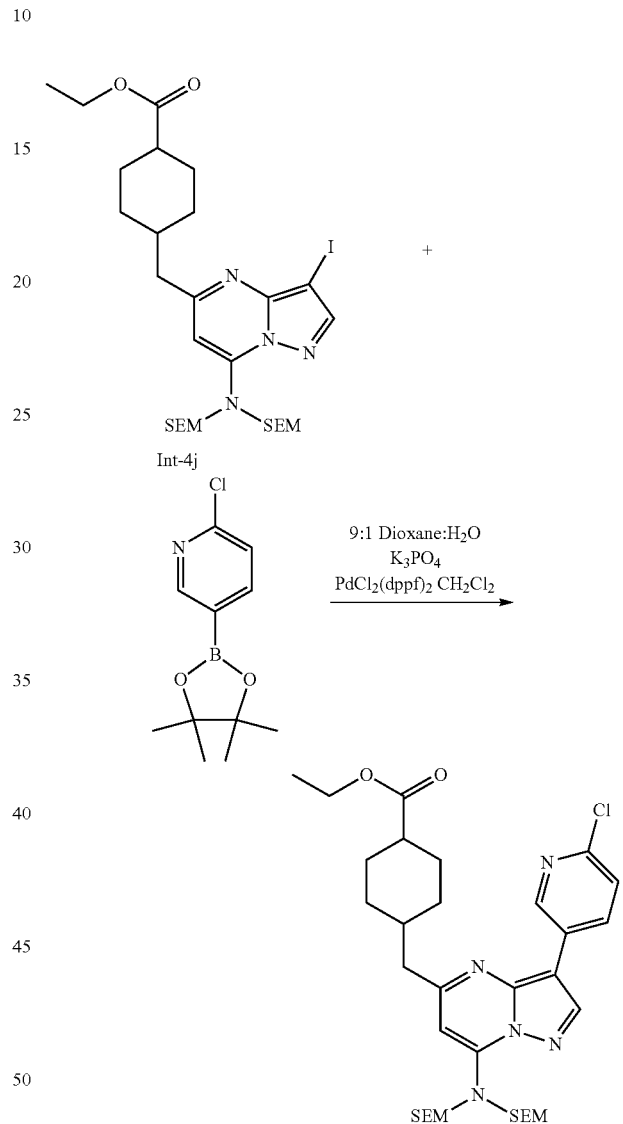

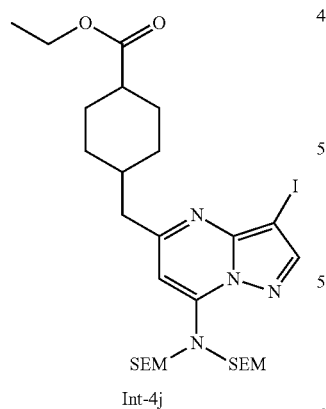

To a 100 mL round-bottom flask was charged ethyl 4-((7-(bis((2-(trimethylsilyl)ethoxy)methyl)amino)pyrazolo[1,5-a]pyrimidin-5-yl)methyl)cyclohexanecarboxylate (Int-4i, 2.64 g, 4.69 mmol) and N-iodosuccinimide (1.16 g, 5.16 mmol). To this mixture was added MeCN (40 mL). The resulting solution was stirred at room temperature overnight. After 18 hours, the reaction was reduced in vacuo and the residue was purified via silica gel chromatography to yield the title compound. Yield=2.94 g.

Step J—Synthesis of ethyl 4-((7-(bis((2-(trimethylsilyl)ethoxy)methyl)amino)-3-(6-chloropyridin-3-yl)pyrazolo[1,5-a]pyrimidin-5-yl)methyl)cyclohexanecarboxylate (Int-4k)

To a 10-20 mL microwave vessel was charged ethyl 4-((7-(bis((2-(trimethylsilyl)ethoxy)methyl)amino)-3-iodopyrazolo[1,5-a]pyrimidin-5-yl)methyl)cyclohexanecarboxylate (Int-4j, 2.94 g, 4.27 mmol), 6-chloropyridine-3-boronic acid pinacol ester (1.07 g, 4.48 mmol), $K_3PO_4$ (2.72 g, 12.81 mmol), and $PdCl_2(dppf)_2 \cdot CH_2Cl_2$ (349 mg, 0.43 mmol). To this was added 9:1 1,4-dioxane:$H_2O$. The vial was flushed with argon, sealed, and stirred at 100° C. overnight. After 18 hours, the reaction was cooled to room temperature and diluted with DCM. The reaction was washed with water and the aqueous phase was extracted again with DCM. The combined organics were dried over $Na_2SO_4$ and the residue puri- Step K—Synthesis of ethyl 4-((7-(bis((2-(trimethylsilyl)ethoxy)methyl)amino)-3-(6-phenylpyridin-3-yl)pyrazolo[1,5-a]pyrimidin-5-yl)methyl)cyclohexanecarboxylate (Int-4l)

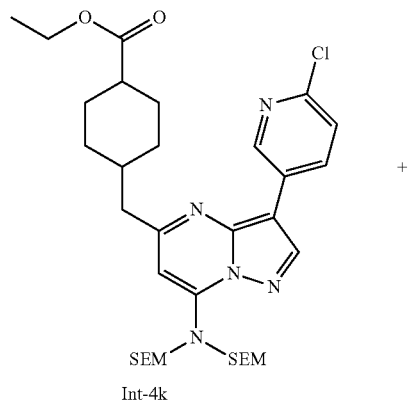

Step L—Synthesis of ethyl 4-((7-(bis((2-(trimethylsilyl)ethoxy)methyl)amino)-6-bromo-3-(6-phenylpyridin-3-yl)pyrazolo[1,5-a]pyrimidin-5-yl)methyl)cyclohexanecarboxylate (Int-4m)

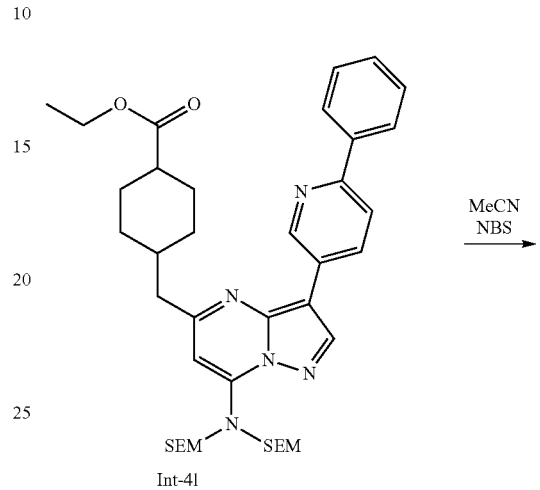

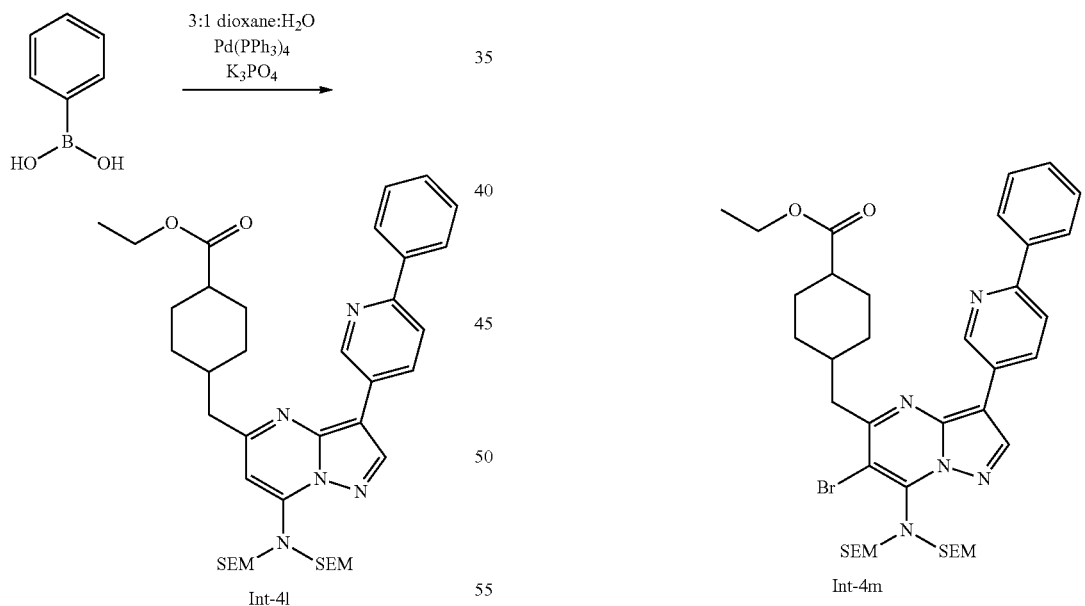

In a 2-5 mL microwave vial was charged ethyl 4-((7-(bis((2-(trimethylsilyl)ethoxy)methyl)amino)-3-(6-chloropyridin-3-yl)pyrazolo[1,5-a]pyrimidin-5-yl)methyl)cyclohexanecarboxylate (Int-4k, 300 mg, 0.45 mmol), phenylboronic acid (108 mg, 0.89 mmol), $K_3PO_4$ (189 mg, 0.89 mmol), and $Pd(PPh_3)_4$ (52 mg, 0.045 mmol). To this was added 3:1 1,4-dioxane:$H_2O$ (4 mL). The vial was flushed with argon and sealed. The reaction was heated to 140° C. for 20 minutes in a microwave synthesizer. The reaction was then diluted with DCM (30 mL) and washed with $H_2O$. The organic phase was dried over $Na_2SO_4$ and the residue was purified via silica gel chromatography to yield the title compound. Yield=265 mg.

To a 20 mL scintillation vial was charged ethyl 4-((7-(bis((2-(trimethylsilyl)ethoxy)methyl)amino)-3-(6-phenylpyridin-3-yl)pyrazolo[1,5-a]pyrimidin-5-yl)methyl)cyclohexanecarboxylate (Int-4l, 265 mg, 0.37 mmol) and N-bromosuccinimide (80 mg, 0.45 mmol). To this was added acetonitrile (5 mL). The resulting solution was stirred at room temperature for 18 hours. At 18 hours, the reaction was reduced in vacuo and the residue was purified via silica gel chromatography to yield the title compound as yellow oil. Yield=255 mg.

Step M—Synthesis of ethyl 4-((7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)methyl)cyclohexanecarboxylate (Int-4n)

Step N—Synthesis of ethyl 4-((6-acetyl-7-amino-3-(6-phenylpyridin-3-yl)pyrazolo[1,5-a]pyrimidin-5-yl)methyl)cyclohexanecarboxylate (Int-4o)

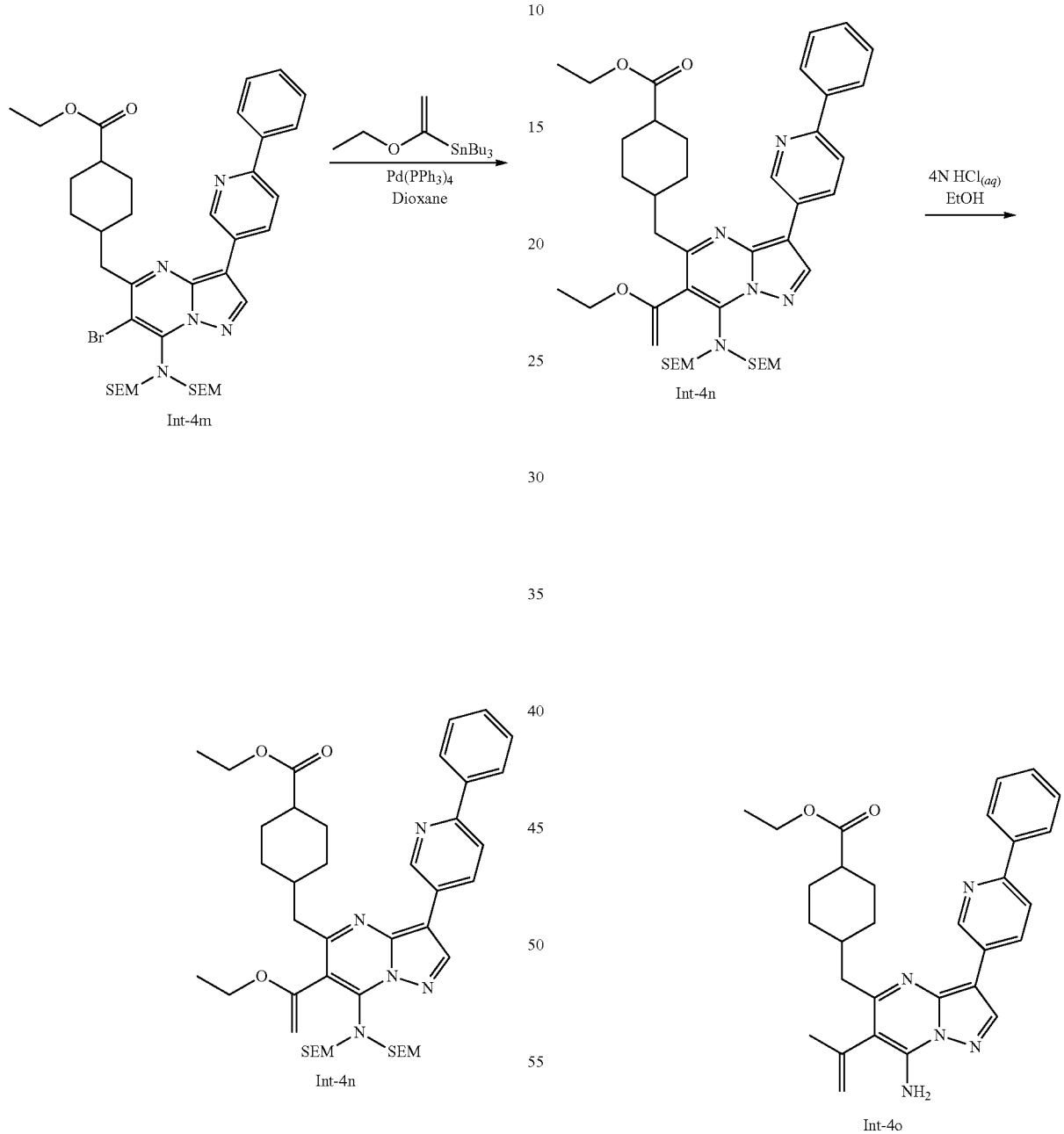

in vacuo and the residue was purified via silica gel chromatography to yield the title compound. Yield=113 mg.

To a 2-5 mL microwave vessel was charged ethyl 4-((7-(bis((2-(trimethylsilyl)ethoxy)methyl)amino)-6-bromo-3-(6-phenylpyridin-3-yl)pyrazolo[1,5-a]pyrimidin-5-yl)methyl)cyclohexanecarboxylate (Int-4m, 150 mg, 0.19 mmol), Pd(PPh$_3$)$_4$ (33 mg, 0.029 mmol), tributyl (1-ethoxyvinyl)tin (190 μL, 0.56 mmol), and 1,4-dioxane (2 mL). The vial was flushed with argon and sealed. The reaction was heated to 100° C. for 18 hours. After 18 hours, the solvent was removed To a 20 mL scintillation vial containing ethyl 4-((7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)methyl)cyclohexanecarboxylate (Int-4n, 113 mg, 0.144 mmol) was added EtOH (2 mL) followed by 4N HCl$_{(aq)}$. The resulting cloudy suspension was stirred at room temperature 1 hour, at which time the solution was now homogenous. The solvent was removed in vacuo and excess solvent was pumped off on high vacuum. The compound was taken on without further purification.

Step O—Synthesis of 4-((3-methyl-6-(6-phenylpyridin-3-yl)-1H-dipyrazolo[1,5-a:4',3'-e]pyrimidin-4-yl)methyl)cyclohexanecarboxylic acid (Compound 5)

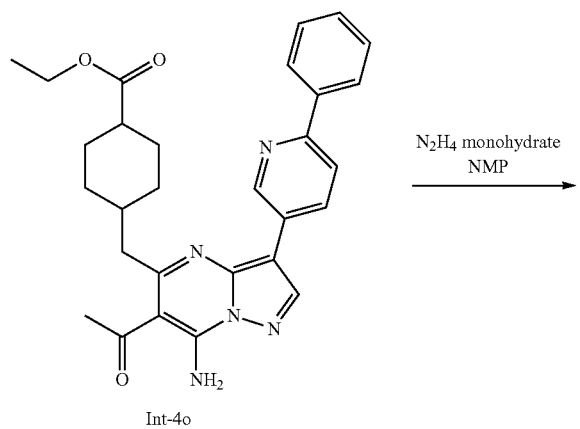

Int-4o

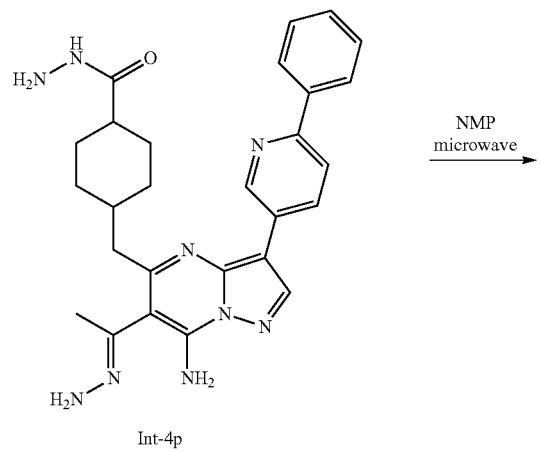

Int-4p

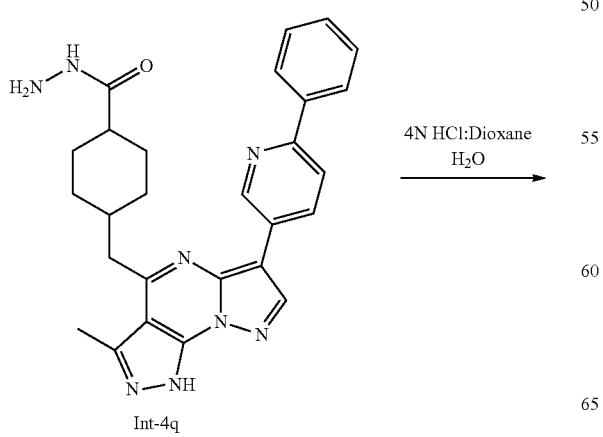

Int-4q

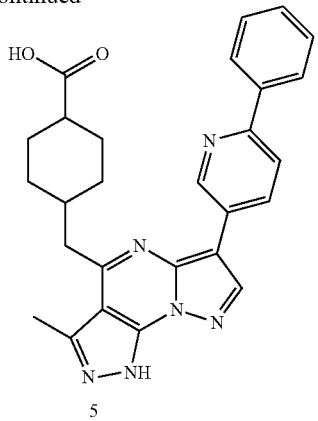

5

To a 20 mL scintillation vial was charged ethyl 4-((6-acetyl-7-amino-3-(6-phenylpyridin-3-yl)pyrazolo[1,5-a]pyrimidin-5-yl)methyl)cyclohexanecarboxylate (Int-4o, 72 mg, 0.144 mmol). To this vial was added NMP (2 mL) followed by hydrazine monohydrate (1 mL). The reaction was stirred at room temperature for 18 hours. At 18 hours, the hydrazine monohydrate was removed in vacuo and the crude 4-((7-amino-6-(1-hydrazonoethyl)-3-(6-phenylpyridin-3-yl)pyrazolo[1,5-a]pyrimidin-5-yl)methyl)cyclohexanecarbohydrazide (Int-4p) was transferred into 2-5 mL microwave vessel. The vial was sealed and heated to 200° C. for 45 minutes in microwave. After 45 minutes, the NMP was removed in vacuo using chlorobenzene as a cosolvent. The residue was dried on high vacuum over night. The crude 4-((3-methyl-6-(6-phenylpyridin-3-yl)-1H-dipyrazolo[1,5-a:4',3'-e]pyrimidin-4-yl)methyl)cyclohexanecarbohydrazide (Int-4q) was taken up in 4 N HCl in 1,4-dioxane (2 mL). To this was added H₂O (1 mL). This solution was stirred at 70° C. for 2 hours. After 2 hours, the solvent was removed in vacuo. The residue was purified via reverse-phase preparatory HPLC to yield 4-((3-methyl-6-(6-phenylpyridin-3-yl)-1H-dipyrazolo[1,5-a:4',3'-e]pyrimidin-4-yl)methyl)cyclohexanecarboxylic acid (5) (m+H=467.23, retention time=3.66 min).

Preparation of 4-((3-methyl-6-(6-(1-methyl-1H-pyrazol-4-yl)pyridin-3-yl)-1H-dipyrazolo[1,5-a:4',3'-e]pyrimidin-4-yl)methyl)cyclohexanecarboxylic acid (Compound 6)

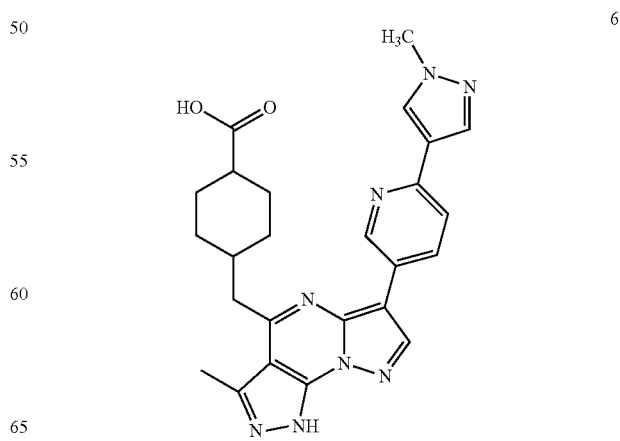

6

4-((3-methyl-6-(6-(1-methyl-1H-pyrazol-4-yl)pyridin-3-yl)-1H-dipyrazolo[1,5-a:4',3'-e]pyrimidin-4-yl)methyl)cyclohexanecarboxylic acid (Compound 6) was prepared in a manner similar to the synthesis of Compound 5. To prepare Compound 6, Int-4-k was reacted with 1-methylpyrazole-4-boronic acid pinacol ester substituted phenylboronic acid in Step K. Steps K-N were performed as described above. In the last step, the reaction mixture was reduced in vacuo and purified via reverse-phase preparatory HPLC to 4-((3-methyl-6-(6-(1-methyl-1H-pyrazol-4-yl)pyridin-3-yl)-1H-dipyrazolo[1,5-a:4',3'-e]pyrimidin-4-yl)methyl)cyclohexanecarboxylic acid as an off-yellow solid (6). (M+H=471.33, retention time=3.07 min).

Example 5

Preparation of Compound 22

Step A—Synthesis of Ethyl 1,4-dioxaspiro[4.5]decane-8-carboxylate (Int-5a)

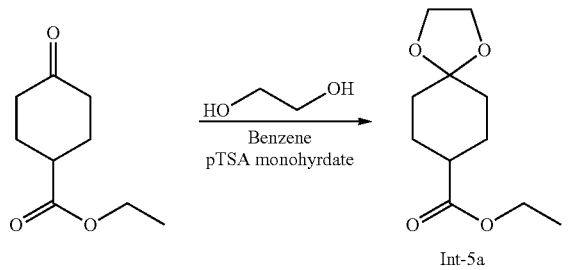

Ethyl 4-oxocyclohexane carboxylate (122.56 mmol, 20.86 g) and para-toluenesulfonic acid monohydrate (12.56 mmol, 2.33 g) were charged to a 1000 mL round-bottom flask. To this flask was added benzene (300 mL) followed by ethylene glycol (0.37 mol, 20.5 mL). The resulting bi-layer solution was refluxed overnight using a Dean-Stark trap. Upon cooling, the reaction mixture was diluted in 300 mL DCM and washed with 300 mL saturated $NaHCO_{3(aq)}$. DCM was used to extract from the aqueous layer (x3) and the combined organics were dried over $Na_2SO_4$. The residue was taken up in DCM and purified by silica gel chromatography using a 0% to 50% ethyl acetate in hexanes gradient. The product was monitored via PMA stain. Chromatography yielded 17.05 grams (79.58 mmol, 65% yield) ethyl 1,4-dioxaspiro[4.5]decane-8-carboxylate (Int-5a).

Step B—Synthesis of 1,4-Dioxaspiro[4,5]decane-8-carboxylic acid (Int-5b)

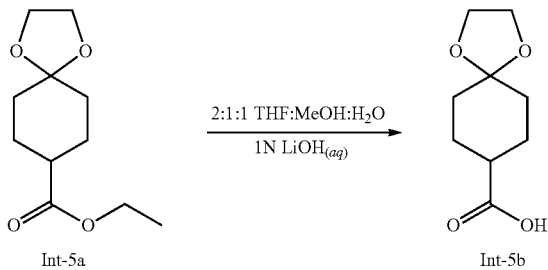

Ethyl 1,4-dioxaspiro[4.5]decane-8-carboxylate (Int-5a, 79.58 mmol, 17.05 g) was taken up in 300 mL 2:1 $THF:H_2O$ in 500 mL round-bottom flask. To this solution was added lithium hydroxide monohydrate (120 mmol, 5.01 g). To this was added 100 mL MeOH. The reaction was allowed to stir overnight at room temperature. The reaction mixture was acidified to pH=3 with 1N $HCl_{(aq)}$ and extracted with 100 mL DCM (x5). The combined organics were then dried over $Na_2SO_4$ and the solvents were removed in vacuo to yield 1,4-dioxaspiro[4.5]decane-8-carboxylic acid (Int-5b) (14.96 g, 100% yield) as a white solid.

Step C—Synthesis of Ethyl 3-oxo-3-(1,4-dioxaspiro [4.5]decan-8-yl)propanoate (Int-5d)

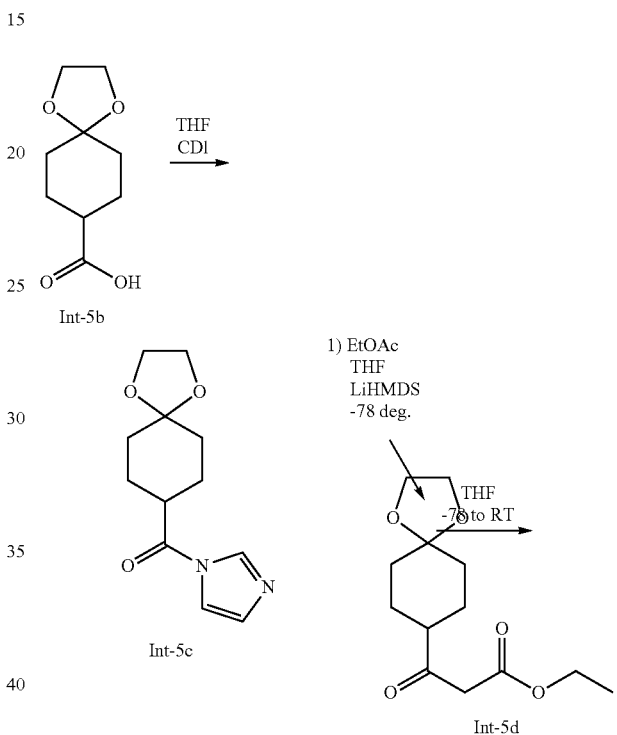

1,4-Dioxaspiro[4.5]decane-8-carboxylic acid (Int-5b, 80.34 mmol, 14.96 g) was charged to a 500 mL round-bottom flask. To this flask was added anhydrous THF (200 mL), followed by N,N'-carbonyldiimidazole (96.41 mmol, 15.63 g). After vigorous release of $CO_2$ gas, the reaction was flushed with argon, sealed, and allowed to stir overnight at room temperature under argon.

After 18 hours, in a separate, sealed and argon-flushed 1000 mL round-bottom flask, LiHMDS (1.0 M in THF, 168.7 mmol) was added to 200 mL anhydrous THF stirring at −78° C. To this solution was added dropwise anhydrous ethyl acetate (173 mmol, 16.9 mL). This solution was allowed to stir at −78° C. for 1 hour prior to dropwise addition of the crude (1H-imidazol-1-yl)(1,4-dioxaspiro[4.5]decan-8-yl)methanone (Int-5c) solution that had been stirring since the previous day. The reaction was allowed to stir and warm to room temperature overnight.

The reaction was then quenched with saturated $NH_4Cl_{(ac)}$ (500 mL) and extracted with $Et_2O$ (x2). The combined organics were then washed with $H_2O$, saturated brine, and dried over $Na_2SO_4$. The solvent was removed in vacuo and the residue was taken up in DCM. The residue was purified by silica gel chromatography (0% to 60% ethyl acetate in hexanes gradient) to yield ethyl 3-oxo-3-(1,4-dioxaspiro[4.5]decan-8-yl)propanoate (Int-5d) (11.26 g, 55% yield) as a pale yellow oil.

Step D—Synthesis of 5-(1,4-dioxaspiro[4.5]decan-8-yl)pyrazolo[1,5-a]pyrimidin-7-ol (Int-5e)

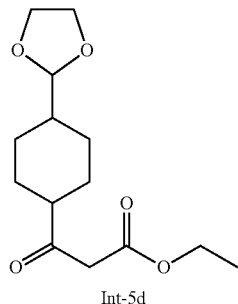

Int-5d

+

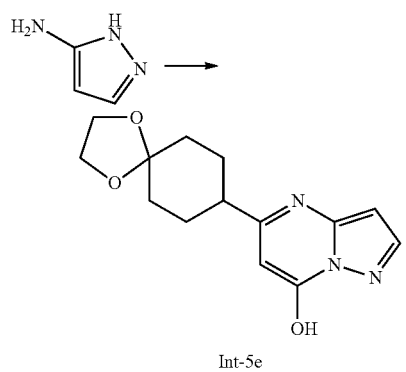

Int-5e

To a 20 mL scintillation vial containing ethyl 3-oxo-3-(1,4-dioxaspiro[4.5]decan-8-yl)propanoate (Int-5d, 11.7 mmol, 3.00 g) was added 3-amino-1H-pyrazole (11.7 mmol, 973 mg). The mixture was mixed and heated neat at 100° C. for 3 hours. The resulting off-white solid was taken up in EtOH (100 mL) and reduced in vacuo to remove water formed during cyclization. This solid was taken forward without further purification.

Step E—Synthesis of 7-chloro-5-(1,4-dioxaspiro[4.5]decan-8-yl)pyrazolo[1,5-a]pyrimidine (Int-5f)

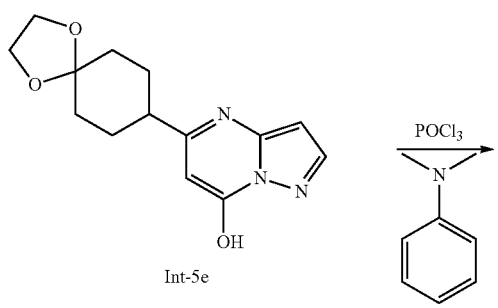 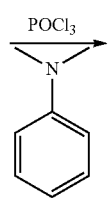

Int-5e

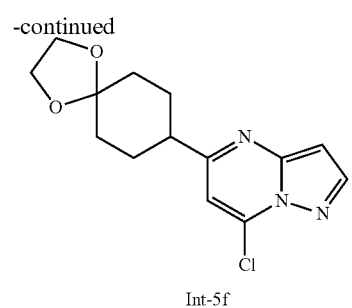

Int-5f 5-(1,4-dioxaspiro[4.5]decan-8-yl)pyrazolo[1,5-a]pyrimidin-7-ol (Int-5e, 11.7 mmol) was charged to 250 mL round-bottom flask. To this flask was added 4 mL N,N-dimethylaniline, followed by 40 mL POCl$_3$. This suspension was sonicated to break up the starting material and stirred at room temperature for 18 hours. After 18 hours, all starting material had dissolved. The solution was reduced in vacuo and cooled to 0° C. in an ice bath. The reaction was then quenched with sat. NaHCO$_{3(aq)}$ and extracted with DCM (x3). The combined organics were dried over Na$_2$SO$_4$ and the solvent was removed in vacuo. The resulting oil was purified via silica gel column with a 20% to 100% ethyl acetate in hexanes gradient to yield 7-chloro-5-(1,4-dioxaspiro[4.5]decan-8-yl)pyrazolo[1,5-a]pyrimidine (Int-5f) (2.65 grams, 77% across 2 steps) as a white solid.

Step F—Synthesis of 5-(1,4-dioxaspiro[4.5]decan-8-yl)pyrazolo[1,5-a]pyrimidin-7-amine (Int-5k)

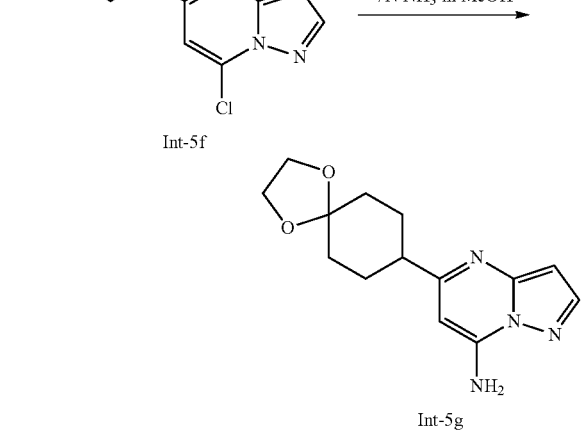

7-chloro-5-(1,4-dioxaspiro[4.5]decan-8-yl)pyrazolo[1,5-a]pyrimidine (Int-5f, 5.58 mmol, 1.64 g) was charged to a 10-20 mL microwave vessel. To this vessel was added 10 mL ~7 N NH$_3$ in methanol. The vessel was sealed and heated at 100° C. for 18 hours. After 18 hours, the reaction was cooled to room temperature and diluted with 100 mL DCM. The resulting solution was washed with saturated NaHCO$_{3(aq)}$ and extracted with DCM twice more. The combined organics were Na$_2$SO$_4$ and the solvent was removed in vacuo to yield 5-(1,4-dioxaspiro[4.5]decan-8-yl)pyrazolo[1,5-a]pyrimidin-7-amine (Int-5g) (1.52 g, 99% yield) as a pale orange solid.

Step G—Synthesis of 4-(7-aminopyrazolo[1,5-a]pyrimidin-5-yl)cyclohexanone (Int-5h)

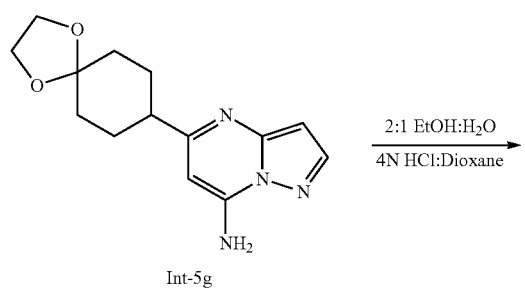

In a 40 mL scintillation vial was combined 5-(1,4-dioxaspiro[4.5]decan-8-yl)pyrazolo[1,5-a]pyrimidin-7-amine (Int-5g, 5.54 mmol, 1.52 g), EtOH (10 mL), H₂O (4 mL) and 4N HCl:dioxane (4 mL). The vial was capped, sealed and the reaction was heated to 80° C. overnight. After 18 hours, the reaction was cooled to room temperature and diluted with DCM (100 mL). The solution was washed with saturated NaHCO₃(aq) and extracted with DCM twice more. The combined organics were dried over Na₂SO₄ and the solvent was removed in vacuo to yield 4-(7-aminopyrazolo[1,5-a]pyrimidin-5-yl)cyclohexanone (Int-5h) (1.18 g, 93% yield) as a pale orange solid.

Step H—Synthesis of 4-(7-(bis((2-(trimethylsilyl)ethoxy)methyl)amino)pyrazolo[1,5-a]pyrimidin-5-yl)cyclohexanone (Int-51)

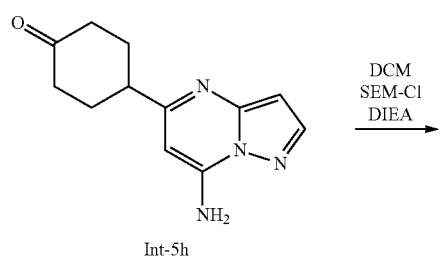

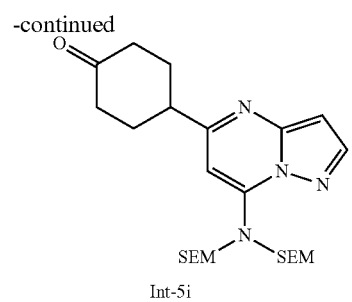

4-(7-aminopyrazolo[1,5-a]pyrimidin-5-yl)cyclohexanone (Int-5h, 5.12 mmol, 1.18 g) was taken up in DCM (15 mL). To this solution was added N,N'-diisopropylethylamine (17.94 mmol, 3.13 mL). The resulting solution was stirred at room temperature while 2-(trimethylsilyl)ethoxymethyl chloride (SEM-Cl, 17.94 mL, 3.17 mL) in DCM (5 mL) was added dropwise. After the addition was completed, the reaction mixture was stirred at 50° C. for 10 minutes. The solvent was removed in vacuo and the residue was purified on a silica gel column (0% to 60% ethyl acetate in hexanes gradient) to yield 4-(7-(bis((2-(trimethylsilyl)ethoxy)methyl)amino)-pyrazolo[1,5-a]pyrimidin-5-yl)cyclohexanone (Int-50 (1.87 g, 74% yield) as a pale yellow oil.

Step I—Synthesis of Ethyl 2-(4-(7-(bis((2-(trimethylsilyl)ethoxy)methyl)amino)pyrazolo[1,5-a]pyrimidin-5-yl)cyclohexylidene)acetate (Int-5j)

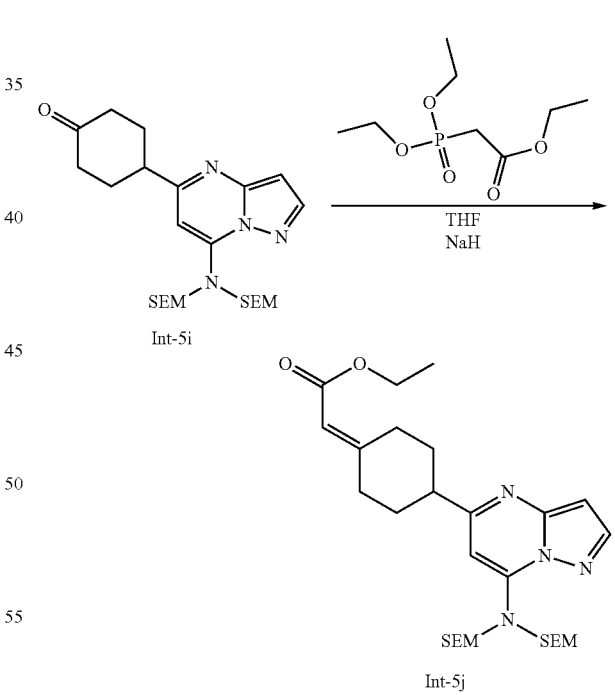

To a 20 mL scintillation vial containing 5 mL THF was charged sodium hydride (60% w/w in mineral oil, 448 μmol, 18 mg). This suspension was broken up via sonication. Triethyl phosphonoacetate (448 μmol, 89.3 μL) in THF (2 mL) was added dropwise. The resulting solution was stirred at room temperature for 10 minutes. To this mixture was slowly added a solution of 4-(7-(bis((2-(trimethylsilyl)ethoxy)methyl)amino)pyrazolo[1,5-a]pyrimidin-5-yl)cyclohexanone (Int-5i, 408 μmol, 200 mg) in THF (2 mL). The resulting solution was stirred at 18 hours at room temperature. After 18 hours, the solution was diluted with DCM (25 mL) and washed with H₂O. The aqueous phase was extracted with DCM (x2) and the combined organic layers were dried over Na₂SO₄. The solvent was removed in vacuo to yield ethyl 2-(4-(7-(bis((2-(trimethylsilyl)ethoxy)methyl)amino)pyrazolo[1,5-a]pyrimidin-5-yl)cyclohexylidene)acetate (Int-5j) (222 mg, 97% yield) as a pale yellow oil.

Step J—Synthesis of ethyl 2-(4-(7-(bis((2-(trimethylsilyl)ethoxy)methyl)amino)pyrazolo[1,5-a]pyrimidin-5-yl)cyclohexyl)acetate (Int-5k)

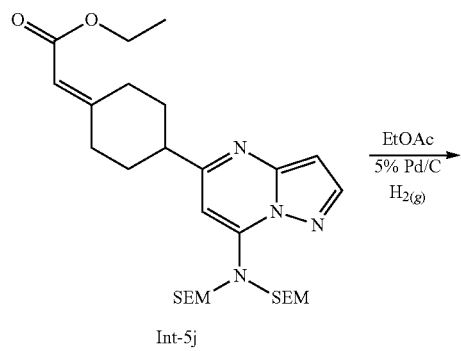

Int-5j ylsilyl)ethoxy)methyl)amino)pyrazolo[1,5-a]pyrimidin-5-yl)cyclohexyl)acetate (Int-5k) (761 mg, 1.35 mmol, 95% yield) as a pale yellow oil.

Step K—Synthesis of ethyl 2-(4-(7-(bis((2-(trimethylsilyl)ethoxy)methyl)amino)-3-iodopyrazolo[1,5-a]pyrimidin-5-yl)cyclohexyl)acetate (Int-5l)

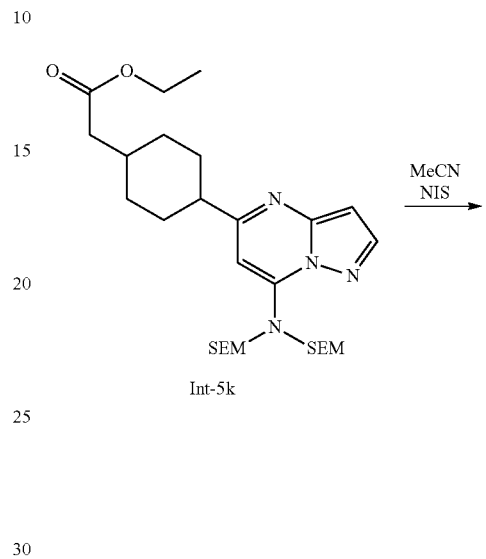

Int-5k

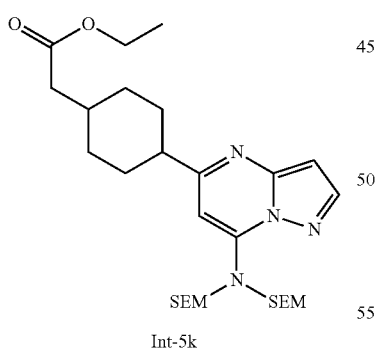

Int-5k

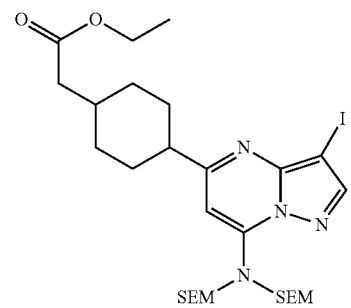

Int-5l

To a 50 mL round-bottom flask was charged ethyl 2-(4-(7-(bis((2-(trimethylsilyl)ethoxy)methyl)amino)pyrazolo[1,5-a]pyrimidin-5-yl)cyclohexylidene)acetate (Int-5j, 800 mg, 1.43 mmol) and ethyl acetate (15 mL). The flask was flushed with argon and 5% palladium on carbon (100 mg) was added. The flask was sealed and degassed under vacuum. Hydrogen gas was then added via balloon. The reaction was stirred under a hydrogen atmosphere 18 hours. The reaction was then filtered through celite to yield ethyl 2-(4-(7-(bis((2-(trimeth- To a 50 mL round-bottom flask was charged ethyl 2-(4-(7-(bis((2-(trimethylsilyl)ethoxy)methyl)amino)pyrazolo[1,5-a]pyrimidin-5-yl)cyclohexyl)acetate (Int-5k, 381 mg, 0.68 mmol) and acetonitrile (10 mL). To this solution was added N-iodosuccinimide (167 mg, 0.74 mmol). The resulting solution was stirred at room temperature for 18 hours. The reaction was reduced in vacuo and the concentrated oil was purified via silica gel chromatography (0% to 30% ethyl acetate in hexanes gradient) to yield ethyl 2-(4-(7-(bis((2-(trimethylsilyl)ethoxy)methyl)amino)-3'-iodopyrazolo[1,5-a]pyrimidin-5-yl)cyclohexyl)acetate (Int-5l) (335 mg, 0.49 mmol, 72% yield) as a clear oil.

Step L—Synthesis of Ethyl 2-(4-(7-(bis((2-(trimethylsilyl)ethoxy)methyl)amino)-3-(6-chloropyridin-3-yl)pyrazolo[1,5-a]pyrimidin-5-yl)cyclohexyl)acetate (Int-5m)

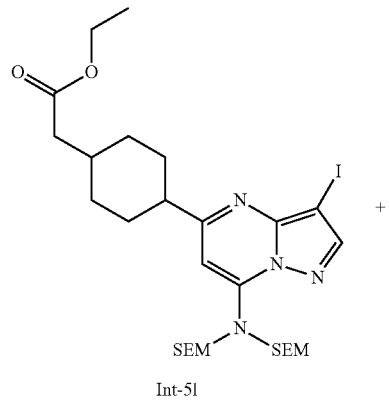

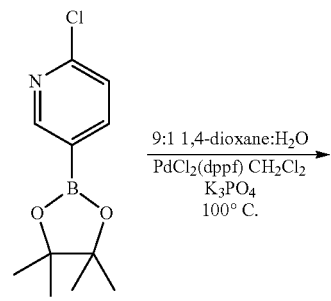

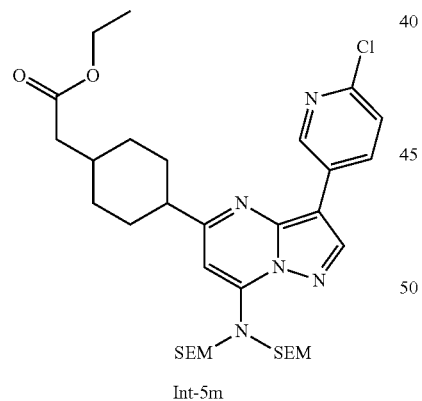

To a 10-20 mL microwave flask was added ethyl 2-(4-(7-(bis((2-(trimethylsilyl)ethoxy)methyl)amino)-3-iodopyrazolo[1,5-a]pyrimidin-5-yl)cyclohexyl)acetate (Int-5l, 1.41 g, 2.05 mmol), 6-chloropyridine-3-boronic acid pinacol ester (514 mg, 2.15 mmol), $K_3PO_4$ (1.31 g, 6.15 mmol), $PdCl_2$(dppf)·$CH_2O_2$ (167 mg, 0.21 mmol) and 9:1 1,4-dioxane:$H_2O$ (10 mL). The flask was flushed with argon and sealed. The reaction was stirred overnight at 100° C. After 18 hours, the reaction was diluted with DCM and washed with $H_2O$. The aqueous was extracted with DCM (x2) and the combined organic layers were dried over $Na_2SO_4$. The solvent was reduced in vacuo and the title compound was purified via silica gel chromatography.

Step M—Synthesis of Ethyl 2-(4-(7-(bis((2-(trimethylsilyl)ethoxy)methyl)amino)-3-(6-phenylpyridin-3-yl)pyrazolo[1,5-a]pyrimidin-5-yl)cyclohexyl)acetate (Int-5n)

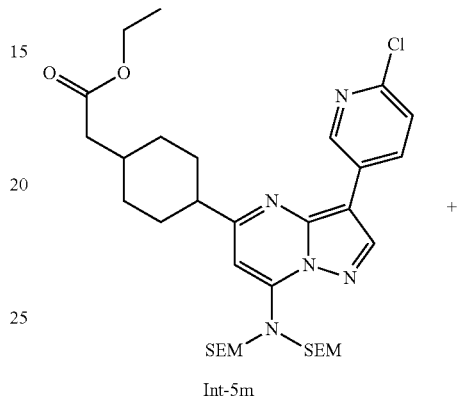

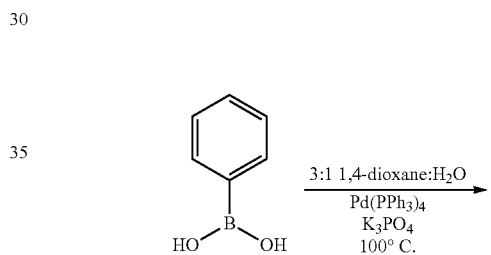

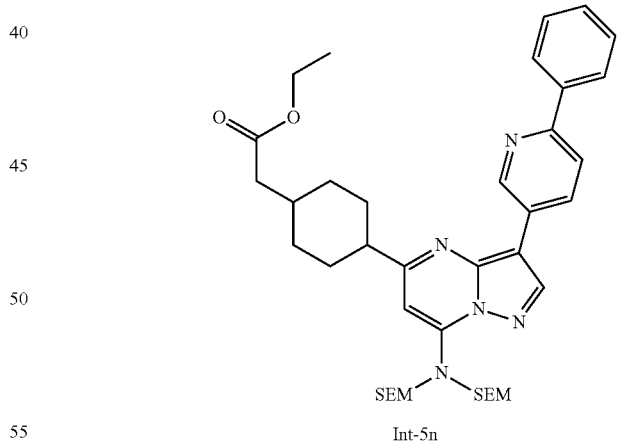

To 10-20 mL microwave flask was added ethyl 2-(4-(7-(bis((2-(trimethylsilyl)ethoxy)methyl)amino)-3-(6-chloropyridin-3-yl)pyrazolo[1,5-a]pyrimidin-5-yl)cyclohexyl)acetate (Int-5m, 500 mg, 741 μmol), phenylboronic acid (181 mg, 1.48 mmol), $K_3PO_4$ (314 mg, 1.48 mmol), Pd(PPh$_3$)$_4$ (86 mg, 74 mol) and 3:1 1,4-dioxane:$H_2O$ (8 mL). The flask was flushed with argon and sealed. The reaction was stirred in a microwave at 150° C. for 30 minutes. After 30 minutes, the reaction was diluted with DCM and washed with $H_2O$. The aqueous was extracted with DCM (x2) and the combined organic layers were dried over Na$_2$SO$_4$. The solvent was reduced in vacuo and the title compound was purified via silica gel chromatography.

Step N—Synthesis of Ethyl 2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)acetate (Int-5o)

Step O—Synthesis of ethyl 2-(4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)cyclohexyl)acetate (Int-5p)

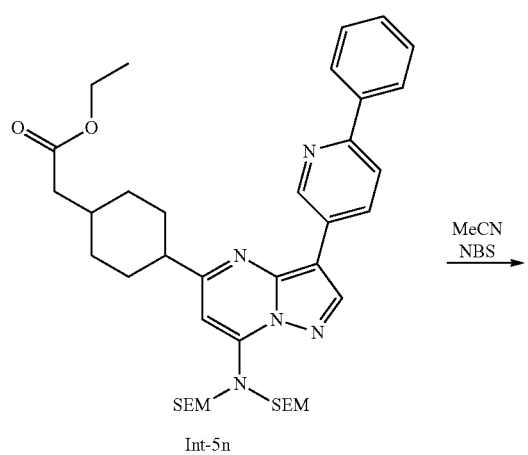

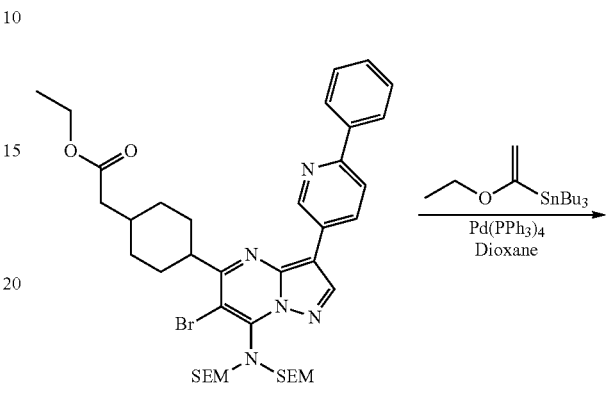

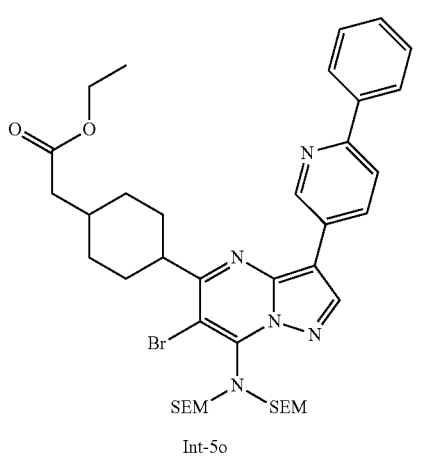

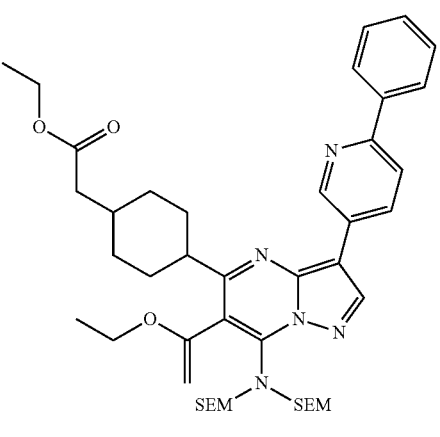

To a solution of ethyl 2-(4-(7-(bis((2-(trimethylsilyl)ethoxy)methyl)amino)-3-(6-phenylpyridin-3-yl)pyrazolo[1,5-a]pyrimidin-5-yl)cyclohexyl)acetate (Int-5n, 512 mg, 715 μmol) in acetonitrile (15 mL) was added N-bromosuccinimide (153 mg, 858 μmol). The resulting solution was allowed to stir at room temperature for 18 hours. After 18 hours, the solvent was reduced in vacuo and the title compound was purified via silica gel chromatography.

By essentially the same procedure as the synthesis of ethyl 4-((7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)methyl)cyclohexanecarboxylate (Int-4n, Step M of Example 4), ethyl 2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)acetate (Int-5o) was converted to ethyl 2-(4-(7-(bis((2-(trimethylsilyl)ethoxy)

methyl)amino)-6-(1-ethoxyvinyl)-3-(6-phenylpyridin-3-yl) pyrazolo[1,5-a]pyrimidin-5-yl)cyclohexyl)acetate (Int-5p).

Step P—Synthesis of 2-(4-(3-methyl-6-(6-phenylpyridin-3-yl)-1H-dipyrazolo[1,5-a:4',3'-e]pyrimidin-4-yl)cyclohexyl)acetic acid (Compound 22)

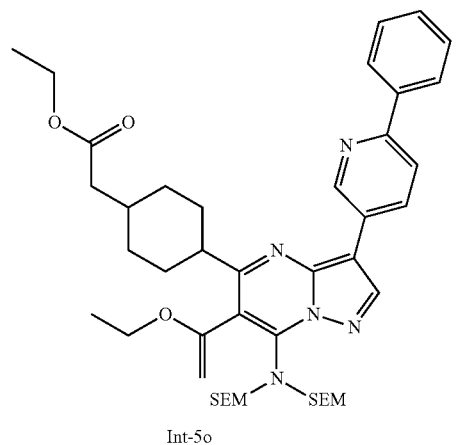

Int-5o

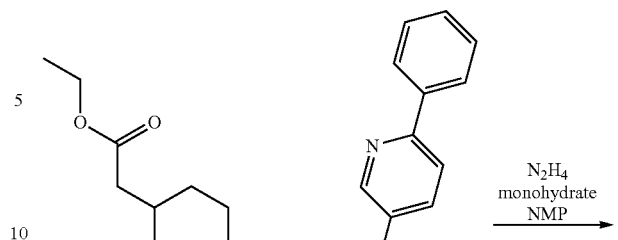

Int-5p

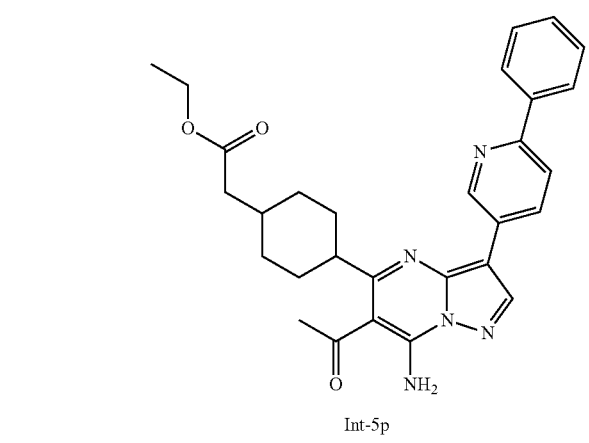

Int-5p

Int-5q

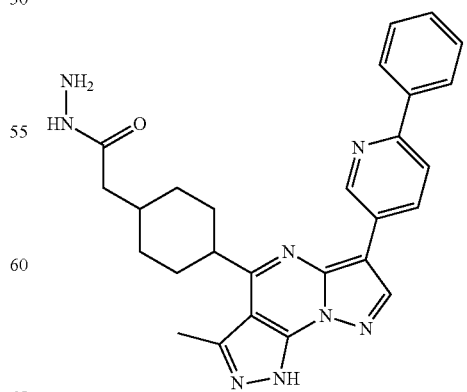

Int-5r

To a 20 mL scintillation vial containing ethyl 4-((7-(bis((2-(trimethylsilyl)ethoxy)methyl)amino)-6-(1-ethoxy methyl)-3-(6-phenylpyridin-3-yl)pyrazolo[1,5-a]pyrimidin-5-yl)methyl)cyclohexanecarboxylate (Int-5o, 113 mg, 0.144 mmol) was added EtOH (2 mL) followed by 4N HCl (aq). The resulting cloudy suspension was stirred at room temperature 1 hour, at which time the solution was now homogenous. The solvent was removed in vacuo and excess solvent was pumped off on high vacuum. The compound was taken on without further purification.

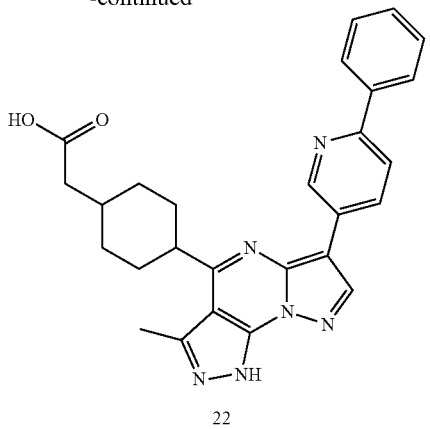

22

By essentially the same procedure as the synthesis of Compound 5 given in Step O of Example 4, Int-5p was converted to 2-(4-(3-methyl-6-(6-phenylpyridin-3-yl)-1H-dipyrazolo[1,5-a:4',3'-e]pyrimidin-4-yl)cyclohexyl)acetic acid (22). The compound was purified via reverse-phase preparatory HPLC to 2-(4-(3-methyl-6-(6-phenylpyridin-3-yl)-1H-dipyrazolo[1,5-a:4',3'-e]pyrimidin-4-yl)cyclohexyl)acetic acid (M+H=467.34, retention time=3.58 min).

Example 6

Preparation of Compounds 3, 2, and 4

Step A—Synthesis of Ethyl 8-methyl-1,4-dioxaspiro[4.5]decane-8-carboxylate (Int-6a)

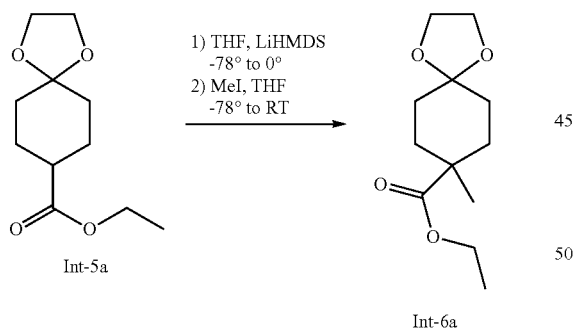

To a 100 mL round-bottom flask was charged THF (8 mL). The flask was flushed with argon, sealed, and fitted to balloon containing argon. The flask was cooled to −78° C. in dry ice/IPA bath. To this solution was added ethyl 1,4-dioxaspiro[4.5]decane-8-carboxylate (Int-5a, 2.28 g, 10.64 mmol) in 8 mL THF. The resulting solution was allowed to remain at −78° C. while LiHMDS (1.0 M in THF, 12.34 mmol, 12.34 mL) was added dropwise. Upon completion of addition, the solution was allowed to warm to 0° C. in ice bath. The reaction was stirred at 0° C. for one hour, at which point it was cooled back to −78° C. in dry ice/IPA bath. At this point, iodomethane (750 µL, 12.02 mmol) in THF (8 mL) was added dropwise. The reaction was allowed to gradually warm to room temperature as it was stirred overnight. After 18 hours, the reaction was quenched with sat NH$_4$Cl$_{(aq)}$ and extracted with Et$_2$O (x2). The combined organic extracts were washed with H$_2$O (x1), saturated brine (x1), and dried over Na$_2$SO$_4$ and the residue were purified via silica gel chromatography to yield the title compound as a clear oil. Yield=1.44 g.

Step B—Synthesis of ethyl 1-methyl-4-oxocyclohexanecarboxylate (Int-6b)

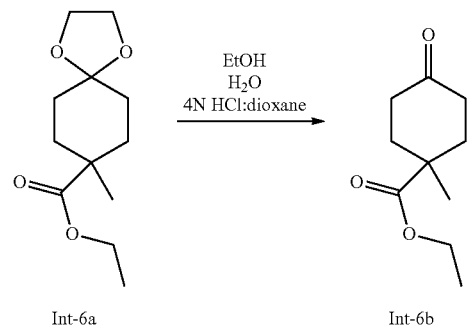 [SMILES: CCOC(=O)C1(C)CCC2(CC1)OCCO2 ; CCOC(=O)C1(C)CCC(=O)CC1]

In a 50 mL round-bottom flask was mixed with ethyl 8-methyl-1,4-dioxaspiro[4.5]decane-8-carboxylate (Int-6a, 1.99 g, 8.72 mmol), EtOH (10 mL), H$_2$O (5 mL), and 4N HCl in 1,4-dioxane (5 mL). The resulting solution was stirred at room temperature for 64 hours. At this time, the solvent was removed in vacuo and the residue was taken up in DCM. The suspension was washed with saturated NaHCO$_{3(aq)}$ and the organic layer was dried over Na$_2$SO$_4$. The resulting product was taken on without further purification. Yield=1.00 g.

Step C—Synthesis of ethyl 1-methyl-4-((3-methyl-6-(6-phenylpyridin-3-yl)-1H-dipyrazolo[1,5-a:4',3'-e]pyrimidin-4-yl)methyl)cyclohexanecarboxylate (Int-6c)

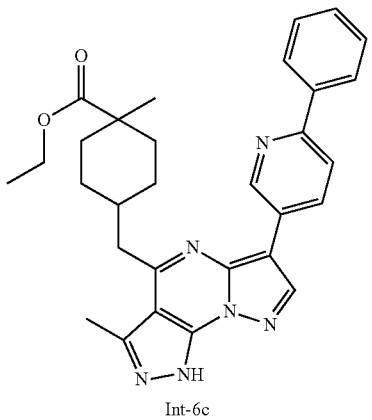 [SMILES: CCOC(=O)C1(C)CCC(Cc2nc3c(-c4ccc(-c5ccccc5)nc4)cnn3c3[nH]nc(C)c23)CC1]

Int-6c

Ethyl 1-methyl-4-oxocyclohexanecarboxylate (Int-6b) was converted into Int-6c in the same manner as ethyl 4-oxocyclohexanecarboxylate was converted into Int-4o in Steps A-N of Example 4.

Step D—Synthesis of 1-methyl-4-((3-methyl-6-(6-phenylpyridin-3-yl)-1H-dipyrazolo[1,5-a:4',3'-e]pyrimidin-4-yl)methyl)cyclohexanecarboxylic acid (Compound 3)

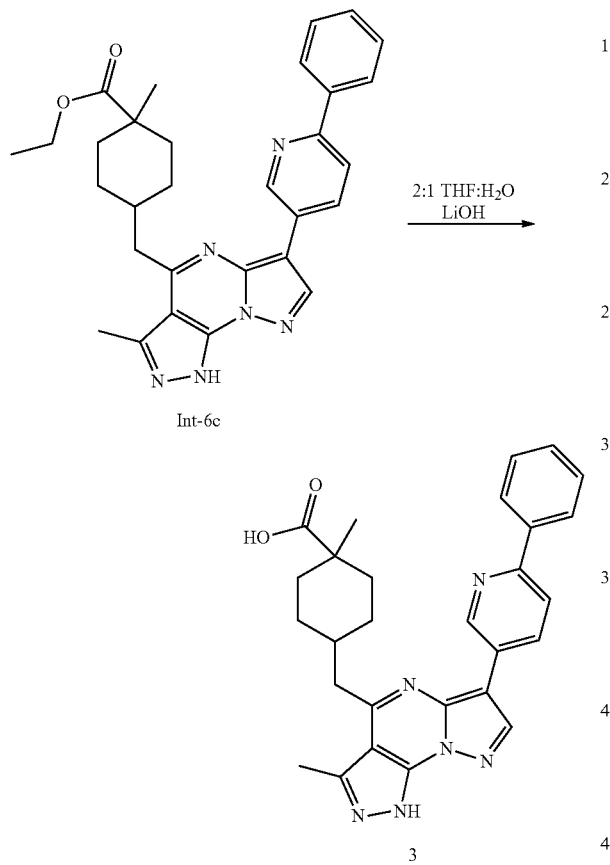

To a 20 mL scintillation vial was charged ethyl 1-methyl-4-((3-methyl-6-(6-phenylpyridin-3-yl)-1H-dipyrazolo[1,5-a:4',3'-e]pyrimidin-4-yl)methyl)cyclohexanecarboxylate (Int-6c, 0.03 mmol). To this residue was added 2:1 THF:H$_2$O (1.5 mL) and LiOH.H$_2$O (20 mg). The resulting solution was stirred at 80° C. for 4 days. After 4 days, the reaction was brought to pH 3 with 1N HCl$_{(aq)}$. The reaction was reduced in vacuo and the residue was purified via reverse-phase preparatory HPLC to 1-methyl-4-((3-methyl-6-(6-phenylpyridin-3-yl)-1H-dipyrazolo[1,5-a:4',3'-e]pyrimidin-4-yl)methyl)cyclohexanecarboxylic acid (3). (M+H=481.27, retention time=4.01 min).

Preparation of Compounds 2 and 4

By similar procedures detailed above for the preparation of compound 3, compounds 2 and 4 were prepared. LC/MS data for compounds 2 and 4 are set forth below.

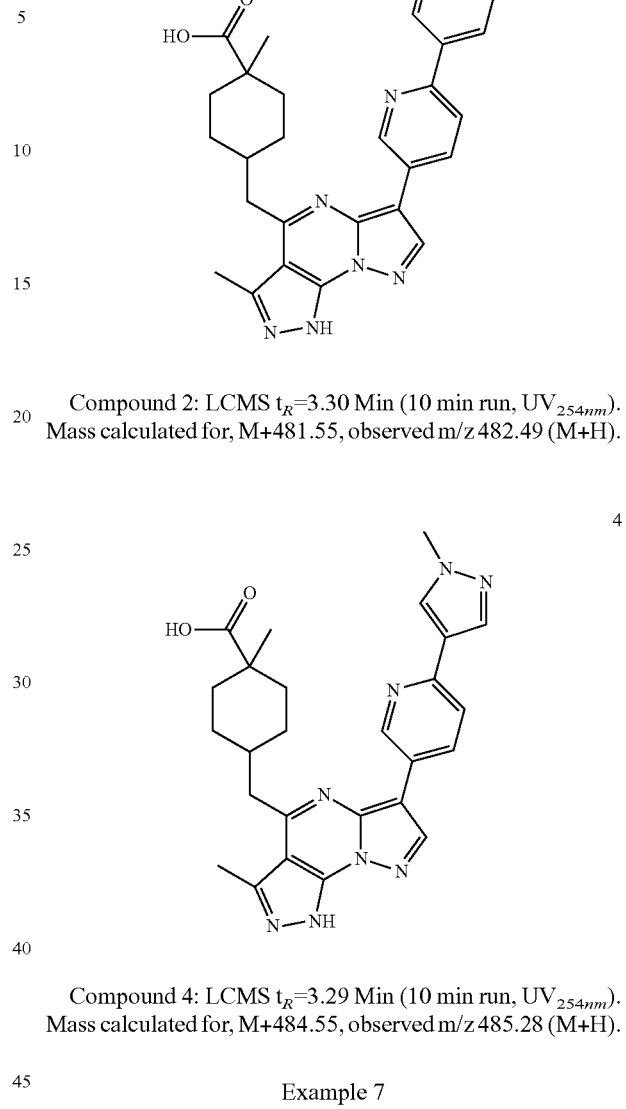

Compound 2: LCMS t$_R$=3.30 Min (10 min run, UV$_{254nm}$). Mass calculated for, M+481.55, observed m/z 482.49 (M+H).

Compound 4: LCMS t$_R$=3.29 Min (10 min run, UV$_{254nm}$). Mass calculated for, M+484.55, observed m/z 485.28 (M+H).

Example 7

Preparation of Compounds 8 and 7

Preparation of Compound 8

Step A—Synthesis of 4-(2-Ethoxycarbonyl-acetyl)-cyclohexanecarboxylic acid methyl ester (Int-7a)

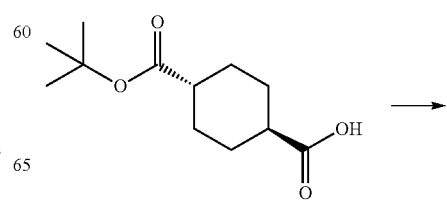

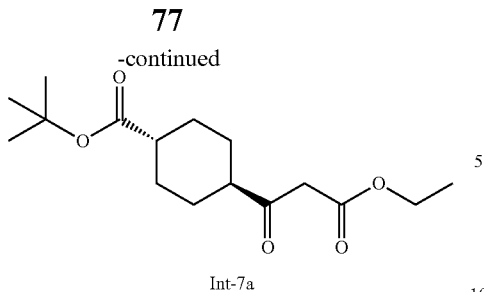

Int-7a

Cyclohexane-1,4-dicarboxylic acid mono-t-butyl ester (26.9 mmol, 5.0 g) and N,N'-carbonyldiimidazole (33.6 mmol, 5.44 g) in anhydrous THF (80 mL) were stirred 16 h at room temperature under argon. In a separate, sealed and argon-flushed flask, LiHMDS (1.0 M in THF, 56.5 ml) was added to 40 mL anhydrous THF stirring at −78° C. To this solution was added dropwise anhydrous ethyl acetate (57.8 mmol, 5.65 mL). This solution was allowed to stir at −78° C. for 1 hour prior to dropwise addition of original CDI/acid solution that had been stirring overnight. The reaction mixture was allowed to stir and warm to room temperature overnight. The reaction was then quenched with saturated $NH_4Cl_{(aq)}$ (200 mL) and extracted with $Et_2O$ (100×2). The combined organics were then washed with water, saturated brine, and dried over $Na_2SO_4$. The solvent was removed in vacuo and the crude residue (8.5 g) was used in the next step without further purification.

Step B—Synthesis of 4-(7-Hydroxy-pyrazolo[1,5-a]pyrimidin-5-yl)-cyclohexanecarboxylic acid -t-butyl ester (Int-7b)

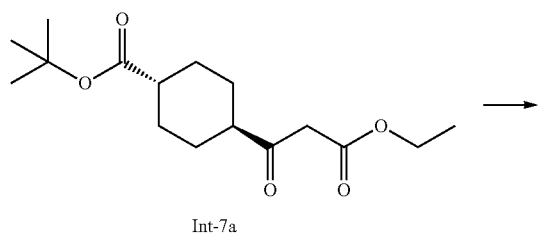

Int-7a 4-(2-Ethoxycarbonyl-acetyl)-cyclohexanecarboxylic acid t-butyl ester (8.5 g) and 3-amino-1H-pyrazole (Int-7a, 26.5 mmol, 2.2 g) were mixed and heated neat at 100° C. for 16 hours. The resulting residue was dissolved in dichloromethane (100 mL) and concentrated in vacuo to remove water formed during cyclization. This solid was taken forward without further purification. LC-MS: 318 [M+H].

Step C—Synthesis of 4-(7-Chloro-pyrazolo[1,5-a]pyrimidin-5-yl)-cyclohexanecarboxylic acid t-butyl ester (Int-7c)

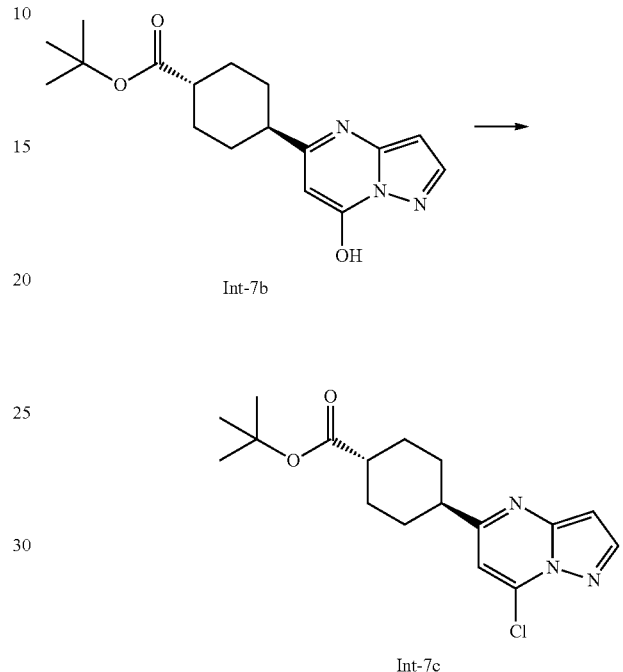

4-(7-Hydroxy-pyrazolo[1,5-a]pyrimidin-5-yl)-cyclohexanecarboxylic acid t-butyl ester (Int-7b, 10.6 g), N,N-dimethylaniline (15.0 ml) and $POCl_3$ (120 mL) were mixed and stirred at room temperature for 18 hours. The solution was reduced in vacuo and cooled to 0° C. in ice bath. The reaction was then quenched with sat. $NaHCO_{3(aq)}$ and extracted with DCM (100 mL×3). The combined organics were dried with $Na_2SO_4$ and the solvent was removed in vacuo. The resulting oil was purified via silica gel column on 20% to 100% ethyl acetate in hexanes gradient to yield the title compound (2.5 g, 32% over three steps). LC-MS: 336 [M+H].

Step D—Synthesis of 4-(7-Amino-pyrazolo[1,5-a]pyrimidin-5-yl)-cyclohexanecarboxylic acid t-butyl ester (Int-7d)

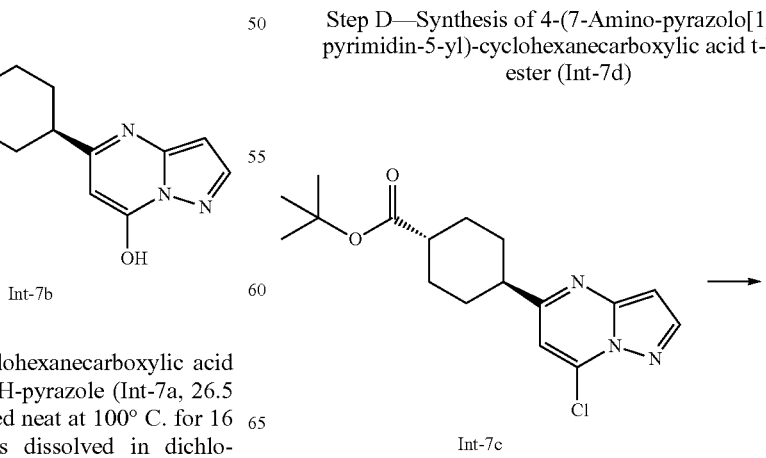

-continued

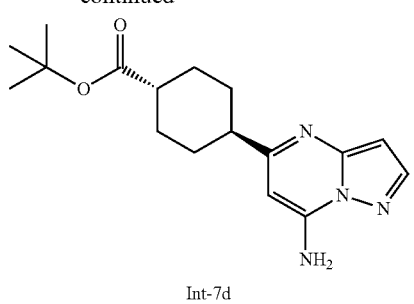

Int-7d 4-(7-Chloro-pyrazolo[1,5-a]pyrimidin-5-yl)-cyclohexanecarboxylic acid methyl ester (Int-7c, 2.5 g, 8.51 mmol) was dissolved in 15 mL ~7N ammonia in methanol in a sealed vessel. The reaction mixture was heated at 80° C. for 16 hours. After 16 hours, the reaction mixture was cooled to room temperature and concentrated in vacuo to yield a brown solid (2.58 g). The title compound was used in the next step without further purification. LC-MS: 317 [M+H].

Step E—Synthesis of 4-{7-[Bis-(2-trimethylsilanyl-ethoxymethyl)-amino]-pyrazolo[1,5-a]pyrimidin-5-yl}-cyclohexanecarboxylic acid methyl ester (Int-7e)

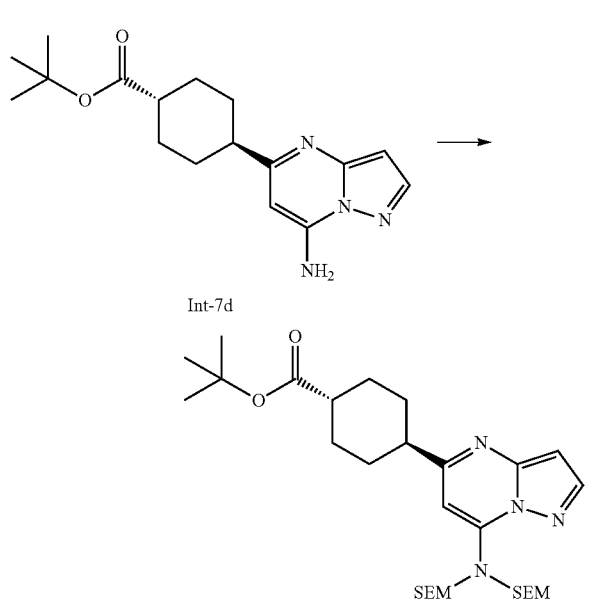

Int-7d

Int-7e 4-(7-Amino-pyrazolo[1,5-a]pyrimidin-5-yl)-cyclohexanecarboxylic acid methyl ester (Int-7d, 2.58 g, 9.4 mmol) was dissolved in 1,2-dichloroethane (20 mL). To this solution was added N,N'-diisopropylethylamine (65.8 mmol, 11.5 mL). The resulting solution was stirred at room temperature while 2-(trimethylsilyl)ethoxymethyl chloride (SEM-Cl, 5.8 mL, 33.0 mmol) was added dropwise. After the addition was completed, the reaction mixture was stirred at 90° C. for 2 h. The solvent was removed in vacuo and the residue was purified on a silica gel column (0% to 60% ethyl acetate in hexanes gradient) to yield the title compound (2.05 g, 41% yield over two steps) as pale yellow oil. LC-MS: 577 [M+H].

Step F—Synthesis of 4-{7-[Bis-(2-trimethylsilanyl-ethoxymethyl)-amino]-3-iodo-pyrazolo[1,5-a]pyrimidin-5-yl}-cyclohexanecarboxylic acid methyl ester (Int-7f)

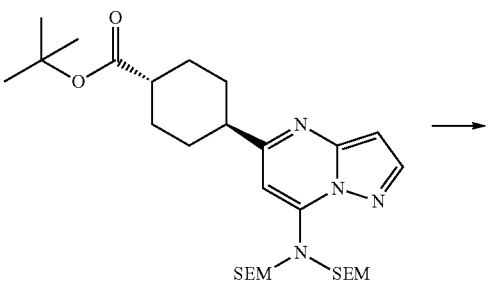

Int-7e

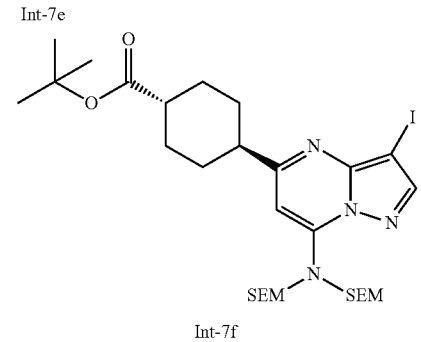

Int-7f

N-Iodosuccinimide (811 mg, 3.6 mmol) was added into a solution of 4-{7-[bis-(2-trimethylsilanyl-ethoxymethyl)-amino]-pyrazolo[1,5-a]pyrimidin-5-yl}-cyclohexanecarboxylic acid methyl ester (Int-7e, 1.75 g, 3.27 mmol) in acetonitrile (25 mL). The resulting reaction mixture was stirred at room temperature for 16 hours. The reaction mixture was concentrated in vacuo and purified via silica gel chromatography (0% to 30% ethyl acetate in hexanes gradient) to yield the title compound (1.79 g, 82.8% yield) at clear oil. LC-MS: 703 [M+H].

Step G—Synthesis of (1R,4R)-tert-Butyl 4-(7-(bis((2-(trimethylsilyl)ethoxy)methyl)amino)-3-(6-chloropyridin-3-yl)pyrazolo[1,5-a]pyrimidin-5-yl)cyclohexanecarboxylate (Int-7g)

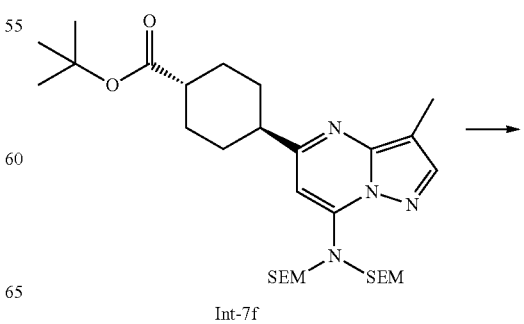

Int-7f

-continued

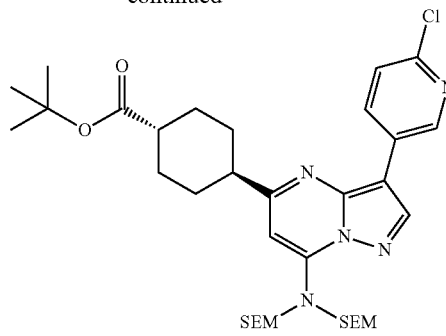
Int-7g

6-Chloropyridine-3-boronic acid pinacol ester (35.5 mmol, 8.52 g), $K_3PO_4$ (92.7 mmol, 19.6 g), and $PdCl_2(dppf)$ $\cdot CH_2Cl_2$ (3.09 mmol, 2.52 g) was added to a solution of (1R,4R)-tert-butyl 4-(7-(bis((2-(trimethylsilyl)ethoxy)methyl)amino)-3-iodopyrazolo[1,5-a]pyrimidin-5-yl)cyclohexanecarboxylate (Int-7f, 30.9 mmol, 21.7 g) in dioxane (200 ml). To this suspension was added distilled $H_2O$ (20 mL). The resulting solution was stirred at 90° C. under argon for 18 hours. The reaction was cooled to room temperature, diluted with ethyl acetate (200 ml) and washed with water (100 ml). The aqueous phase was extracted with ethyl acetate (200 ml). The combined organics are dried over $Na_2SO_4$ and the residue purified via silica gel chromatography (0% to 60% ethyl acetate in hexanes gradient) to yield the title compound (18.42 g, 86.7% yield) as yellow oil. LC-MS: 688 [M+H].

Step H—Preparation of (1R,4R)-tert-Butyl 4-(7-(bis((2-(trimethylsilyl)ethoxy)methyl)amino)-3-(6-phenylpyridin-3-yl)pyrazolo[1,5-a]pyrimidin-5-yl)cyclohexanecarboxylate (Int-7h)

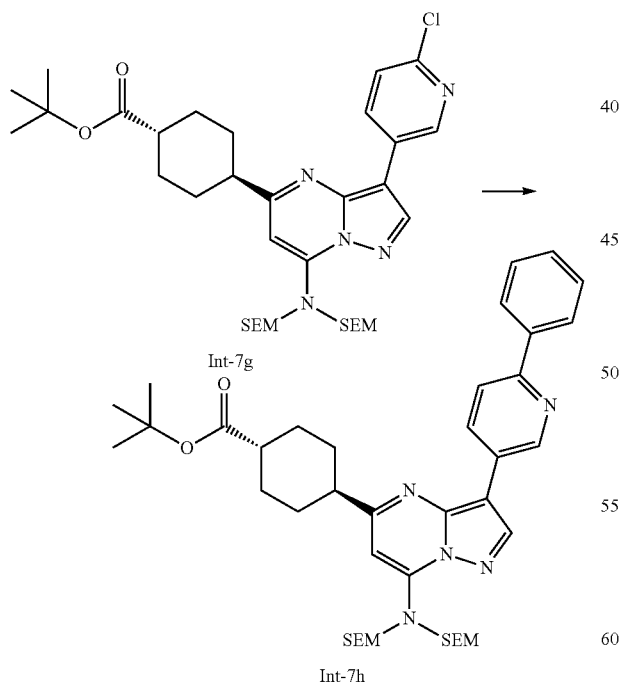

Phenylboronic acid (53.6 mmol, 6.54 g), $K_3PO_4$ (80.4 mmol, 17 g), and $Pd(PPh_3)_4$ (2.7 mmol, 3.1 g) was added to a solution of (1R,4R)-tert-butyl 4-(7-(bis((2-(trimethylsilyl)ethoxy)methyl)amino)-3-(6-chloropyridin-3-yl)pyrazolo[1,5-a]pyrimidin-5-yl)cyclohexanecarboxylate (Int-7g, 26.8 mmol, 18.4 g) in dioxane (120 mL). To this suspension was added distilled $H_2O$ (30 mL). The resulting solution is stirred at 100° C. under argon for 18 hours. The reaction was cooled to room temperature, diluted with ethyl acetate (200 ml) and washed with water (100 ml). The aqueous phase was extracted with ethyl acetate (200 ml). The combined organics were dried over $Na_2SO_4$ and the residue purified via silica gel chromatography (0% to 60% ethyl acetate in hexanes gradient) to yield the title compound (16.1 g, 82% yield) as yellow oil. LC-MS: 730 [M+H].

Step I—Preparation of (1R,4R)-tert-Butyl 4-(7-(bis((2-(trimethylsilyl)ethoxy)methyl)amino)-6-bromo-3-(6-phenylpyridin-3-yl)pyrazolo[1,5-a]pyrimidin-5-yl)cyclohexanecarboxylate (Int-7i)

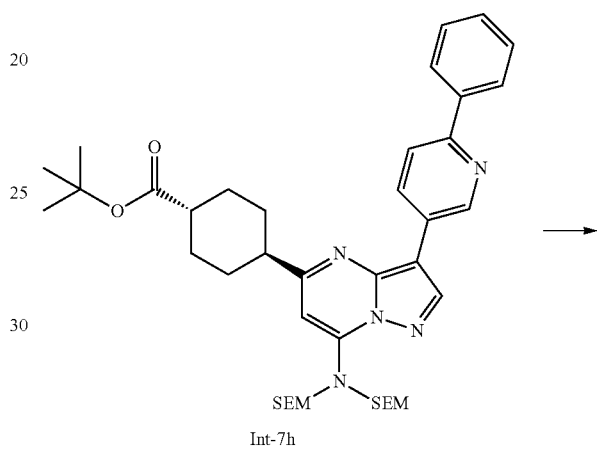

N-bromosuccinimide (349 mg, 1.96 mmol) was added to a solution of (1R,4R)-tert-butyl 4-(7-(bis((2-(trimethylsilyl)ethoxy)methyl)amino)-3-(6-phenylpyridin-3-yl)pyrazolo[1,5-a]pyrimidin-5-yl)cyclohexanecarboxylate (Int-7h, 1.3 g, 1.78 mmol) in acetonitrile:dichloromethane (20 mL in 1:1 ratio). The resulting solution was stirred at room temperature for 3 hours. The reaction was reduced in vacuo and the resulting oil was then purified via silica gel chromatography (0% to 30% ethyl acetate in hexanes gradient) to yield the title compound (1.36 g, 94% yield) as a yellow oil. LC-MS: 808 [M+H].

Step J—Preparation of (1R,4R)-tert-Butyl 4-(7-(bis ((2-(trimethylsilyl)ethoxy)methyl)amino)-6-(1-ethoxyvinyl)-3-(6-phenylpyridin-3-yl)pyrazolo[1,5-a]pyrimidin-5-yl)cyclohexanecarboxylate (Int-7j)

anes gradient) to yield the title compound (1.3 g, 96% yield) as yellow oil. LC-MS: 800 [M+H].

Step K—Preparation of (1R,4R)-4-(6-Acetyl-7-amino-3-(6-phenylpyridin-3-yl)pyrazolo[1,5-a]pyrimidin-5-yl)cyclohexanecarboxylic acid (Int-7k)

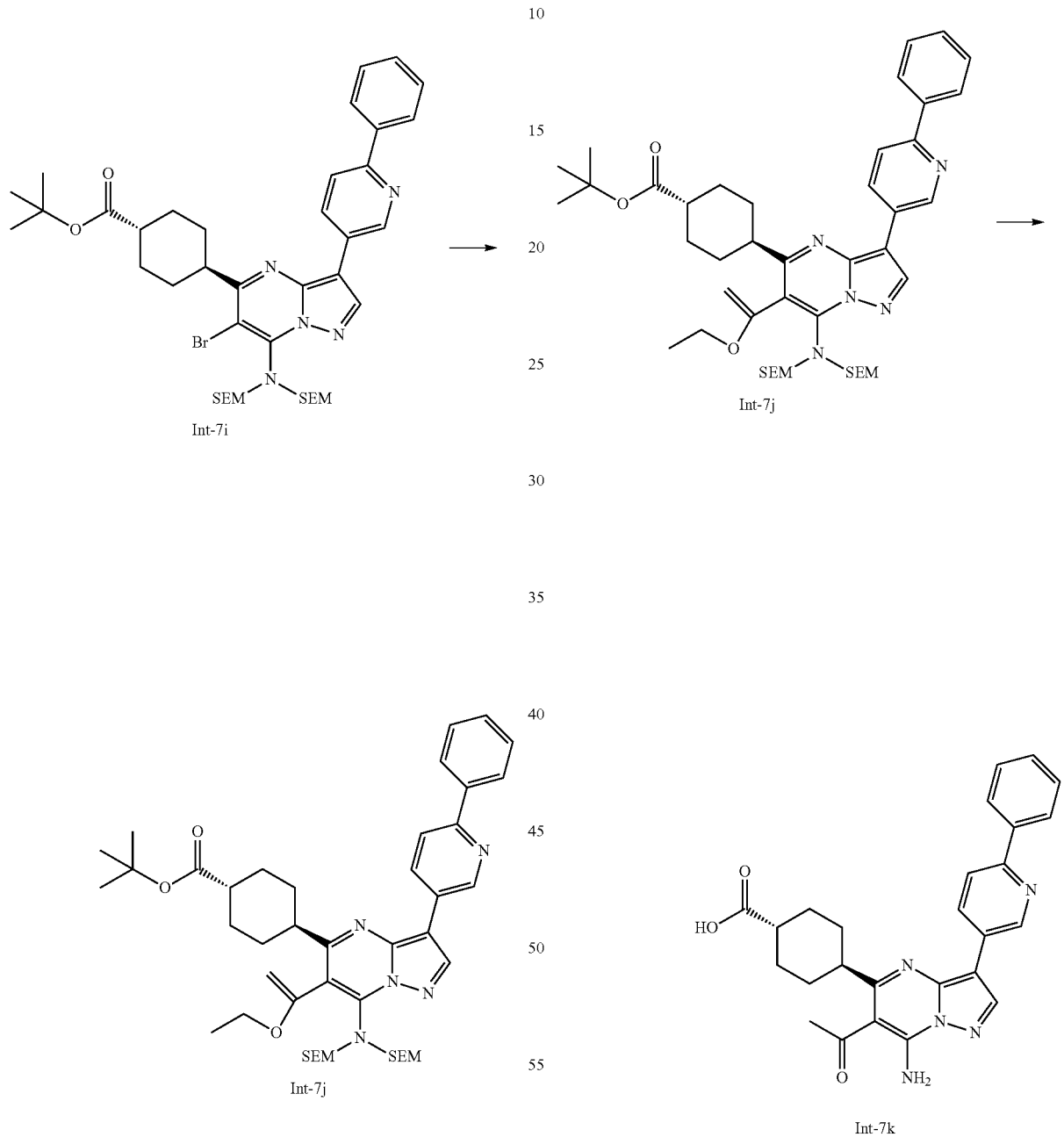

Tributyl (1-ethoxyvinyl)tin (1.7 mL, 5.05 mmol) and Pd(PPh$_3$)$_4$ (194 mg, 0.168 mmol) was added to a solution of (1R,4R)-tert-butyl 4-(7-(bis((2-(trimethylsilyl)ethoxy)methyl)amino)-6-bromo-3-(6-phenylpyridin-3-yl)pyrazolo[1,5-a]pyrimidin-5-yl)cyclohexanecarboxylate (Int-7i, 1.36 g, 1.68 mmol) in 1,4-dioxane (10 mL). The reaction was heated to 100° C. under argon for 18 hours. After 18 hours, the solvent was removed in vacuo and the residue was purified via silica gel chromatography (0% to 30% ethyl acetate in hex- (1R,4R)-tert-Butyl 4-(7-(bis((2-(trimethylsilyl)ethoxy) methyl)amino)-6-(1-ethoxyvinyl)-3-(6-phenylpyridin-3-yl) pyrazolo[1,5-a]pyrimidin-5-yl)cyclohexanecarboxylate (Int-7j, 1.3 g, 0.16 mmol) in 1,4-dioxane (8 mL) was treated with 4N HCl$_{(aq)}$ (8 mL). The resulting solution was stirred at 65° C. for 3 hours. The reaction solution was filtered, the yellow solid was washed with acetonitrile:water (1:1) and was dried in vacuo to afford the title compound: Mass calculated for, M+H 456.20, observed 456.20.

Step L—Preparation of (1R,4R)-4-(3-methyl-6-(6-phenylpyridin-3-yl)-1H-dipyrazolo[1,5-a:4',3'-e]pyrimidin-4-yl)cyclohexanecarboxylic acid (Compound 8)

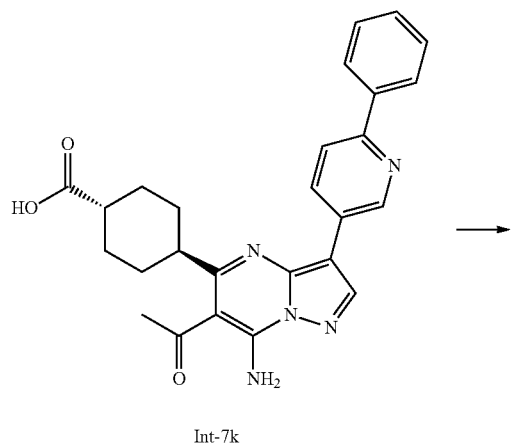

Int-7k

To a 20 mL scintillation vial was charged (1R,4R)-4-(6-acetyl-7-amino-3-(6-phenylpyridin-3-yl)pyrazolo[1,5-a]pyrimidin-5-yl)cyclohexanecarboxylic acid (Int-7k, 50 mg, 0.11 mmol). To this vial was added NMP (0.5 mL) followed by hydrazine monohydrate (1 mL). The reaction was stirred at room temperature for 3 hours. The excess hydrazine monohydrate was removed in vacuo and the residue transferred into 2-5 mL microwave vessel. The vial was sealed and heated to 180° C. for 30 minutes in microwave. The NMP was reduced in vacuo using chlorobenzene as a cosolvent. The residue was purified via reverse-phase preparatory HPLC to yield the title compound (cis:trans=1:9): LCMS $t_R$=3.62 Min (10 min run, $UV_{254nm}$). Mass calculated for, M+H 453.20, observed 453.20.

Preparation of Compound 7

By a similar procedure detailed above for the preparation of compound 8, compound 7 was prepared. LC/MS data for compound 7 is set forth below.

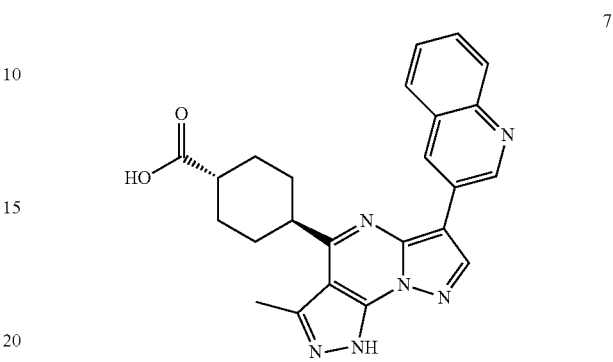

Compound 7: LCMS $t_R$=3.13 Min (10 min run, $UV_{254nm}$). Mass calculated for, M+H 427.18, observed m/z 427.18 (M+H).

Example 8

Preparation of Compound 26

Step A—Synthesis of 3-(quinolin-3-yl)-N,N-bis((2-(trimethylsilyl)ethoxy)methyl)-5-vinylpyrazolo[1,5-a]pyrimidin-7-amine (Int-8a)

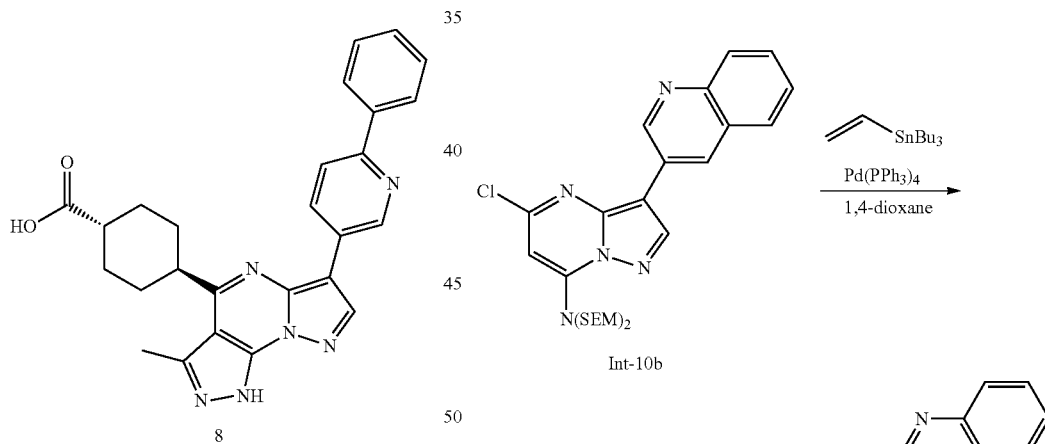

5-Chloro-3-(quinolin-3-yl)-N,N-bis((2-(trimethylsilyl)ethoxy)methyl)pyrazolo[1,5-a]pyrimidin-7-amine (was synthesized as described in Steps A and B of Example 10 below. To Int-10b (0.9 g, 1.64 mmol) in a 20 mL vial was added 1,4-dioxane (10 mL), tributyl(vinyl)tin (0.5 mL, 1.71 mmol)

and Pd(PPh$_3$)$_4$ (0.1 g, 0.08 mmol). The vial was flushed with argon, sealed and heated at 100° C. for 16 hours, at which time LC/MS analysis confirmed full conversion of the starting material to the product. The reaction mixture was filtered through a mixture of silica (8 g) and KF (2 g), and EtOAc was used to wash the filter pad. Concentration of the filtrate gave a brown oil (1.4 g). Further purification via gradient column chromatography on silica eluting with 5% to 40% EtOAc/hexanes gave 3-(quinolin-3-yl)-N,N-bis((2-(trimethylsilyl)ethoxy)methyl)-5-vinylpyrazolo[1,5-a]pyrimidin-7-amine (Int-8a) as a yellow oil (0.7 g, 1.3 mmol, 78%). LCMS: 2.55 mins, m/z=548.2 (MH$^+$).

Step B—Synthesis of 7-(bis((2-(trimethylsilyl)ethoxy)methyl)amino)-3-(quinolin-3-yl)pyrazolo[1,5-a]pyrimidine-5-carbaldehyde (Int-8b)

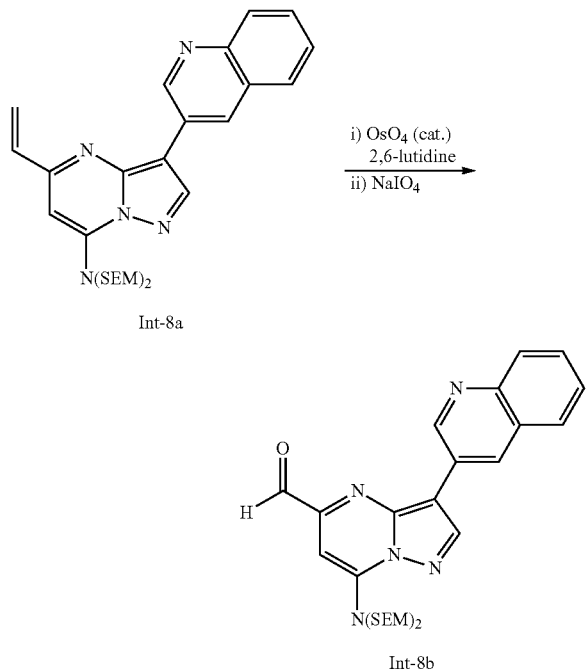

To 3-(quinolin-3-yl)-N,N-bis((2-(trimethylsilyl)ethoxy)methyl)-5-vinylpyrazolo[1,5-a]pyrimidin-7-amine (Int-8a, 0.7 g, 1.3 mmol) in 1,4-dioxane (10 mL) was added 2.5 wt % OsO$_4$ in 1,4-dioxane (1.0 g, 0.02 mmol), 2,6-lutidine (0.6 mL, 5.2 mmol) and H$_2$O (2 mL), and the resulting mixture was stirred at room temperature for 20 minutes. NaIO$_4$ (0.8 g, 3.81 mmol) was then added and the reaction mixture was stirred at room temperature for 16 hours. L C/MS analysis at that time showed the diol intermediate was still present. Therefore, more NaIO$_4$ (0.3 g, 1.3 mmol) was added, and the reaction mixture was stirred for 12 hours for full conversion to the product. Saturated Na$_2$S$_2$O$_3$ solution (10 mL) was added and the mixture was stirred for 10 minutes. The organics were then extracted with CH$_2$Cl$_2$ (4×40 mL), dried (Na$_2$SO$_4$) and concentrated in vacuo to give 7-(bis((2-(trimethylsilyl)ethoxy)methyl)amino)-3-(quinolin-3-yl)pyrazolo[1,5-a]pyrimidine-5-carbaldehyde (Int-8b) as a yellow solid (0.6 g, 1.2 mmol, 92%). LCMS: 2.67 mins, m/z=550.0 (MH$^+$).

Step C—Synthesis of 5-(morpholinomethyl)-3-(quinolin-3-yl)-N,N-bis((2-(trimethylsilyl)-ethoxy)methyl)pyrazolo[1,5-c]pyrimidin-7-amine (Int-8c)

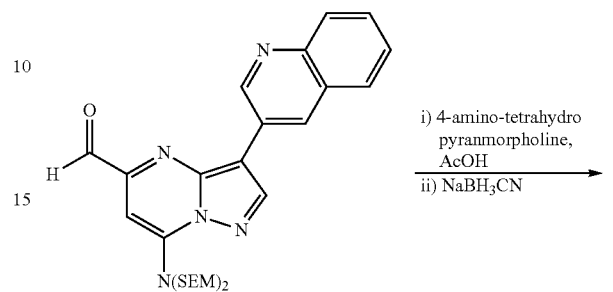

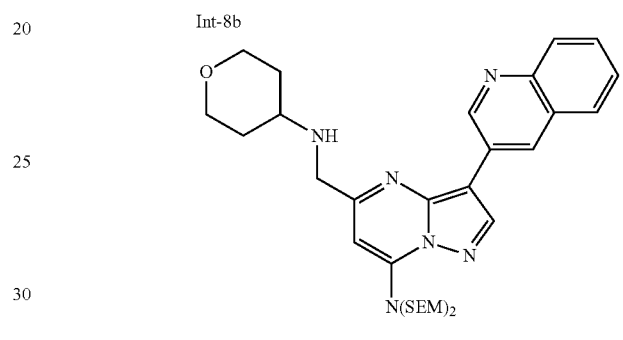

To 7-(bis((2-(trimethylsilyl)ethoxy)methyl)amino)-3-(quinolin-3-yl)pyrazolo[1,5-a]pyrimidine-5-carbaldehyde (Int-8b, 0.15 g, 0.3 mmol) in EtOH (10 mL) was added morpholine (0.12 mL, 1.4 mmol) and AcOH (0.2 mL), and the resulting mixture was stirred at room temperature for 15 minutes. NaBH$_3$CN (0.12 g, 2.0 mmol) in EtOH (1.5 mL total) was then added and the reaction mixture was stirred at room temperature for 16 hours, at which time LC/MS analysis confirmed full consumption of starting material. Saturated NaHCO$_3$ solution (~20 mL) was added and the mixture was stirred for 30 minutes. The mixture was transferred to a separatory funnel with CH$_2$Cl$_2$ (30 mL). H$_2$O (10 mL) and brine (20 mL) were then added. Organics were extracted with CH$_2$Cl$_2$ (4×30 mL), dried (Na$_2$SO$_4$) and concentrated in vacuo to give crude product (0.2 g). LCMS: 2.01 mins, m/z=635.3 (MH$^+$).

Step D—Synthesis of tert-butyl (7-(bis((2-(trimethylsilyl)ethoxy)methyl)amino)-3-(quinolin-3-yl)pyrazolo[1,5-a]pyrimidin-5-yl)methyl(tetrahydro-2H-pyran-4-yl)carbamate (Int-8d)

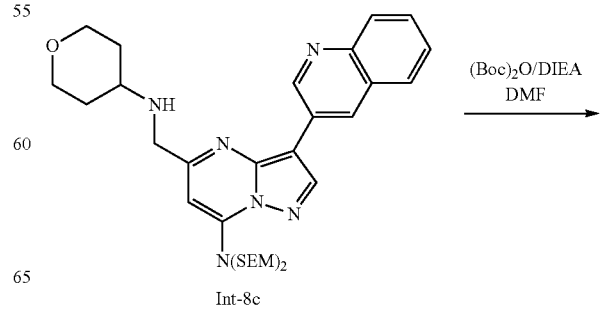

-continued

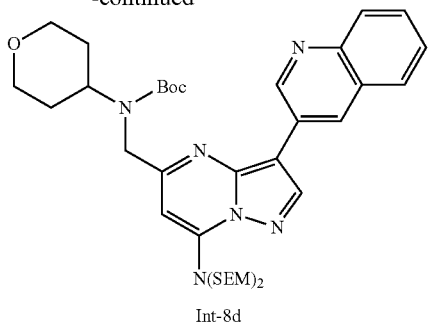

Int-8d

Tert-butyl (7-(bis((2-(trimethylsilyl)ethoxy)methyl)amino)-3-(quinolin-3-yl)pyrazolo[1,5-a]pyrimidin-5-yl)methyl(tetrahydro-2H-pyran-4-yl)carbamate (Int-8c, 100 mg) dissolved in dimethyl formamide (2 mL) and diethyl isopropyl amine (3 equivalents) was added to it, followed by Boc-anhydride (1.1 equivalent) while stirring. The solution was stirred at room temperature for 14 hours at room temperature. The crude product on LCMS analysis showed the completion of reaction. The reaction mixture was diluted with ethyl acetate (50 mL) and extracted with water, washed with brine and dried over anhydrous sodium sulfate. Solid was filtered off, and the ethyl acetate on concentration gave the product, which was purified by column chromatography using hexane-ethyl acetate (3:1) as eluant to give the pure title product. LCMS: 3.01 mins, m/z=735.20 (MH+).

Step E—Synthesis of tert-butyl (7-(bis((2-(trimethylsilyl)ethoxy)methyl)amino)-6-bromo-3-(quinolin-3-yl)pyrazolo[1,5-a]pyrimidin-5-yl)methyl(tetrahydro-2H-pyran-4-yl)carbamate (Int-8e)

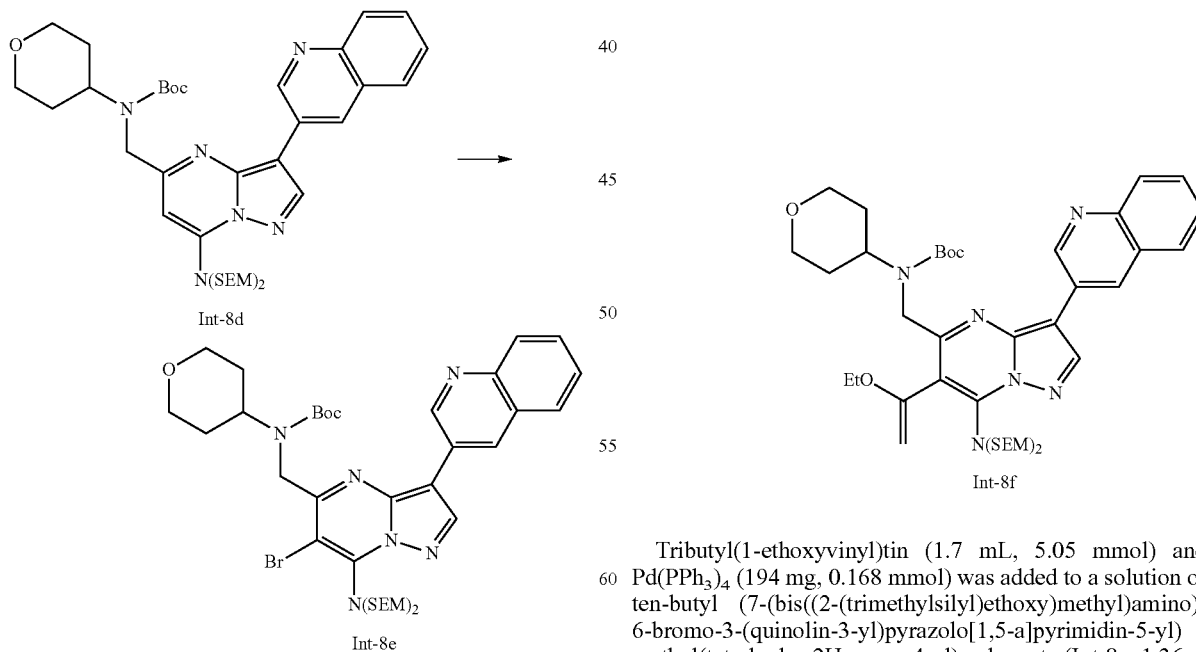

To crude tert-butyl (7-(bis((2-(trimethylsilyl)ethoxy)methyl)amino)-3-(quinolin-3-yl)pyrazolo[1,5-a]pyrimidin-5-yl)methyl(tetrahydro-2H-pyran-4-yl)carbamate (Int-8d, 44 mg) in CH$_3$CN (8 mL) was added N-bromosuccinimide (22 mg, 0.12 mmol), followed by additional CH$_3$CN (4 mL). The reaction was then stirred at room temperature for 30 minutes, at which time LC/MS analysis confirmed full conversion of the starting material to the product. The reaction mixture was concentrated in vacuo and purified by preparative HPLC to give Int-8e as a yellow solid (8.7 mg, 0.02 mmol, 7% over three steps). LCMS: 0.82 mins, m/z=812.10 and 813.20 (MH+).

Step F—Synthesis of tert-butyl (7-(bis((2-(trimethylsilyl)ethoxy)methyl)amino)-6-(1-ethoxyvinyl)-3-(quinolin-3-yl)pyrazolo[1,5-a]pyrimidin-5-yl)methyl(tetrahydro-2H-pyran-4-yl)carbamate (Int-8f)

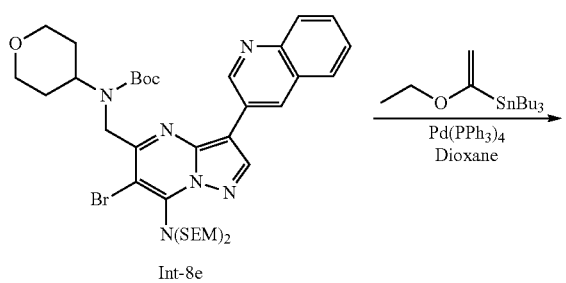

Int-8f

Tributyl(1-ethoxyvinyl)tin (1.7 mL, 5.05 mmol) and Pd(PPh$_3$)$_4$ (194 mg, 0.168 mmol) was added to a solution of ten-butyl (7-(bis((2-(trimethylsilyl)ethoxy)methyl)amino)-6-bromo-3-(quinolin-3-yl)pyrazolo[1,5-a]pyrimidin-5-yl) methyl(tetrahydro-2H-pyran-4-yl)carbamate (Int-8e, 1.36 g, 1.68 mmol) in 1,4-dioxane (10 mL). The reaction was heated to 100° C. under argon for 18 hours. After 18 hours, the solvent was removed in vacuo and the residue was purified via silica gel chromatography (0% to 30% ethyl acetate in hexanes gradient) to yield the title compound (1.3 g, 96% yield) as yellow oil. LC-MS: 805 [M+H].

Step G—Synthesis of N-((3-methyl-6-(quinolin-3-yl)-1H-dipyrazolo[1,5-a:4',3'-e]pyrimidin-4-yl)methyl)tetrahydro-2H-pyran-4-amine (Compound 26)

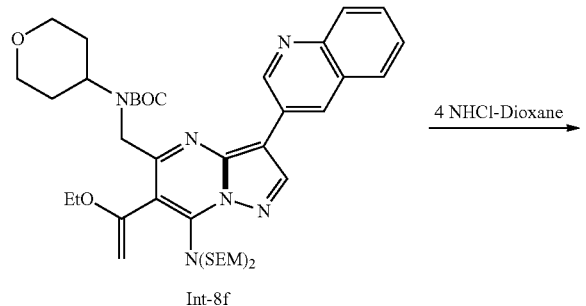

Int-8f

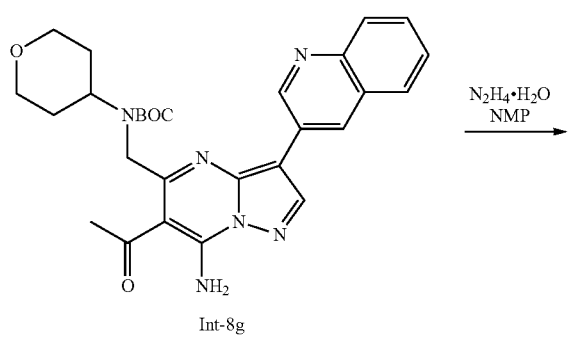

Int-8g

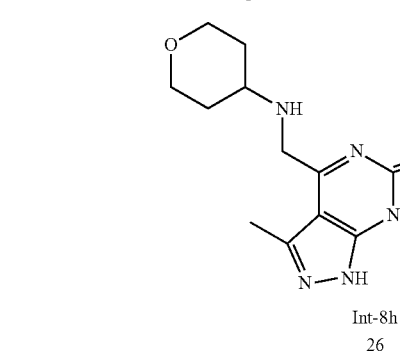

Int-8h
26

A mixture of tert-butyl (7-(bis((2-(trimethylsilyl)ethoxy)methyl)amino)-6-(1-ethoxyvinyl)-3-(quinolin-3-yl)pyrazolo[1,5-a]pyrimidin-5-yl)methyl(tetrahydro-2H-pyran-4-yl)carbamate (Int-8f, 35 mg), 4N HCl in dioxane (0.3 mL) and dioxane (2 mL) was heated at 60° C. for 10 min. Concentration afforded crude tert-butyl (6-acetyl-7-amino-3-(quinolin-3-yl)pyrazolo[1,5-a]pyrimidin-5-yl)methyl(tetrahydro-2H-pyran-4-yl)carbamate (Int-8g), which was then heated under microwave conditions with N₂H₄.H₂O (200 uL) and NMP (1.5 mL) first at 100° C. for 30 min and then at 200° C. for 1h. Purification with prep-LC provided N-((3-methyl-6-(quinolin-3-yl)-1H-dipyrazolo[1,5-a:4',3'-e]pyrimidin-4-yl)methyl)tetrahydro-2H-pyran-4-amine (26), LCMS $t_R$=1.48 mM (10 min run, $UV_{254nm}$). Mass calculated for, M+413.0, observed Example 9

Preparation of Compound 30

Step A—Synthesis of pyrazolo[1,5-a]pyrimidine-5,7-diol (Int-9a)

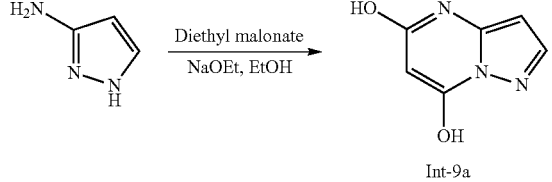 [SMILES: Nc1cc[nH]n1 ; Oc1cc(O)n2nccc2n1]

Int-9a

To 1H-pyrazol-3-amine (12.3 g, 148.0 mmol) in EtOH (50 mL) was added diethyl malonate (25.0 mL, 164.7 mmol), 21 wt % NaOEt in EtOH (110 mL, 294.6 mmol) and additional EtOH (50 mL). The resulting reaction mixture was then heated at 80° C. under an atmosphere of argon for 16 hours, at which time the reaction was allowed to cool to room temperature. The reaction mixture was then concentrated in vacuo until almost dry, before H₂O (500 mL) was added. Vigorous stirring aided the dissolution of solids, at which time conc. HCl was added until pH~2 was attained (precipitate formed). The precipitate was collected and dried by vacuum filtration giving pyrazolo[1,5-a]pyrimidine-5,7-diol (Int-9a) as a tan solid (17.13 g, 113.4 mmol, 77%).

Step B—Synthesis of 5,7-dichloropyrazolo[1,5-a]pyrimidine (Int-9b)

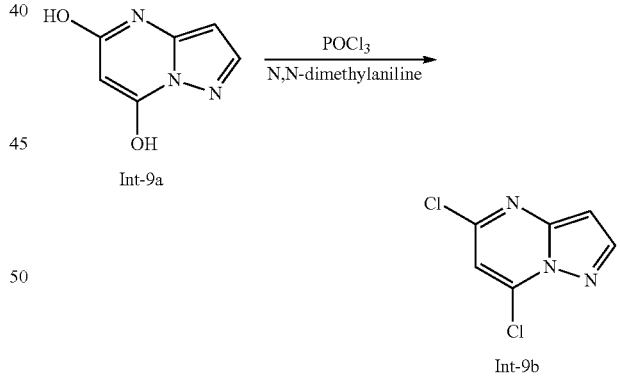

To pyrazolo[1,5-a]pyrimidine-5,7-diol (Int-9a, 9.6 g, 63.5 mmol) in a 500 mL flask was added POCl₃ (125 mL, 1341.1 mmol). The flask was then cooled to 0° C. and N,N-dimethylaniline (22 mL, 173.6 mmol) was carefully added. On warming to room temperature, the reaction mixture was then heated at 60° C. under an atmosphere of argon for 16 hours. On cooling, the reaction mixture was concentrated in vacuo to give a brown viscous liquid. This brown viscous liquid was carefully poured onto ice and allowed to warm to room temperature overnight. To the brown solution was carefully added saturated NaHCO₃ solution until no further effervescence was observed and pH ~8 was attained. Organics were then extracted with CH₂Cl₂ (4×50 mL), dried (Na₂SO₄) and concentrated in vacuo to give a brown liquid (29.8 g). Gradient column chromatography on silica eluting with 50% CH₂Cl₂/hexanes (to elute aniline) followed by 75% CH₂Cl₂/hexanes (to elute product) gave 5,7-dichloropyrazolo[1,5-a]pyrimidine (Int-9b) as a white solid (7.7 g, 40.8 mmol, 64%).

Step C—Synthesis of 5-chloropyrazolo[1,5-a]pyrimidin-7-amine (Int-9c)

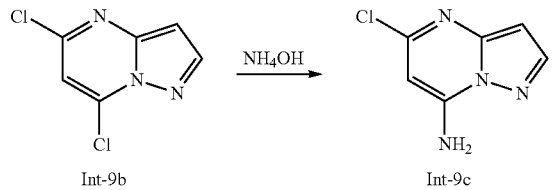

To 5,7-dichloropyrazolo[1,5-a]pyrimidine (Int-9b, 7.6 g, 40.4 mmol) in a sealed vessel was added NH₄OH (100 mL). The vessel was then sealed and heated at 85° C. for 2.5 hours, at which time the consistency of the white solid had changed (from foamy white solid to free-flowing white solid). The vessel was removed from the heat source and allowed to cool to room temperature overnight. On cooling, the contents of the vessel were collected and dried by vacuum filtration giving 5-chloropyrazolo[1,5-a]pyrimidin-7-amine (Int-9c) as a yellow-tinged white solid (6.8 g, 40.3 mmol, 100%).

Step D—Synthesis of 5-chloro-N,N-bis((2-(trimethylsilyl)ethoxy)methyl)pyrazolo[1,5-a]pyrimidin-7-amine (Int-9d)

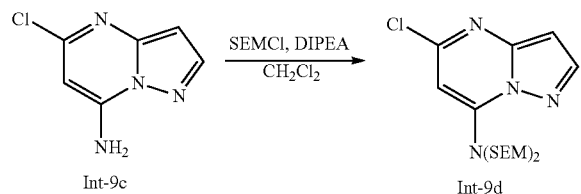

To 5-chloropyrazolo[1,5-a]pyrimidin-7-amine (Int-9c, 6.7 g, 39.7 mmol) in CH₂Cl₂ (30 mL) was added N,N-diisopropylethylamine (48.0 mL, 275.6 mmol) followed by 2-(trimethylsilyl)ethoxymethyl chloride (25.0 mL, 141.7 mmol). The reaction mixture was heated at 45° C. for 3 hours before being allowed to cool to room temperature. The reaction mixture was then poured into a separatory funnel containing ~100 mL saturated NaHCO₃ solution and CH₂Cl₂ (50 mL). Organics were then extracted with CH₂Cl₂ (4×50 mL), dried (Na₂SO₄) and concentrated in vacuo to give a thick orange liquid (33.8 g). Gradient column chromatography on silica eluting with 5% to 15% EtOAc/hexanes gave crude 5-chloro-N,N-bis((2-(trimethylsilyl)ethoxy)methyl)pyrazolo[1,5-a]pyrimidin-7-amine (Int-9d) as a colorless liquid (18.7 g).

Step E—Synthesis of tert-butyl 4-(7-(bis((2-(trimethylsilyl)ethoxy)methyl)amino)pyrazolo[1,5-a]pyrimidin-5-yl)-5,6-dihydropyridine-1(2H)-carboxylate (Int-9e)

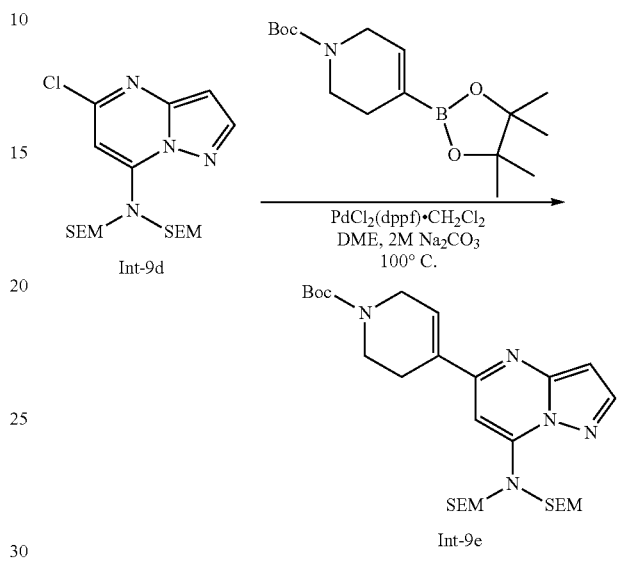

To a pressure tube was charged 5-chloro-N,N-bis((2-(trimethylsilyl)ethoxy)methyl)pyrazolo[1,5-a]pyrimidin-7-amine (Int-9d, 5.36 g, 12.5 mmol), tert-butyl 4-(4,4,5,5-tetramethyl-1,3,2-dioxaborolan-2-yl)-5,6-dihydropyridine-1 (2H)-carboxylate (4.26 g, 13.8 mmol), [1,1'-bis(diphenylphosphino)ferrocene]dichloropalladium(II) complex with dichloromethane (1:1) (510 mg, 0.62 mmol), 2M Na₂CO₃ (30 ml) and DME (60 ml). The tube was degassed with Ar briefly, capped and heated at 100° C. with stirring overnight. After cooling, the reaction mixture was diluted with EtOAc and water, the organic layer was isolated, washed with brine and dried (MgSO₄). After the solvent was removed under reduced pressure, the residue was purified on silica. Elution with EtOAc in hexanes (0-25%) gave tert-butyl 4-(7-(bis((2-(trimethylsilyl)ethoxy)methyl)amino)pyrazolo[1,5-a]pyrimidin-5-yl)-5,6-dihydropyridine-1(2H)-carboxylate (Int-9e) (5.76 g, 80%).

LC/MS: m/z=576.2 (M+H⁺).

Step F—Synthesis of tert-butyl 4-(7-(bis((2-(trimethylsilyl)ethoxy)methyl)amino)pyrazolo[1,5-a]pyrimidin-5-yl)piperidine-1-carboxylate (Int-9f)

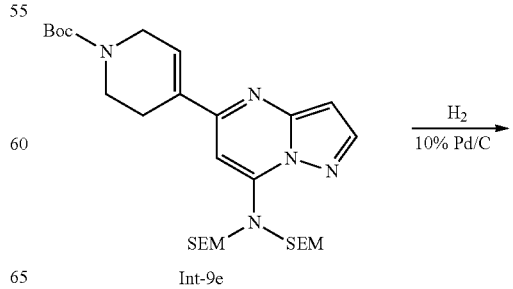

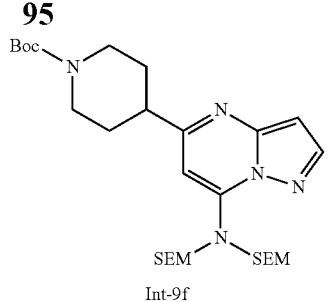

Int-9f

A mixture of tert-butyl 4-(7-(bis((2-(trimethylsilyl)ethoxy)methyl)amino)pyrazolo[1,5-a]pyrimidin-5-yl)-5,6-dihydropyridine-1(2H)-carboxylate (Int-9e, 5.05 g) and 10% Pd/C (300 mg) in EtOAc was stirred at 45° C. under hydrogen (balloon pressure) for three hours. After filtration and concentration, tert-butyl 4-(7-(bis((2-(trimethylsilyl)ethoxy)methyl)amino)pyrazolo[1,5-a]pyrimidin-5-yl)piperidine-1-carboxylate (Int-9f) (5.1 g) was obtained as an oil. LC/MS: m/z=578.3 (M+H$^+$).

Step G—Synthesis of tert-butyl 4-(7-(bis((2-(trimethylsilyl)ethoxy)methyl)amino)-3-iodopyrazolo[1,5-a]pyrimidin-5-yl)piperidine-1-carboxylate (Int-9g)

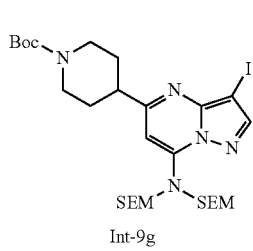

Int-9f

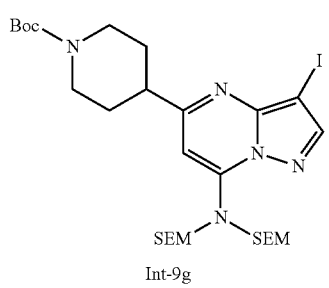

Int-9g

To tert-butyl 4-(7-(bis((2-(trimethylsilyl)ethoxy)methyl)amino)pyrazolo[1,5-a]pyrimidin-5-yl)piperidine-1-carboxylate (Int-9f, 18.8 g, 32.5 mmol) in CH$_3$CN (130 mL) and dichloromethane (130 mL) was added N-iodosuccinimide (8 g, 35.8 mmol) portionwise and the resulting mixture was stirred at room temperature for 1.5 h, at which time LC/MS confirmed full conversion of starting material to product. Solvent was removed in vacuo and the residue was purified by column chromatography on silica gel. Elution with EtOAc/Hexanes (0-50%) gave the desired product, tert-butyl 4-(7-(bis((2-(trimethylsilyl)ethoxy)methyl)amino)-3-iodopyrazolo[1,5-a]pyrimidin-5-yl)piperidine-1-carboxylate (Int-9g) (21.7 g, 95%). LC/MS: m/z=704.2 (M+H$^+$).

Step H—Preparation of tert-butyl 4-(7-(bis((2-(trimethylsilyl)ethoxy)methyl)amino)-3-(6-phenylpyridin-3-yl)pyrazolo[1,5-a]pyrimidin-5-yl)piperidine-1-carboxylate (Int-9h)

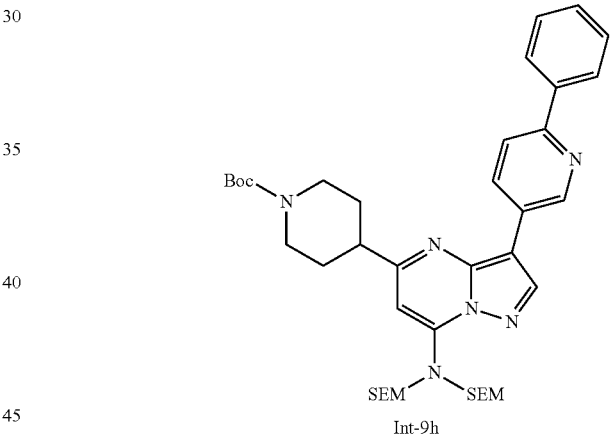

Int-9h

To a pressure tube were charged tert-butyl 4-(7-(bis((2-(trimethylsilyl)ethoxy)methyl)amino)-3-iodopyrazolo[1,5-a]pyrimidin-5-yl)piperidine-1-carboxylate (Int-9g, 1.7 g, 2.4 mmol), 2-phenyl-5-(4,4,5,5-tetramethyl-1,3,2-dioxaborolan-2-yl)pyridine (800 mg, 2.8 mmol), [1,1'-bis(diphenylphosphino)-ferrocene]dichloropalladium(II) complex with dichloromethane (1:1) (100 mg, 0.12 mmol), K$_2$CO$_3$ (666 mg, 4.8 mmol), DME (10 mL) and water (5 mL). The tube was degassed with Ar briefly, capped and heated at 100° C. with stirring overnight. After cooling, the reaction mixture was diluted with EtOAc and water, the organic layer was isolated, washed with brine and dried (MgSO$_4$). After the solvent was removed under reduced pressure, the residue was purified on silica. Elution with EtOAc in hexanes (0-50%) gave tert-butyl 4-(7-(bis((2-(trimethylsilyl)ethoxy)methyl)

amino)-3-(6-phenyl pyridin-3-yl)pyrazolo[1,5-a]pyrimidin-5-yl)piperidine-1-carboxylate (Int-9h) (1 g, 57%). LC/MS: m/z=731 (M+H⁺).

Step I—Preparation of tert-butyl 4-(7-(bis((2-(trimethylsilyl)ethoxy)methyl)amino)-6-bromo-3-(6-phenylpyridin-3-yl)pyrazolo[1,5-a]pyrimidin-5-yl)piperidine-1-carboxylate (Int-9i)

and the residue was purified on silica. Elution with EtOAc in hexanes (0-50%) gave the title compound (3 g, 83%). LC/MS: m/z=809 (M+H⁺).

Step J—Synthesis of 3-methyl-6-(6-phenylpyridin-3-yl)-4-(piperidin-4-yl)-1H-dipyrazolo[1,5-a:4',3'-e]pyrimidine (Int-9l)

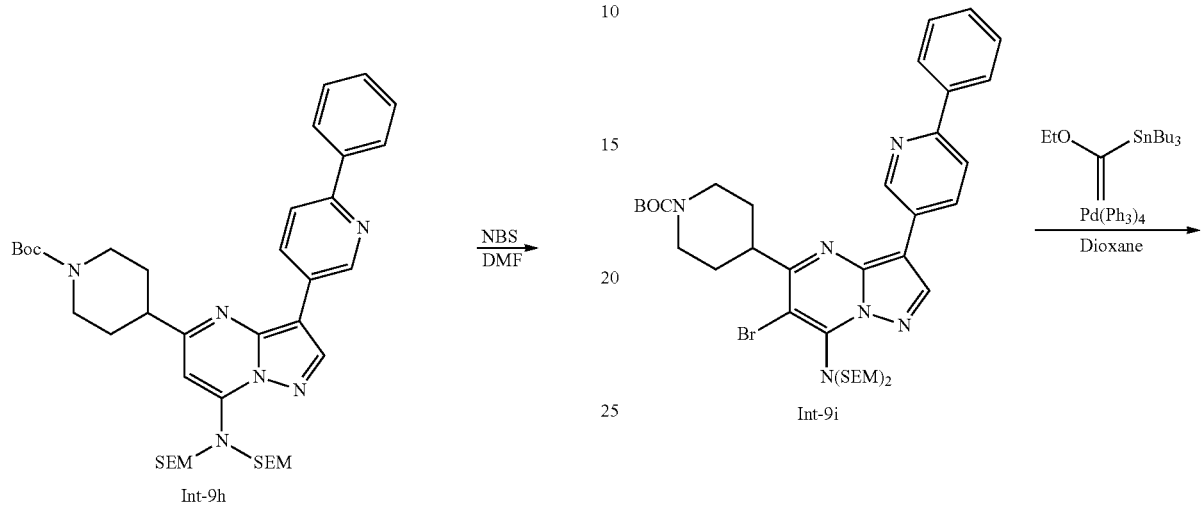

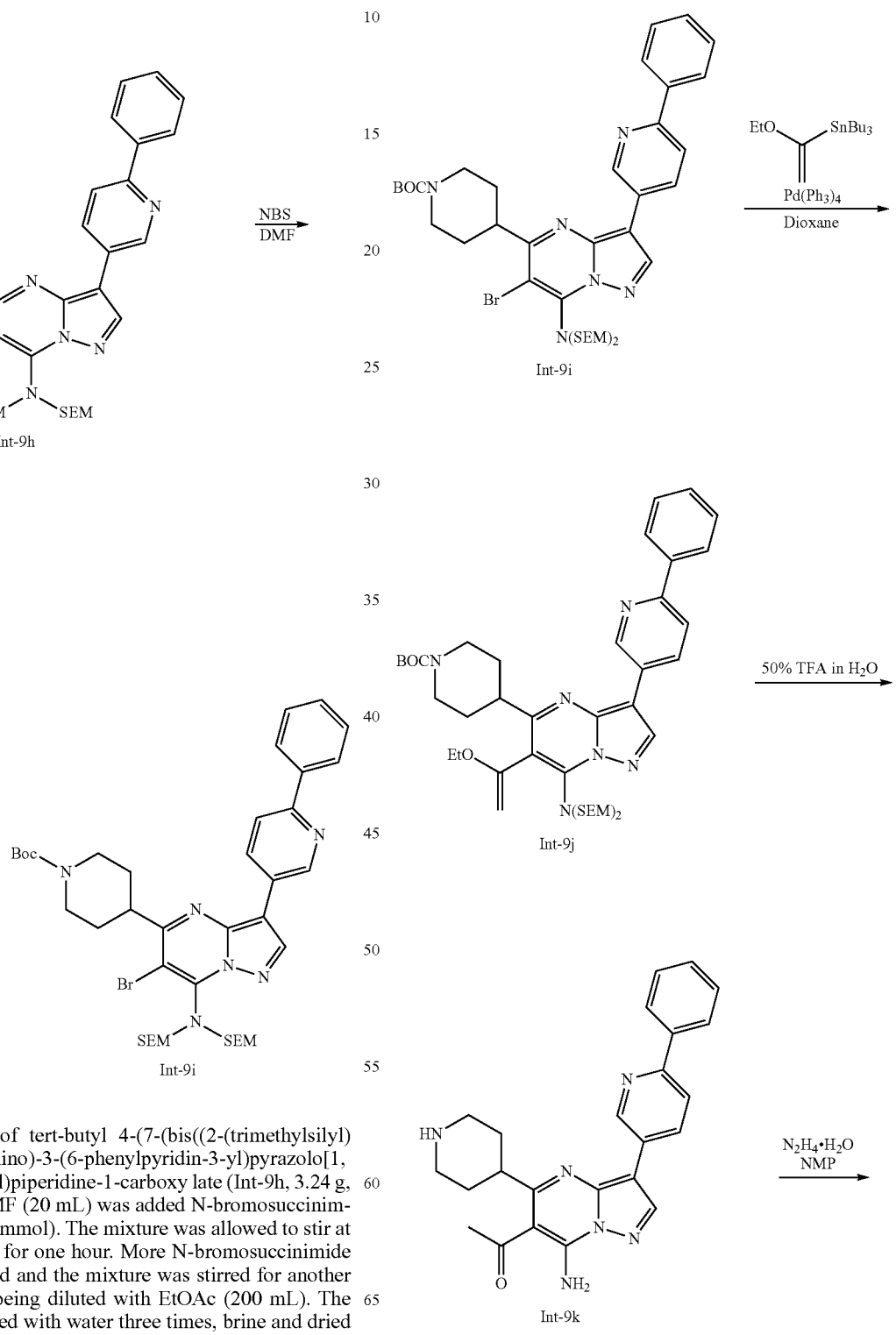

To a solution of tert-butyl 4-(7-(bis((2-(trimethylsilyl)ethoxy)methyl)amino)-3-(6-phenylpyridin-3-yl)pyrazolo[1,5-a]pyrimidin-5-yl)piperidine-1-carboxylate (Int-9h, 3.24 g, 4.44 mmol) in DMF (20 mL) was added N-bromosuccinimide (750 mg, 4.21 mmol). The mixture was allowed to stir at room temperature for one hour. More N-bromosuccinimide (75 mg) was added and the mixture was stirred for another half hour before being diluted with EtOAc (200 mL). The mixture was washed with water three times, brine and dried (MgSO₄). After solvent was removed under reduced pressure,

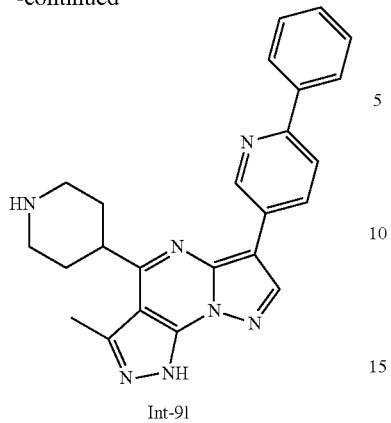

Int-91

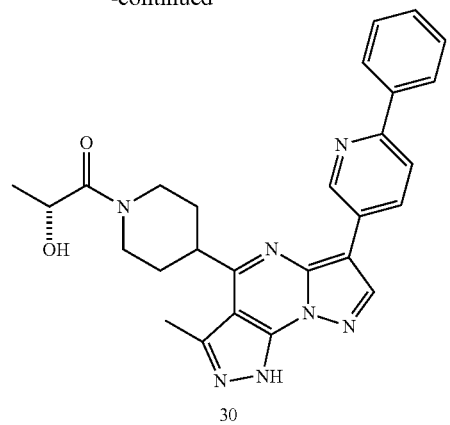

30

A degassed mixture of tert-butyl 4-(7-(bis((2-(trimethylsilyl)ethoxy)methyl)amino)-6-bromo-3-(6-phenylpyridin-3-yl)pyrazolo[1,5-a]pyrimidin-5-yl)piperidine-1-carboxylate (Int-91, 154 mg, 0.19 mmoL), Pd(PPh$_3$)$_4$ (22 mg, 0.019 mmoL), tributyl(1-ethoxyvinyl)stannane (103 mg, 0.28 mmoL) in dioxane (3 mL) was heated at 100° C. overnight. The reaction mixture was cooled to room temperature, filtered through 9:1 SiO$_2$:KF plug and concentrated in vacuo. The crude tert-butyl 4-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)piperidine-1-carboxylate (Int-9j) was treated with 50% TFA in H$_2$O (4 mL) until the disappearance of starting material in LCMS. Concentration afforded crude 1-(7-amino-3-(6-phenylpyridin-3-yl)-5-(piperidin-4-yl)pyrazolo[1,5-a]pyrimidin-6-yl)ethanone (Int-9k), which was then heated under microwave conditions with N$_2$H$_4$.H$_2$O (800 uL) and NMP (6 mL) first at 100° C. for 30 min and then at 200° C. for 1 h. Purification with prep-LC provided 3-methyl-6-(6-phenylpyridin-3-yl)-4-(piperidin-4-yl)-1H-dipyrazolo[1,5-a:4',3'-e]pyrimidine (Int-91): LCMS t$_R$=2.49 Min (10 min run, UV$_{254m}$). Mass calculated for, M+409.2, observed LC/MS m/z 410.6 (M+H).

Step K—Synthesis of (R)-2-hydroxy-1-(4-(3-methyl-6-(6-phenylpyridin-3-yl)-1H-dipyrazolo[1,5-a:4',3'-e]pyrimidin-4-ylpiperidin-1-yl)propan-1-one (Compound 30)

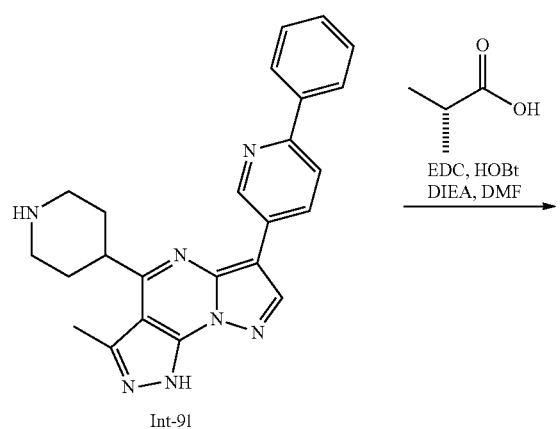

Int-91

A mixture of 3-methyl-6-(6-phenylpyridin-3-yl)-4-(piperidin-4-yl)-1H-dipyrazolo[1,5-a:4',3'-e]pyrimidine (Int-9l, 42 mg, (\10 mmoL), D-(−)-lactic acid (9.3 mg, 0.10 mmoL), EDC (39.4 mg, 0.20 mmoL), HOBt (13.9 mg, 0.10 mmoL) and DIEA (89 μL, 0.51 mmoL) in DMF (4 mL) was stirred at room temperature for 2 hr. Purification with prep-LC provided (R)-2-hydroxy-1-(4-(3-methyl-6-(6-phenylpyridin-3-yl)-1H-dipyrazolo[1,5-a:4',3'-e]pyrimidin-4-yl)piperidin-1-yl)propan-1-one (30): LCMS t$_R$=3.07 min (10 min run, UV$_{254nm}$) Mass calculated for, M+481.2, observed LC/MS m/z 482.6 (M+H).

Example 10

Preparation of Compound 17

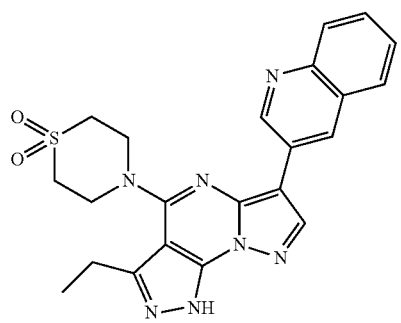

17

Step A—Synthesis of 5-chloro-3-iodo-N,N-bis((2-(trimethylsilyl)ethoxy)methyl)pyrazolo[1,5-a]pyrimidin-7-amine (Int-10a)

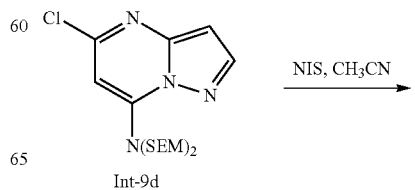

Int-9d

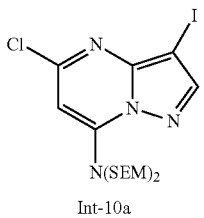

Int-10a

To crude 5-chloro-N,N-bis((2-(trimethylsilyl)ethoxy)methyl)pyrazolo[1,5-a]pyrimidin-7-amine (Int-9d, 7.9 g) (prepared as described in Steps A-D of Example 9) in CH₃CN (100 mL) was added N-iodosuccinimide (4.3 g, 19.2 mmol) and the resulting mixture was stirred at room temperature for 30 mins, at which time LC/MS confirmed full conversion of starting material to product. Saturated sodium thiosulfate solution (~20 mL) was added and stirring continued for 5 minutes before the mixture was transferred to a separatory funnel using CH₂Cl₂ (30 mL) and H₂O (30 mL). Brine (50 mL) was added and organics were extracted with CH₂Cl₂ (4×40 mL), dried (Na₂SO₄) and concentrated in vacuo to give crude 5-chloro-3-iodo-N,N-bis((2-(trimethylsilyl)ethoxy)methyl)pyrazolo[1,5-a]pyrimidin-7-amine (Int-10a) as a light brown liquid (10.4 g). LCMS: 2.95 mins, m/z=555.1 (MH⁺).

Step B—Synthesis of 5-chloro-3-(quinolin-3-yl)-N,N-bis((2-(trimethylsilyl)ethoxy)methyl)pyrazolo[1,5-a]pyrimidin-7-amine (Int-10b)

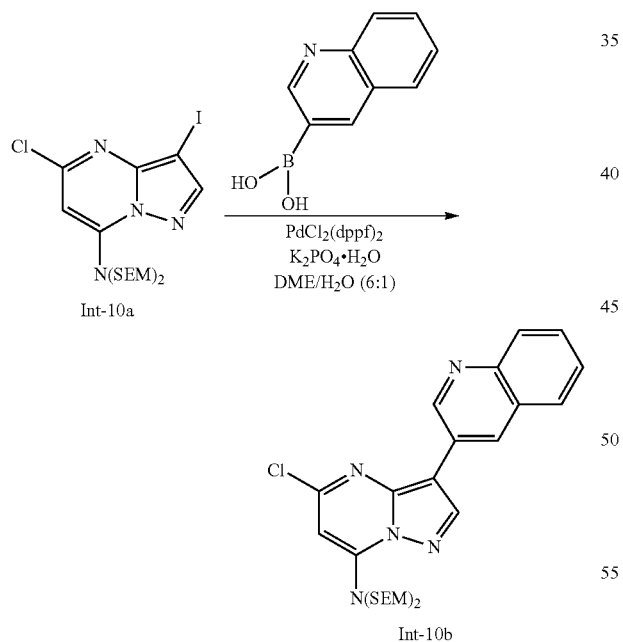

To crude 5-chloro-3-iodo-N,N-bis((2-(trimethylsilyl)ethoxy)methyl)pyrazolo[1,5-a]pyrimidin-7-amine (Int-10b, 7.1 g) in DME (120 mL) and H₂O (15 mL) were added the quinoline boronic acid (2.4 g, 14.1 mmol), PdCl₂(dppf)₂ (1.0 g, 1.2 mmol) and K₃PO₄·H₂O (5.4 g, 25.6 mmol). The reaction mixture was heated at 60° C. for 2 hours, at which time LC/MS analysis confirmed full consumption of starting material. On cooling, H₂O (40 mL) and EtOAc (100 mL) were added and organics were extracted with EtOAc (4×50 mL), dried (Na₂SO₄), and concentrated in vacuo to give a brown oil. Gradient column chromatography on silica eluting with 10% to 60% EtOAc/hexanes gave 5-chloro-3-(quinolin-3-yl)-N,N-bis((2-(trimethylsilyl)ethoxy)methyl)pyrazolo[1,5-a]pyrimidin-7-amine (Int-10b) as a light yellow solid (4.1 g, 7.4 mmol, 65% over three steps).

LCMS: 2.62 mins, m/z=556.2 (MH⁺).

Step C—Preparation of Int-10c

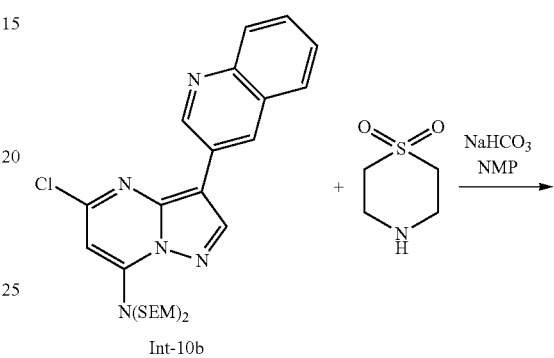

Int-10b

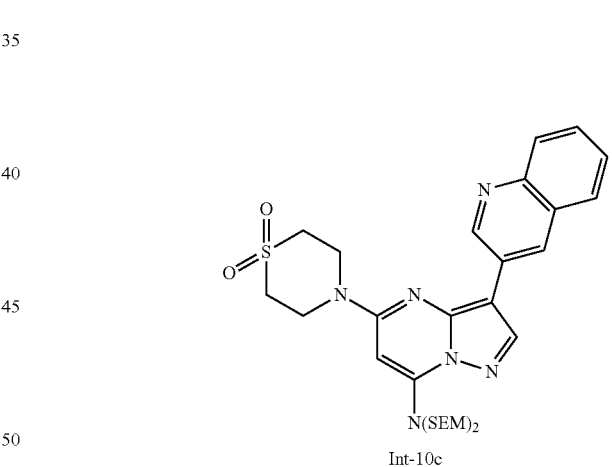

Int-10c

A mixture of 5-chloro-3-(quinolin-3-yl)-N,N-bis((2-(trimethylsilyl)ethoxy)methyl)pyrazolo[1,5-a]pyrimidin-7-amine (Int-10b, 503.0 mg, 0.91 mmoL), thiomorpholine dioxide (367.1 mg, 2.72 mmoL), NaHCO₃ (533.0 mg, 6.34 mmoL) in NMP (8 mL) was heated at 130° C. overnight. The mixture was cooled to room temperature and diluted with H₂O and then extracted with ethyl acetate (x2). The combined organic layers were washed with brine and dried with Na₂SO₄. Evaporation of solvent afforded the crude displacement compound. Purification by column chromatography afforded Int- 10c: LCMS $t_R$=2.52 min (5 min run, $UV_{254nm}$). Mass calculated for, M+654.2, observed m/z 655.2 (M+H).

Step D—Preparation of Int-10d

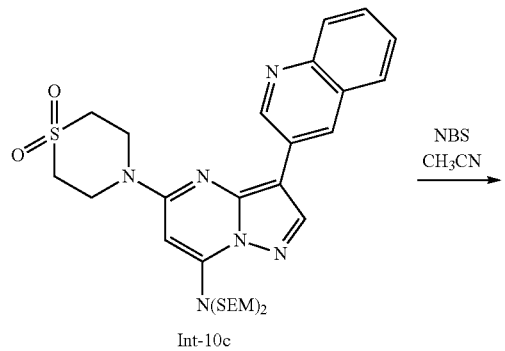

Int-10c

By essentially the same procedure given in Step B of Example 3, Int-10d was prepared from Int-10c.

Step E—Preparation of Int-10f

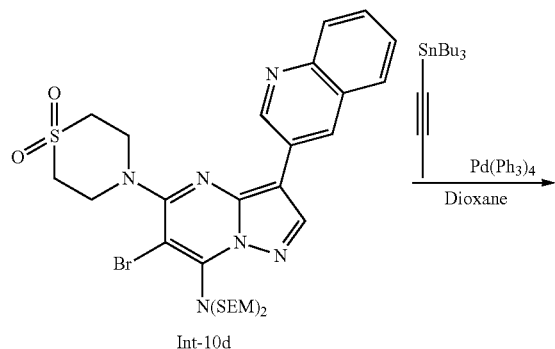

Int-10d

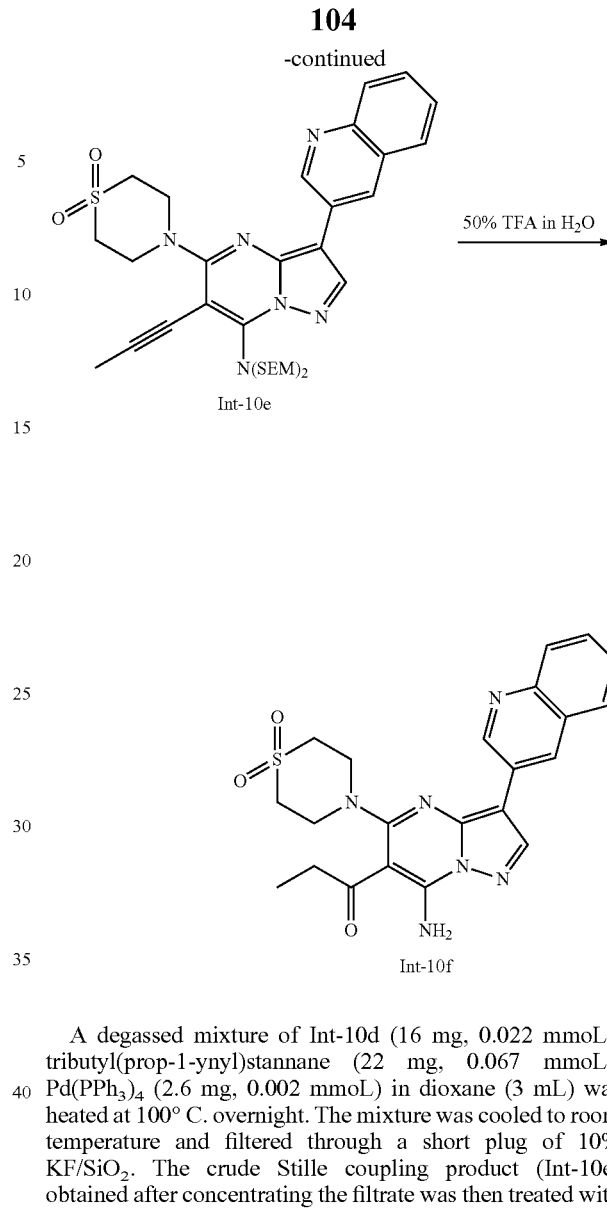

Int-10e

Int-10f

A degassed mixture of Int-10d (16 mg, 0.022 mmoL), tributyl(prop-1-ynyl)stannane (22 mg, 0.067 mmoL), Pd(PPh$_3$)$_4$ (2.6 mg, 0.002 mmoL) in dioxane (3 mL) was heated at 100° C. overnight. The mixture was cooled to room temperature and filtered through a short plug of 10% KF/SiO$_2$. The crude Stille coupling product (Int-10e) obtained after concentrating the filtrate was then treated with 1:1 mixture of TFA and H$_2$O at room temperature for 30 min. Concentration and purification by prep-LC afforded Int-10f. LCMS $t_R$=3.20 min (10 min run, $UV_{254nm}$). Mass calculated for, M+450.1, observed m/z 451.1 (M+H).

Step F—Preparation of Compound 17

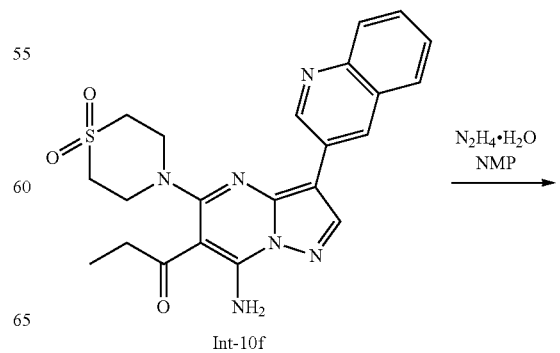

Int-10f

-continued

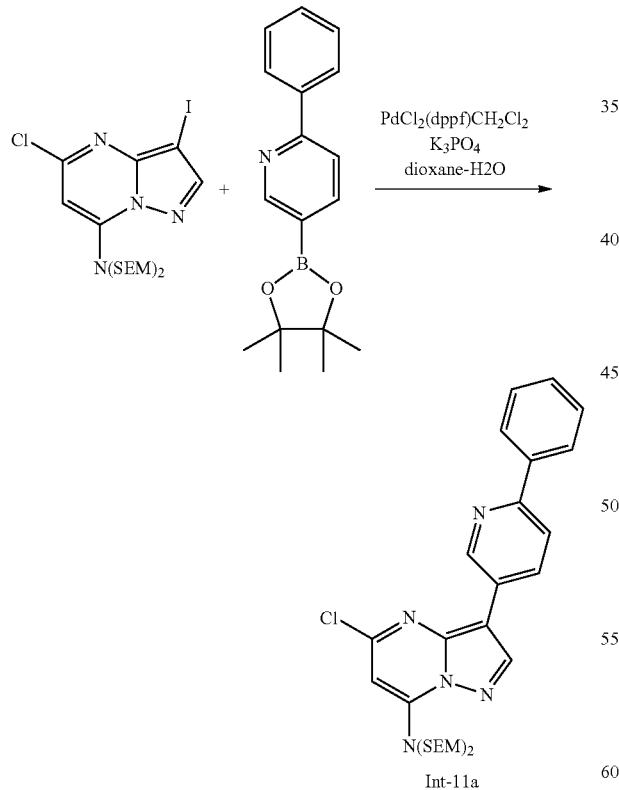

17

By essentially the same procedure given in Step D of Example 3, compound 17 was prepared from Int-10f. LCMS $t_R$=2.45 Min (10 min run, $UV_{254nm}$). Mass calculated for, M+447.1, observed m/z 448.1 (M+H).

Example 11

Preparation of Compound 35

Step A—Synthesis of 5-chloro-3-(6-phenylpyridin-3-yl)-N,N-bis((2-(trimethylsilyl)ethoxy)methyl)pyrazolo[1,5-a]pyrimidin-7-amine (Int-11a)

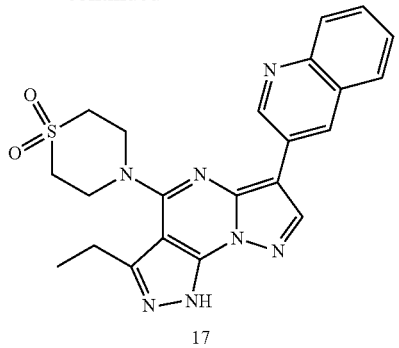

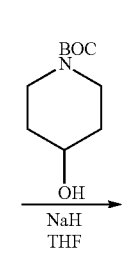

Int-11a 2-phenyl-5-(4,4,5,5-tetramethyl-1,3,2-dioxaborolan-2-yl)pyridine (2.38 mmol, 675 mg), $K_3PO_4$ (5.96 mmol, 1264 mg), and $PdCl_2$(dppf).$CH_2Cl_2$ (0.20 mmol, 162 mg) was added to a solution of 5-chloro-3-iodo-N,N-bis((2-(trimethylsilyl)ethoxy)methyl)pyrazolo[1,5-a]pyrimidin-7-amine (Int-10a, 1.98 mmol, 1101 mg) (prepared as described in Step a of Example 10) in dioxane (18 mL) and $H_2O$ (3 mL). The resulting solution was stirred at 70° C. under argon overnight. The mixture was diluted with $H_2O$ and then extracted with ethyl acetate (x2). The combined organic layers were washed with brine and dried with $Na_2SO_4$. Evaporation and purification by column chromatography afforded 5-chloro-3-(6-phenylpyridin-3-yl)-N,N-bis((2-(trimethylsilyl)ethoxy)methyl)pyrazolo[1,5-a]pyrimidin-7-amine (Int-11a): LCMS $t_R$=3.36 Min (5 min run, UV) Mass calculated for, M+581.2, observed LC/MS m/z 582.2 (M+H).

Step B—Synthesis of Int-11b

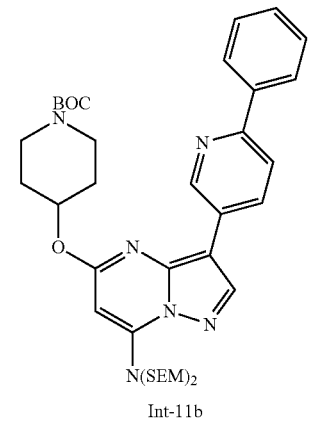

Int-11b

NaH (120 mg, 3 mmoL) was added to a solution of tert-butyl 4-hydroxypiperidine-1-carboxylate (522 mg, 2.60 mmoL) in THF (8 mL). After stirring at room temperature for 5 min, (Int-11a, 755 mg, 1.30 mmoL) in THF (4 mL) was added dropwise. The mixture was heated under microwave conditions at 100° C. for 30 min, diluted with HA) and then extracted with ethyl acetate (x2). The combined organic layers were washed with brine and dried with $Na_2SO_4$. Evaporation and purification by column chromatography afforded tert-butyl 4-(7-(bis((2-(trimethylsilyl)ethoxy)methyl)amino)-3-(6-phenylpyridin-3-yl)pyrazolo[1,5-a]pyrimidin-5-yloxy)piperidine-1-carboxylate (Int-11b): LCMS $t_R$=3.53

Min (5 min run, UV$_{254nm}$). Mass calculated for, M+746.4, observed LC/MS m/z 747.2 (M+H).

Step C—Synthesis of tert-butyl 4-(7-(bis((2-(trimethylsilyl)ethoxy)methyl)amino)-6-bromo-3-(6-phenylpyridin-3-yl)pyrazolo[1,5-a]-pyrimidin-5-yloxy)piperidine-1-carboxylate (Int-11c)

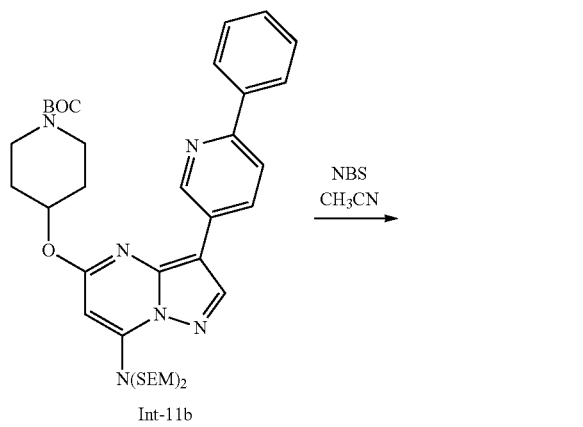

NBS (246 mg, 1.38 mmoL) was added to a solution of tert-butyl 4-(7-(bis((2-(trimethylsilyl)ethoxy)methyl)amino)-3-(6-phenylpyridin-3-yl)pyrazolo[1,5-a]pyrimidin-5-yloxy)piperidine-1-carboxylate (Int-11b, 1022 mg, 1.38 mmoL) in CH$_3$CN (15 mL). After stirring at room temperature for 30 min, the mixture was concentrated in vacuo. Purification by column chromatography afforded tert-butyl 4-(7-(bis((2-(trimethylsilyl)ethoxy)methyl)amino)-6-bromo-3-(6-phenylpyridin-3-yl)pyrazolo[1,5-a]pyrimidin-5-yloxy) piperidine-1-carboxylate (Int-11c): LCMS t$_R$=3.59 Min (5 min run, UV$_{254nm}$). Mass calculated for, M+824.3, observed m/z 825.1 (M+H).

Step D—Synthesis of 3-(6-phenylpyridin-3-yl)-5-(piperidin-4-yloxy)-8H-pyrazolo[1,5-a]pyrrolo[3,2-e]pyrimidine (Int-11e)

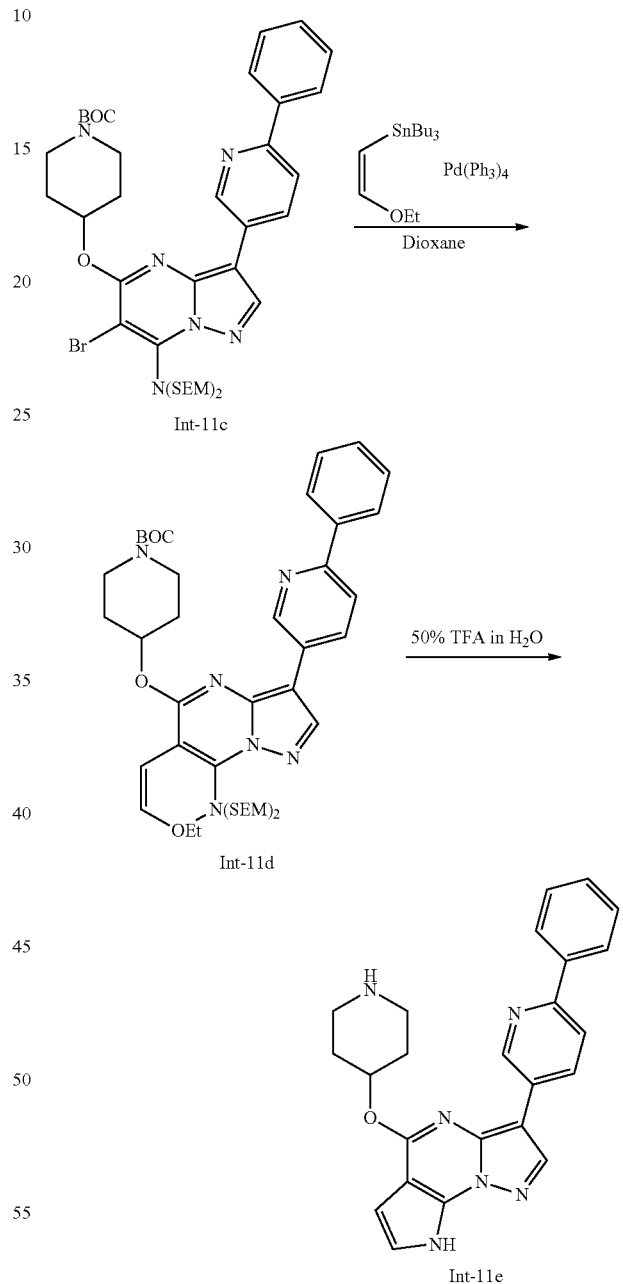

A degassed mixture of tert-butyl 4-(7-(bis((2-(trimethylsilyl)ethoxy)methyl)amino)-6-bromo-3-(6-phenylpyridin-3-yl)pyrazolo[1,5-a]pyrimidin-5-yloxy)piperidine-1-carboxylate (Int-11c, 0.26 mmol, 216 mg), Pd(PPh$_3$)$_4$ (30 mg, 0.026 mmoL), (Z)-tributyl(2-ethoxyvinyl)stannane (142 mg, 0.39 mmoL) in Dioxane (6 mL) was heated at 100° C. overnight. The reaction mixture was cooled to room temperature, filtered through 9:1 SiO$_2$:KF plug and concentrated in vacuo.

The crude (Z)-ethyl 2-(4-(7-(bis((2-(trimethylsilyl)ethoxy) methyl)amino)-6-(2-ethoxyvinyl)-3-(6-phenylpyridin-3-yl) pyrazolo[1,5-a]pyrimidin-5-yl)cyclohexyl)acetate (Int-11d) was treated with 50% TFA in H$_2$O (6 mL) and stirred overnight. The reaction mixture was concentrated in vacuo. Purification with prep-LC provided 3-(6-phenylpyridin-3-yl)-5-(piperidin-4-yloxy)-8H-pyrazolo[1,5-a]pyrrolo[3,2-e]pyrimidine (Int-11e): LCMS $t_R$=2.71 Min (10 min run, UV$_{254nm}$). Mass calculated for, M+410.1, observed m/z 411.1 (M+H).

Step E—Synthesis of 3-(6-phenylpyridin-3-yl)-5-(piperidin-4-yloxy)-8H-pyrazolo[1,5-a]pyrrolo[3,2-e]pyrimidine (Compound 35)

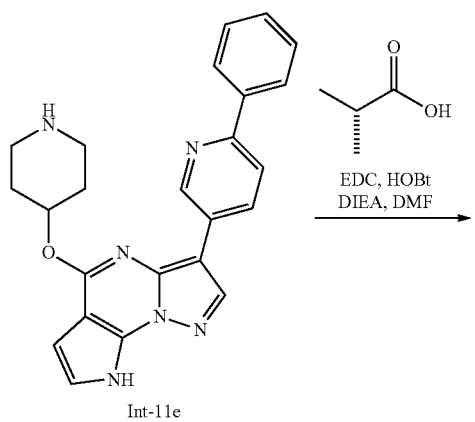

A mixture of 3-(6-phenylpyridin-3-yl)-5-(piperidin-4-yloxy)-8H-pyrazolo[1,5-a]pyrrolo[3,2-e]pyrimidine (Int-11e, 95.8 mg, 0.23 mmoL), D-(−)-lactic acid (25 mg, 0.28 mmoL), EDC (89 mg, 0.47 mmoL), HOBt (63 mg, 0.47 mmoL) and DIEA (244 uL, 1.46 mmoL) in DMF (4 mL) were stirred at room temperature for 2 hr. Purification with prep-LC provided (R)-2-hydroxy-1-(4-(3-(6-phenylpyridin-3-yl)-8H-pyrazolo[1,5-a]pyrrolo[3,2-e]pyrimidin-5-yloxy)piperidin-1-yl)propan-1-one (35): LCMS $t_R$=3.48 Min (10 min run, UV$_{254nm}$). Mass calculated for, M+482.2, observed m/z 483.2 (M+H).

Example 12

Preparation of Compound 33

Step A—Synthesis of tert-butyl 4-(2-methoxy-2-oxoethyl)piperidine-1-carboxylate (Int-12a)

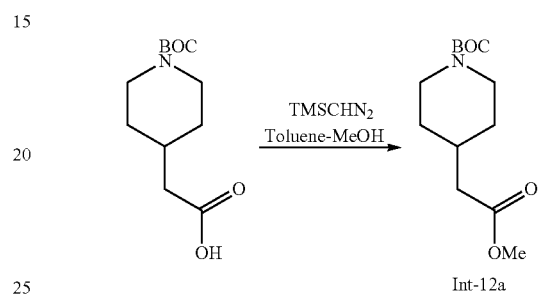

At 0° C., TMSCHN$_2$ (2.0 M in ether, 15 mL) was added dropwise to a mixture of 2-(1-(tert-butoxycarbonyl)piperidin-4-yl)acetic acid (6272 mg, 25.78 mmoL) in toluene (60 mL) and MeOH (60 mL). After stirring at room temperature for 1 h, the mixture was concentrated. The crude tert-butyl 4-(2-methoxy-2-oxoethyl)piperidine-1-carboxylate (Int-12a) was pure enough without further purification.

Step B—Synthesis of tert-butyl 4-((7-(bis((2-(trimethylsilyl)ethoxy)methyl)amino)pyrazolo[1,5-a]pyrimidin-5-yl)methyl)piperidine-1-carboxylate (Int-12d)

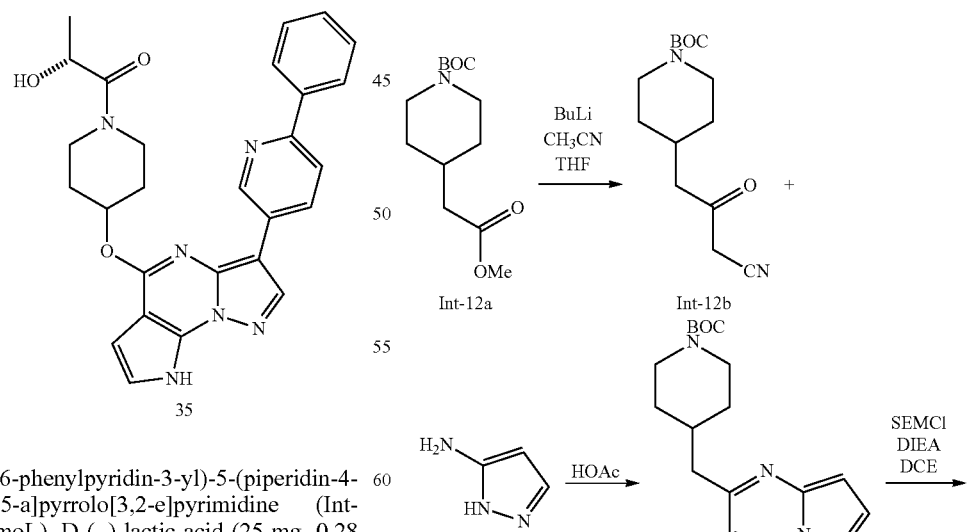

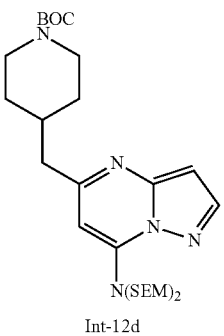

Int-12d

At −78° C., CH₃CN in THF (1505 uL, 28.82 mmoL) was added dropwise to n-BuLi (2.5 M in hexane, 11.52 mL) in THF (40 mL). After stirring at −78° C. for 1 h, tert-butyl 4-(2-methoxy-2-oxoethyl)piperidine-1-carboxylate (Int-12a, 3708 mg, 14.41 mmoL) in THF (10 mL) was added dropwise in 5 min. The mixture was stirred at −78° C. for 1 h and −45° C. for 1 h. At 0° C., 1N HCl was added carefully to adjust the pH to about 7. The mixture was then extracted with ethyl acetate (x2). The combined organic layers were washed with brine and dried with Na₂SO₄. Evaporation afforded tert-butyl-4-(3-cyano-2-oxopropyl)piperidine-1-carboxylate (Int-12b) which was then heated at 100° C. overnight with 1H-pyrazol-5-amine (1197 mg, 14.41 mmoL) in HOAc (25 mL). Concentration provided crude tert-butyl 4-((7-aminopyrazolo[1,5-a]pyrimidin-5-yl)methyl)piperidine-1-carboxylate (Int-12c) which was treated with SEMCl (72.05 mmoL, 12.71 mL) and DIEA (144.4 mmoL, 25.05 mL) in DCE (100 mL) at 50° C. for 1 h. The mixture was diluted with H₂O and then extracted with CH₂Cl₂ (x2). The combined organic layers were washed with brine and dried with Na₂SO₄. Evaporation and purification by column chromatography afforded tert-butyl 4-((7-(bis((2-(trimethylsilyl)ethoxy)methyl)amino)pyrazolo[1,5-a]pyrimidin-5-yl)methyl)piperidine-1-carboxylate (Int-12d): LCMS $t_R$=3.05 Min (5 min run, $UV_{254nm}$). Mass calculated for, M+591.3, observed m/z 592.3 (M+H).

Step C—Synthesis of tert-butyl 4-((7-(bis((2-(trimethylsilyl)ethoxy)methyl)amino)-3-iodopyrazolo[1,5-a]pyrimidin-5-yl)methyl)piperidine-1-carboxylate (Int-12e)

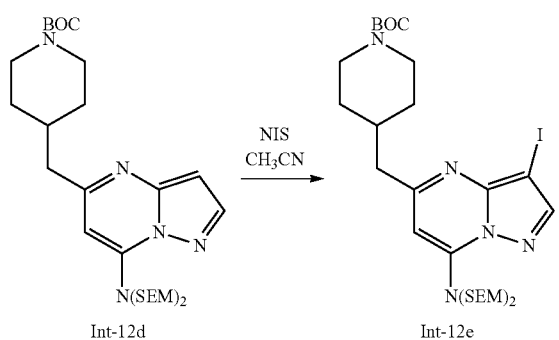

NIS (288 mg, 1.28 mmoL) was added to a solution of tert-butyl 4-((7-(bis((2-(trimethylsilyl)ethoxy)methyl)amino)pyrazolo[1,5-a]pyrimidin-5-yl)methyl)piperidine-1-carboxylate (Int-12d, 741.6 mg, 1.25 mmoL) in CH₃CN (10 mL). The mixture was stirred at room temperature for 1 h. Purification by column chromatography afforded tert-butyl 4-((7-(bis((2-(trimethylsilyl)ethoxy)methyl)amino)-3-iodopyrazolo[1,5-a]pyrimidin-5-yl)methyl)piperidine-1-carboxylate (Int-12e): LCMS $t_R$=3.02 Min (5 min run, $UV_{254nm}$). Mass calculated for, M+717.2, observed m/z 718.3 (M+H).

Step D—Synthesis of tert-butyl 4-((7-(bis((2-(trimethylsilyl)ethoxy)methyl)amino)-3-(6-phenylpyridin-3-yl)pyrazolo[1,5-c]pyrimidin-5-yl)methyl)piperidine-1-carboxylate (Int-12f)

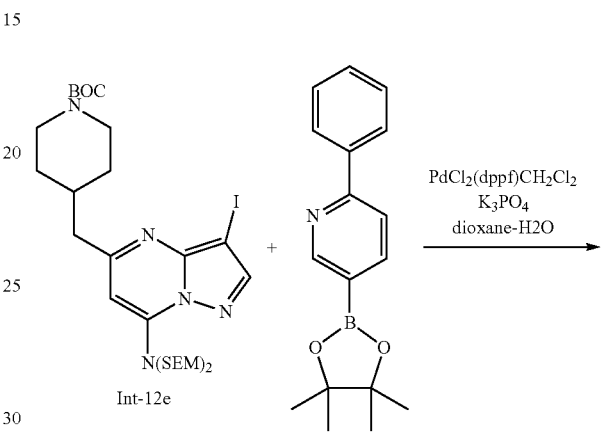

Int-12f 2-phenyl-5-(4,4,5,5-tetramethyl-1,3,2-dioxaborolan-2-yl)pyridine (1.32 mmol, 370 mg), K₃PO₄ (3.04 mmol, 644 mg), and PdCl₂(dppf).CH₂Cl₂ (0.10 mmol, 83 mg) was added to a solution of tert-butyl 4-((7-(bis((2-(trimethylsilyl)ethoxy)methyl)amino)-3-iodopyrazolo[1,5-a]pyrimidin-5-yl)methyl)piperidine-1-carboxylate (Int-12e, 1.02 mmol, 726 mg) in dioxane (6 mL) and H₂O (1 mL). The resulting solution was stirred at 100° C. under argon for 18 hours. The mixture was diluted with H₂O and then extracted with ethyl acetate (x2). The combined organic layers were washed with brine and dried with Na₂SO₄. Evaporation and purification by column chromatography afforded tert-butyl 4-((7-(bis((2-(trimethylsilyl)ethoxy)methyl)amino)-3-(6-phenylpyridin-3-yl)pyrazolo[1,5-a]pyrimidin-5-yl)methyl)piperidine-1- carboxylate (Int-12f): LCMS $t_R$=3.47 Min (5 min run, $UV_{254nm}$). Mass calculated for, M+744.2, observed m/z 745.2 (M+H).

Step E—Synthesis of (R)-2-hydroxy-1-(4-((3-(6-phenylpyridin-3-yl)-8H-pyrazolo[1,5-a]pyrrolo[3,2-e]pyrimidin-5-yl)methyl)piperidin-1-yl)propan-1-one (Compound 33)

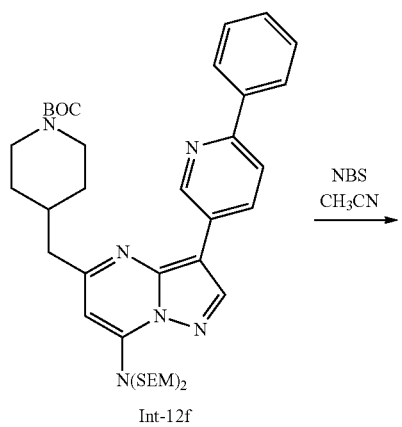

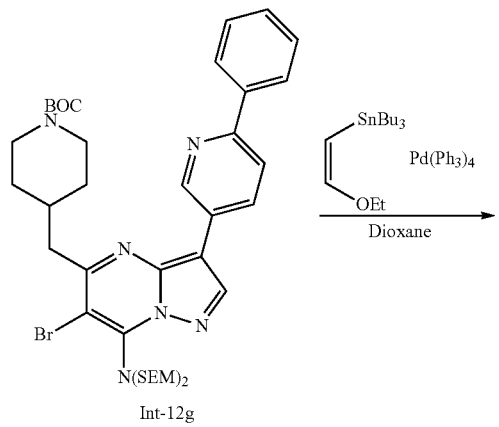

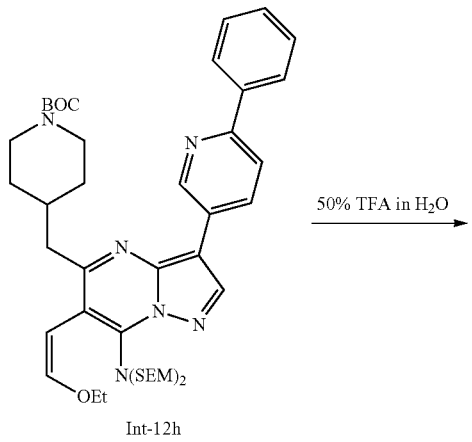

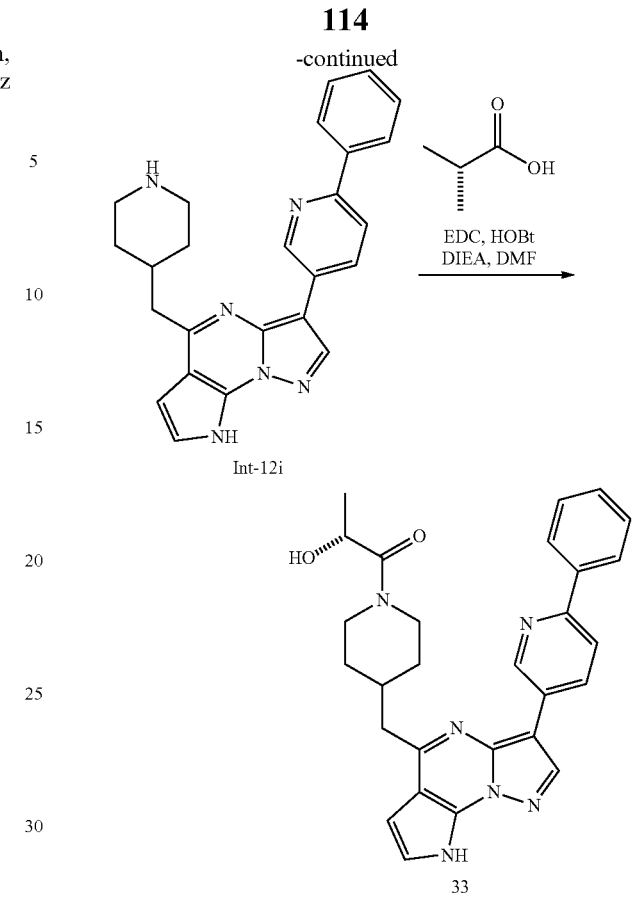

Applying similar reaction conditions as were used in Steps C-E of Example 11, (R)-2-hydroxy-1-(4-((3-(6-phenylpyridin-3-yl)-8H-pyrazolo[1,5-a]pyrrolo[3,2-e]pyrimidin-5-yl)methyl)piperidin-1-yl)propan-1-one (33) was synthesized from Int-12f: LCMS $t_R$=3.50 Min (10 min run, $UV_{254nm}$). Mass calculated for, M+480.2, observed m/z 481.2 (M+H).

Example 13

Preparation of Compounds 15, 10, and 16

Step A—Synthesis of Int-13a

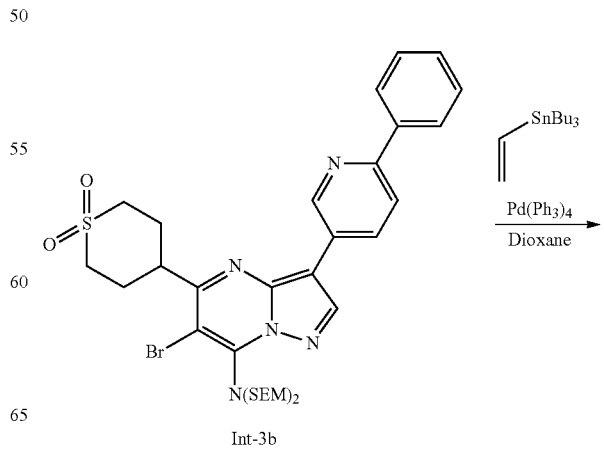

-continued

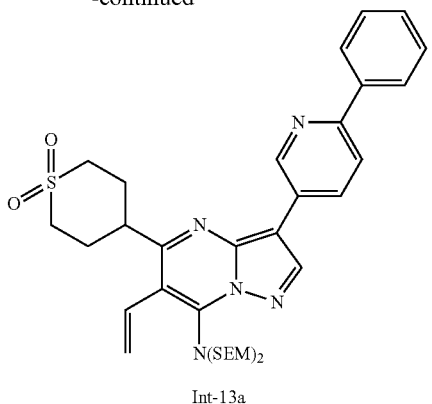

Int-13a

A degassed mixture of Int-3b (203 mg, 0.27 mmol), Pd(PPh$_3$)$_4$ (31 mg, 0.027 mmoL), tributyl(vinyl)stannane (255 mg, 0.80 mmoL) in CH$_3$CN (6 mL) was heated at 150° C. under microwave condition for 60 min. The reaction mixture was cooled to room temperature, filtered through 9:1 SiO$_2$:KF plug and concentrated in vacuo. Purification by column chromatography afforded Int-13a: LCMS t$_R$=2.82 Min (5 min run, UV$_{254nm}$). Mass calculated for, M+705.3, observed m/z 706.3 (M+H).

Step B—Synthesis of Int-13b

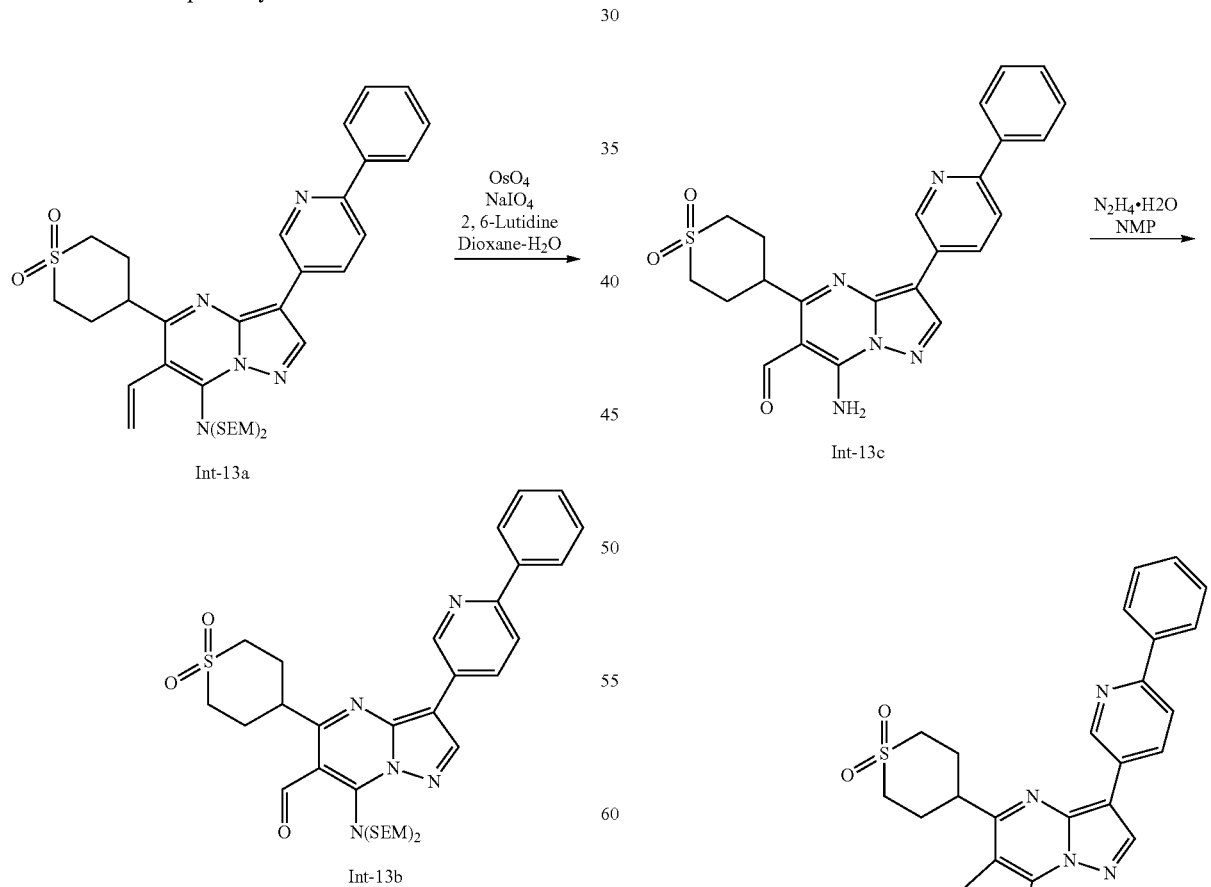

Int-13a

Int-13b

Int-13c

To Int-13a (189 mg, 0.26 mmol) in 1,4-dioxane (3 mL) was added 2.5 wt % OsO$_4$ in 1,4-dioxane (168 uL, 0.013 mmol), 2,6-lutidine (265 uL, 2.68 mmol) and H$_2$O (1 mL) and the resulting mixture was stirred at room temperature for 20 minutes. NaIO$_4$ (287 mg, 1.34 mmol) was then added and stirring at room temperature continued for 4 days. Saturated Na$_2$S$_2$O$_3$ solution (5 mL) was added and the mixture stirred for 10 minutes. Organics were then extracted with CH$_2$Cl$_2$ (2×), dried (Na$_2$SO$_4$) and concentrated in vacuo to afford Int-13b, which was used without further purification: LCMS t$_R$=2.87 Min (5 min run, UV$_{254nm}$). Mass calculated for, M+707.2, observed m/z 708.3 (M+H).

Step C—Synthesis of Compound 15

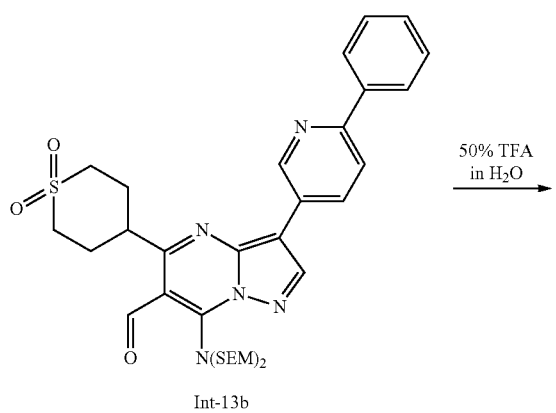

Int-13b

15

The crude Int-13b (150 mg, 0.21 mmoL) was treated with 50% TFA in H$_2$O (4 mL) until the disappearance of starting material in LCMS. Concentration and purification by prep-LC afforded compound Int-13c, LCMS t$_R$=3.10 Min (10 min run, UV$_{254nm}$). Mass calculated for, M+447.1, observed m/z 448.1 (M+H).

Int-13c (10.1 mg, 0.022 mmoL) was then heated under microwave condition with N$_2$H$_4$.H$_2$O (100 uL) and NMP (1 mL) first at 100° C. for 30 min and then at 200° C. for 1 h. Purification with prep-LC provided compound 15: LCMS t$_R$=2.92 Min (10 min run, UV$_{254nm}$). Mass calculated for, M+444.1, observed m/z 445.1 (M+H).

Preparation of Compounds 10 and 16

By essentially the same procedures detailed above for Step A of Example 3, and Steps A-D of this example, compounds 10 and 16 were prepared from Int-1g. For the preparation of compound 10, 5-(4,4,5,5-tetramethyl-1,3,2-dioxaborolan-2-yl)-2,3'-bipyridine was used in place of 2-phenyl-5-(4,4,5,5-tetramethyl-1,3,2-dioxaborolan-2-yl)pyridine in the palladium-catalyzed coupling step. For the preparation of compound 16, 5-fluoro-3-(4,4,5,5-tetramethyl-1,3,2-dioxaborolan-2-yl)quinoline was used in place of 2-phenyl-5-(4,4,5,5-tetramethyl-1,3,2-dioxaborolan-2-yl)pyridine in the palladium-catalyzed coupling step.

LC/MS data for compounds 10 and 16 are set forth below.

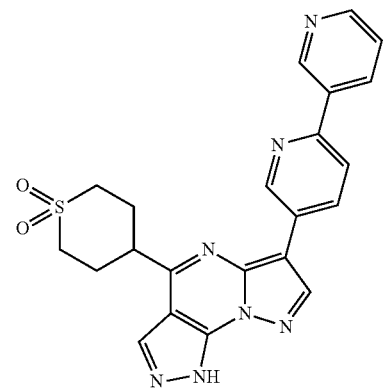

10

Compound 10: LCMS t$_R$=2.38 Min (10 min run, UV$_{254nm}$). Mass calculated for, M+445.1, observed m/z 446.1 (M+H).

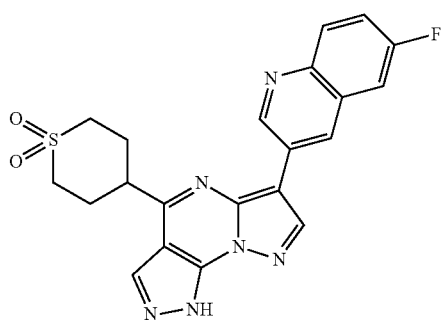

16

Compound 16: LCMS t$_R$=3.44 Min (10 min run, UV UV$_{254nm}$) Mass calculated for, M+436.1, observed m/z 437.0 (M+H).

Example 14

Preparation of Compounds 9, 11, and 14

Preparation of Compound 9

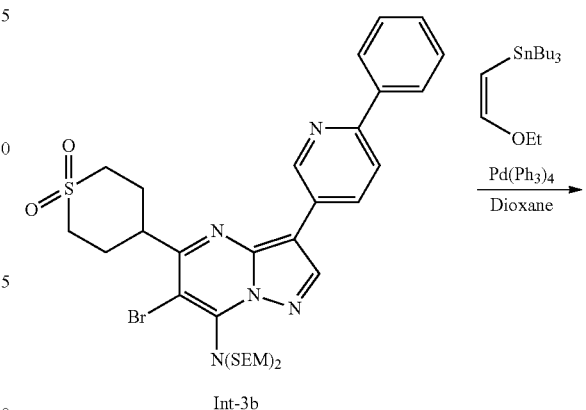

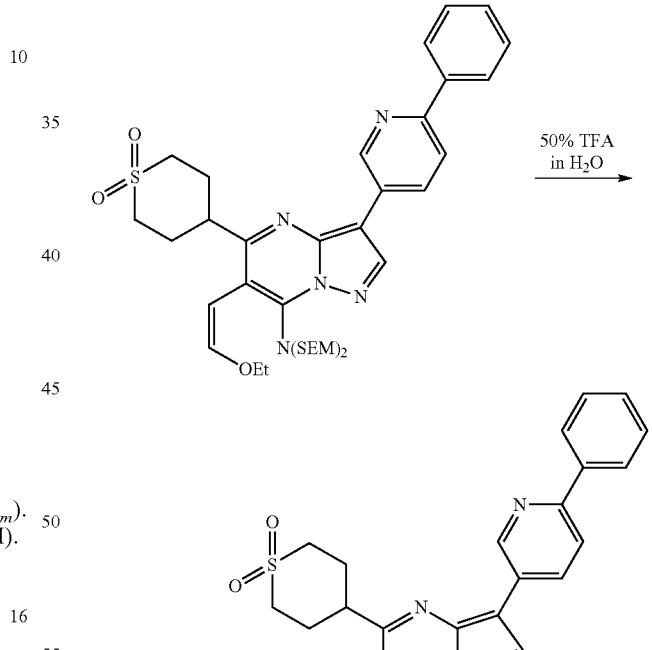

The preparation of compound 9 from Int-3b is summarized in the above scheme. Applying similar reaction conditions as were used to prepare Int-11e from Int-11d in Step D of Example 11, compound 9 was prepared from Int-3b. For compound 9: LCMS $t_R$=3.26 Min (10 min run, $UV_{254nm}$). Mass calculated for, M+ 443.1, observed m/z 444.1 (M+H).

Preparation of Compound 11

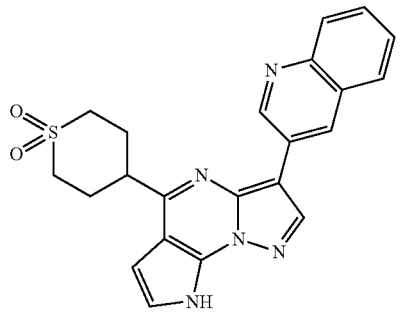

11

By essentially the same reaction conditions described for Step D of Example 11, compound 11 was prepared from Int-2b of Example 2. For compound 11: LCMS $t_R$=2.95 Min (10 min run, $UV_{254nm}$). Mass calculated for, M+417.1, observed m/z 418.1 (M+H).

Preparation of Compound 12

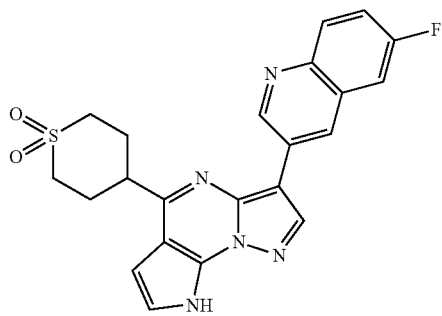

12

By essentially the same reaction conditions described in Step A of Example 3 and in Step D of Example 11, compound 12 was prepared from Int-1g of Example 1. In the preparation of compound 12, 5-fluoro-3-(4,4,5,5-tetramethyl-1,3,2-dioxaborolan-2-yl)quinoline was used in place of 2-phenyl-5-(4,4,5,5-tetramethyl-1,3,2-dioxaborolan-2-yl)pyridine in the palladium-catalyzed coupling step described in Step A of Example 3. For compound 12: LCMS $t_R$=3.26 Min (10 min run, $UV_{254nm}$). Mass calculated for, M+435.10, observed m/z 436.1 (M+H).

Preparation of Compound 14

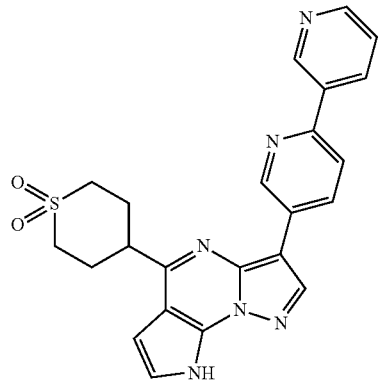

14

By essentially the same reaction conditions described in Step A of Example 3 and in Step D of Example 11, compound 14 was prepared from Int-1g of Example 1. In the preparation of compound 14, 2-(3-pyridyl)-(4,4,5,5-tetramethyl-1,3,2-dioxaborolan-2-yl)pyridine was used in place of 2-phenyl-5-(4,4,5,5-tetramethyl-1,3,2-dioxaborolan-2-yl)pyridine in the palladium-catalyzed coupling step described in Step A of Example 3. For compound 14: LCMS $t_R$=3.84 Min (10 min run, $UV_{254nm}$). Mass calculated for, M+452.0, observed m/z 453.0 (M+H).

Example 15

Preparation of Compounds 25, 24 and 27

Preparation of Compound 25

Step A—Synthesis of (Z)-tert-butyl 4-(7-(bis((2-(trimethylsilyl)ethoxy)methyl)amino)-6-(2-ethoxyvinyl)-3-(6-phenylpyridin-3-yl)pyrazolo[1,5-c]pyrimidin-5-yl)piperidine-1-carboxylate (Int-15a)

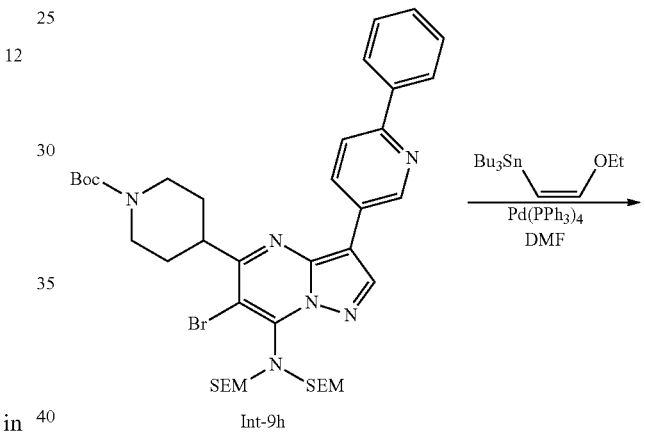

Int-9h

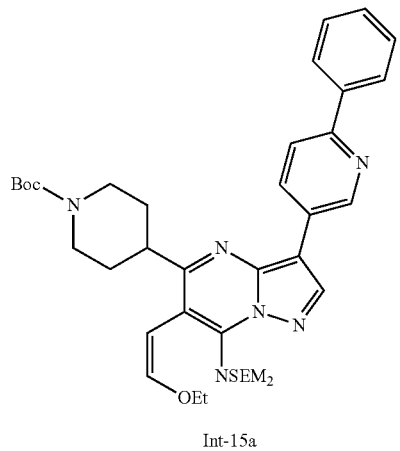

Int-15a (trimethylsilyl)ethoxy)methyl)amino)-6-bromo-3-(6-phenylpyridin-3-yl)pyrazolo[1,5-a]pyrimidin-5-yl)piperidine-1-carboxylate (Int-9h) (404 mg, 0.5 mmol) (synthesized as described in Steps A-H of Example 9), Z-1-ethoxy-2-(tributylstannyl)ethene, Pd(PPh₃)₄ (46 mg, 0.04 mmol) and DMF (2 mL). The tube was degassed with Ar briefly, capped and heated at 100° C. with stirring overnight. After cooling, the reaction mixture was diluted with EtOAc and water. The organic layer was isolated, washed with brine and dried (MgSO₄). After the solvent was removed under reduced pressure, the residue was purified on silica. Elution with EtOAc in hexanes (0-40%) gave the title compound (330 mg, 82%). LC/MS: m/z=801 (MH⁺).

Step B—Synthesis of 3-(6-phenylpyridin-3-yl)-5-(piperidin-4-yl)-8H-pyrazolo[1,5-a]pyrrolo[3,2-e]pyrimidine (Int-15b)

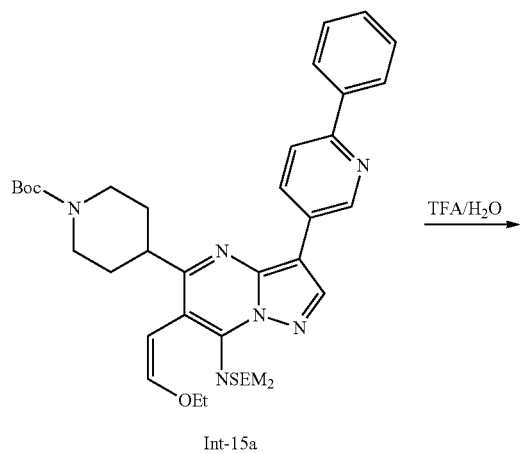

(Z)-tert-butyl 4-(7-(bis((2-(trimethylsilyl)ethoxy)methyl)amino)-6-(2-ethoxyvinyl)-3-(6-phenylpyridin-3-yl)pyrazolo[1,5-a]pyrimidin-5-yl)piperidine-1-carboxylate (Int-15a, 330 mg) was treated with TFA/water (1:1, 4 mL), stirred overnight, concentrated and lyophilized to provide the title compound as a TFA salt
LC/MS: m/z=395 (MH⁺).

Step C—Synthesis of (R)-2-hydroxy-1-(4-(3-(6-phenylpyridin-3-yl)-8H-pyrazolo[1,5-a]pyrrolo[3,2-e]pyrimidin-5-yl)piperidin-1-yl)propan-1-one (Compound 25)

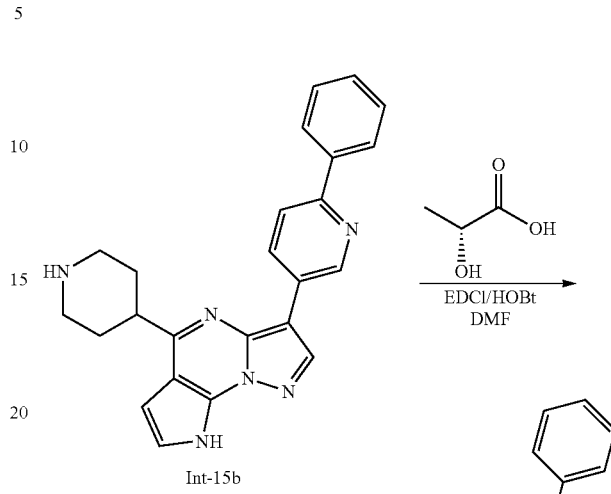

To a solution of 3-(6-phenylpyridin-3-yl)-5-(piperidin-4-yl)-8H-pyrazolo[1,5-a]pyrrolo[3,2-e]pyrimidine trifluoroacetic salt (Int-15b) (62 mg), N,N-diisopropylethylamine (70 μl) in DMF (1 mL) was added a solution of D-lactic acid (10 mg), N-(3-dimethylaminopropyl)-N'-ethyl-carbodiimide hydrochloride (19 mg) and 1-hydroxybenzotriazole (13 mg) in DMF (1 mL). The resulting mixture was stirred for a half hour and directly purified by HPLC to provide (R)-2-hydroxy-1-(4-(3-(6-phenylpyridin-3-yl)-8H-pyrazolo[1,5-a]pyrrolo[3,2-e]pyrimidin-5-yl)piperidin-1-yl)propan-1-one (25). LC/MS: m/z=467 (MH⁺).

Preparation of (R)-2,3-dihydroxy-1-(4-(3-(6-phenylpyridin-3-yl)-8H-pyrazolo[1,5-a]pyrrolo[3,2-e]pyrimidin-5-yl)piperidin-1-yl)propan-1-one (Compound 24)

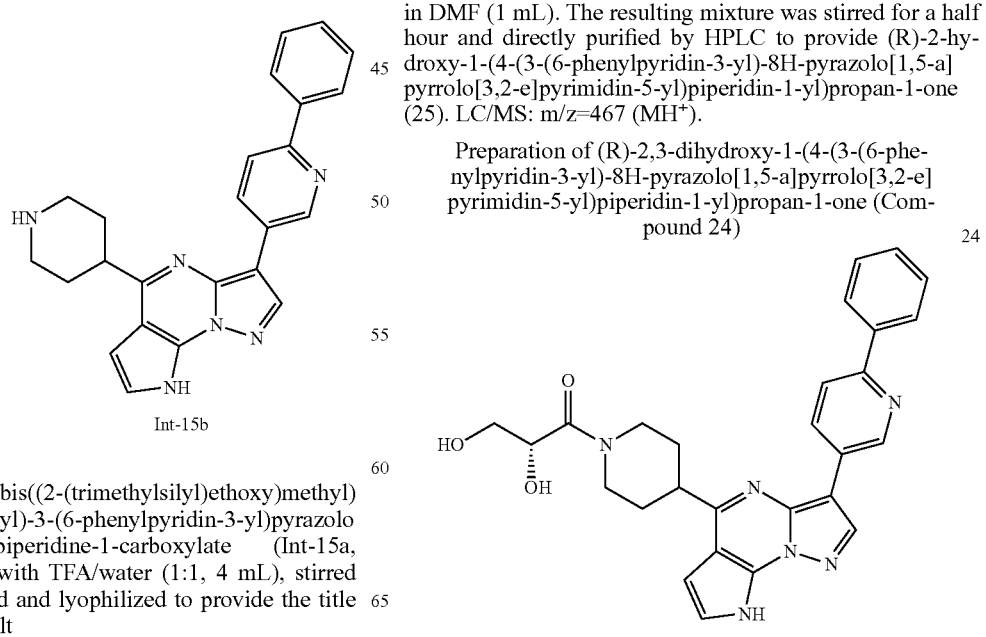

The title compound was prepared in a similar way to compound 25, except that (R)-2,3-dihydroxypropanoic acid was used in place of D-lactic acid in Step C. LC/MS (10 min method) RT: 2.63 min, [M+]=482.21, [M+H]=483.21

Preparation of 5-(1-(methylsulfonyl)pyrrolidin-3-yl)-3-(6-phenylpyridin-3-yl)-8H-pyrazolo[1,5-a]pyrrolo[3,2-e]pyrimidine (Compound 27)

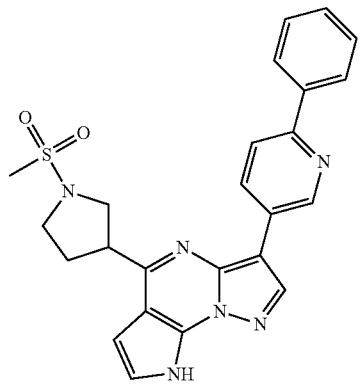

27

Compound 27 was prepared using synthetic steps similar to Steps A to D of Example 9 starting from Int-9d and Steps A-C of the present example. In the final step of the preparation, methyl sulfonyl chloride was used to sulfonylate the pyrrolidine nitrogen. LC/MS (10 min method) R$_t$: 3.51 Min. [M+]=458.15, [M+H]=459.57.

Example 16

Preparation of Compounds 34, 32, and 31

Preparation of Compound 34

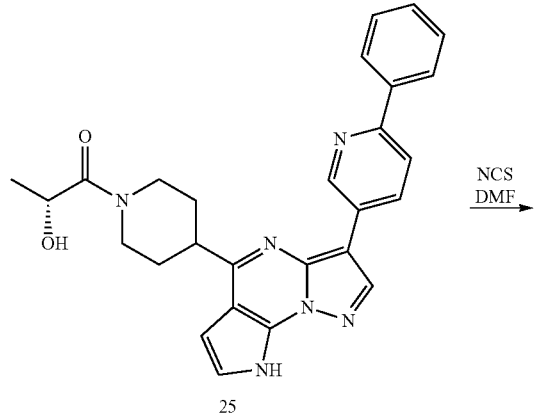

25

NCS
DMF
→

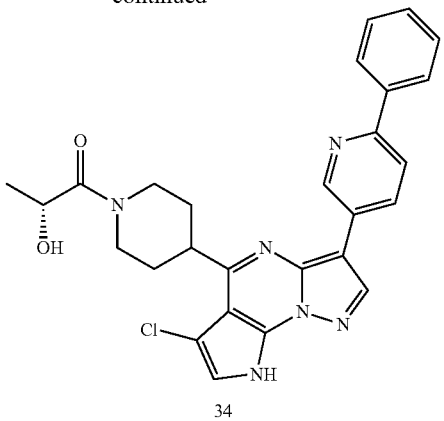

34

NCS (3.7 mg, 0.027 mmoL) was added to a solution of (R)-2-hydroxy-1-(4-(3-(6-phenylpyridin-3-yl)-8H-pyrazolo[1,5-a]pyrrolo[3,2-e]pyrimidin-5-yl)piperidin-1-yl)propan-1-one (25, prepared in Example 15) (12.8 mg, 0.027 mmoL) in DMF (1 mL). The mixture was stirred at room temperature for 3 days. Purification by prep-LC afforded (R)-1-(4-(6-chloro-3-(6-phenylpyridin-3-yl)-8H-pyrazolo[1,5-a]pyrrolo[3,2-e]pyrimidin-5-yl)piperidin-1-yl)-2-hydroxypropan-1-one (34): LCMS t$_R$=3.70 Min (10 min run, UV$_{254nm}$). Mass calculated for, M+500.1, observed 501.5 (M+H).

Preparation of Compound 32

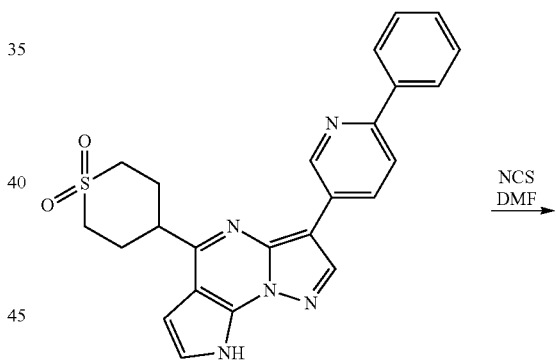

9

NCS
DMF
→

32

NCS (2.0 mg, 0.015 mmoL) was added to a solution of compound 9 (6.5 mg, 0.015 mmoL) in DMF (1 mL). The mixture was stirred at room temperature for one week. Purification by prep-LC afforded compound 32: LCMS $t_R$=3.51 Min (10 min run, $UV_{254nm}$). Mass calculated for, M+477.1, observed m/z 478.1 (M+H).

Preparation of Compound 31

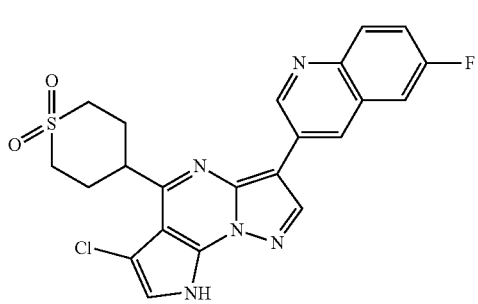

31

By essentially the same chlorination conditions described above in this example, compound 31 was prepared from compound 12 (described in Example 14).

LCMS $t_R$=3.58 Min (10 min run, $UV_{254nm}$). Mass calculated for, M+469.0, observed m/z 470.0 (M+H).

Example 17

Preparation of Compound 23

Step A—Synthesis of (trans)-tert-Butyl 4-(7-(bis((2-(trimethylsilyl)ethoxy)methyl)amino)-6-ethyl-3-(6-phenylpyridin-3-yl)pyrazolo[1,5-a]pyrimidin-5-yl)cyclohexanecarboxylate (Int-17a)

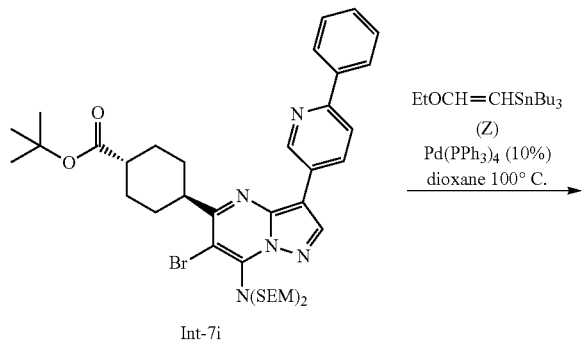

Int-7i

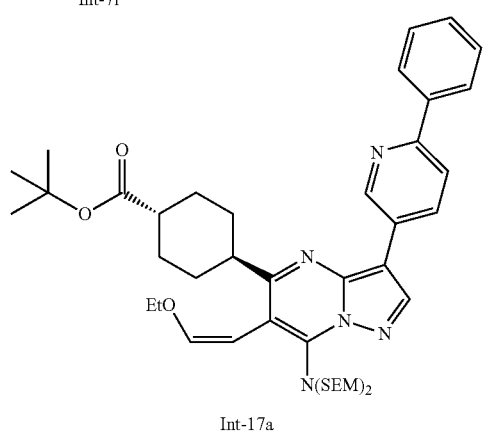

Int-17a

A mixture of Int-7i (prepared using steps A-J of Example 7), (Z)-1-ethoxy-2-(tributylstannyl)ethane, Pd(PPh$_3$)$_4$ in dioxane was stirred at 100° C. under Ar$_2$ for 8 h. After cooling to rt, the reaction mixture was passed through a short SiO$_2$/KF (9:1) plug to removed majority of the Sn species. The filtrate was concentrated and purified by a SiO$_2$ column (0-20% EtOAc/Hexanes) to afford the desired product (Int-17a) as a pale yellow oil (95.2 mg, 70%).

Step B—Synthesis of (trans)-4-(3-(6-phenylpyridin-3-yl)-8H-pyrazolo[1,5-a]pyrrolo[3,2-e]pyrimidin-5-yl)cyclohexanecarboxylic acid (Compound 23)

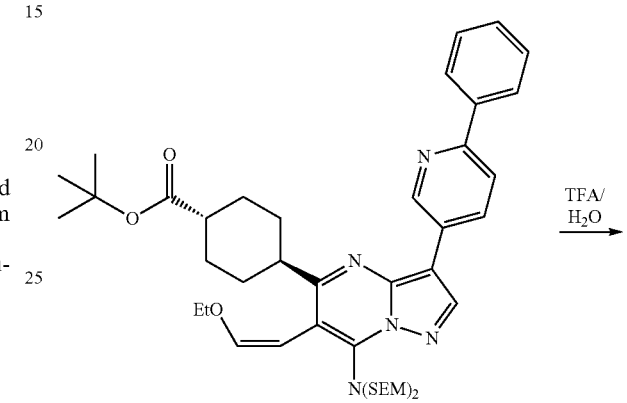

Int-17a

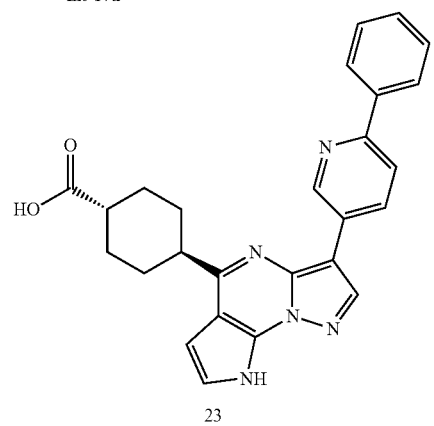

23

(trans)-tert-Butyl 4-(7-(bis((2-(trimethylsilyl)ethoxy)methyl)amino)-6-ethyl-3-(6-phenylpyridin-3-yl)pyrazolo[1,5-a]pyrimidin-5-yl)cyclohexanecarboxylate (Int-17a) was treated with a mixture of TFA/H$_2$O at rt overnight. The reaction mixture was evaporated to dryness and purified by a reverse phase HPLC (1120/CH$_3$CN, 0.2% FA). The product fraction was collected and concentrated. The residue was then treated with 1 N HCl (aq) and evaporated to dryness. This process was repeated one more time to afford the corresponding HCl salt of compound 23 as a pale yellow solid (42 mg, 81%).

LC/MS (10 min method): RT: 1.6 min (5 min run). Mass calculated for, M+H 438.19, observed 438.1854.

Example 18

Compound 28 was prepared as summarized in the reaction scheme below. The descriptions of the reaction conditions for each step follow the reaction scheme.

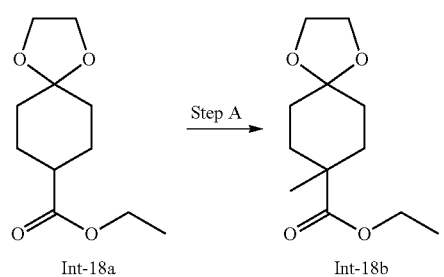
Int-18a → Step A → Int-18b → Step B →
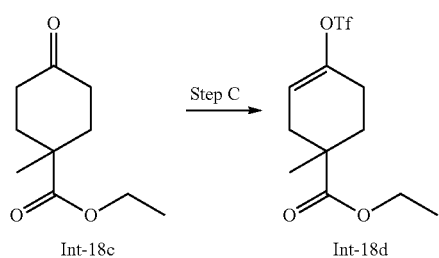
Int-18c → Step C → Int-18d → Step D →
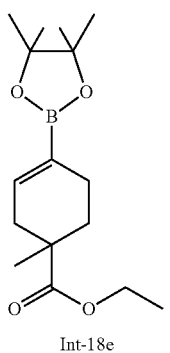
Int-18e
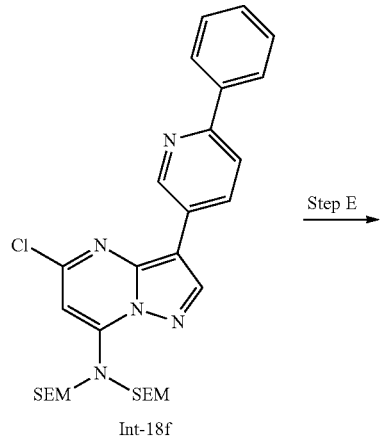
Int-18f → Step E →
-continued
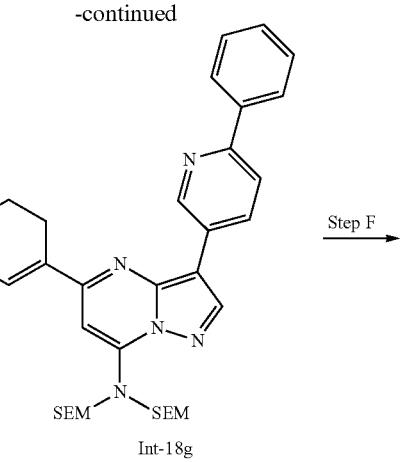
Int-18g → Step F →
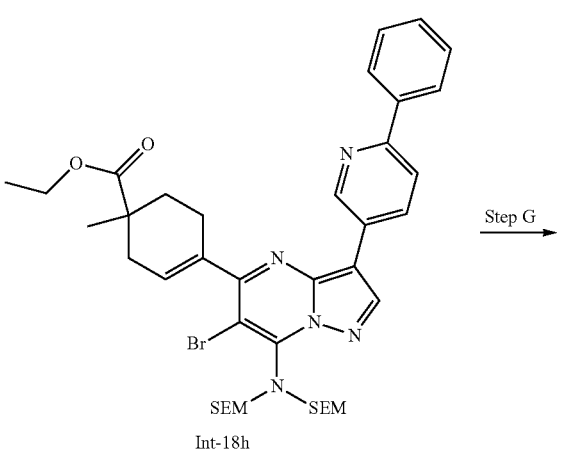
Int-18h → Step G →
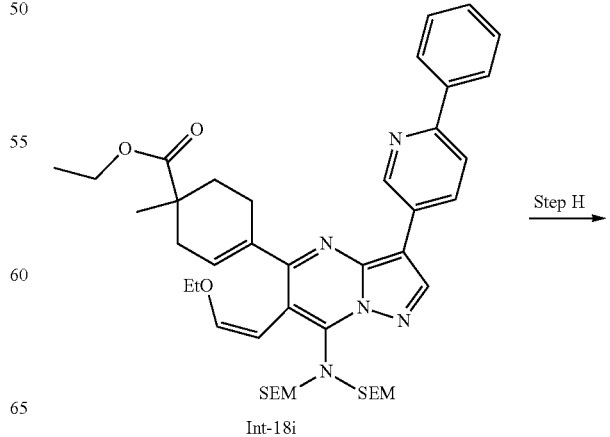
Int-18i → Step H →

-continued

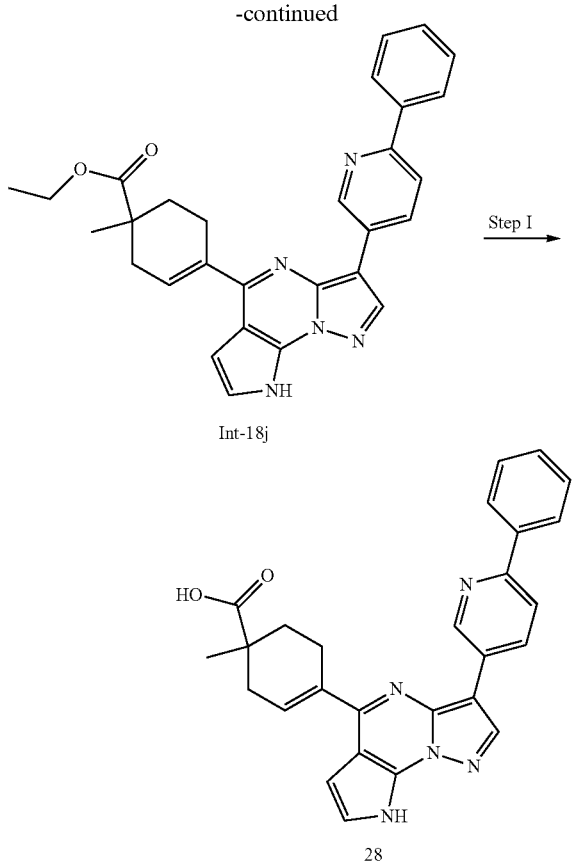

Int-18j

28

Step A—Synthesis of Int-18b

Ethyl 1,4-dioxaspiro[4.5]decane-8-carboxylate (Int-18a, 2.14 g, 10 mmol) was dissolved in dry THF (20 mL) and the solution was cooled to −78° C. LDA (1.8 M in THF, 6.6 mL) was added to the mixture dropwise and the mixture was stirred for 15 min. Then CH$_3$I (1.87 mL, 30 mmol) was added to the mixture at −78° C. and the reaction was allowed to warm up to room temperature. The reaction was stirred overnight. NH$_4$Cl (aq.) was added to quench the reaction which was extracted with ethyl acetate (50 mL×3). The combined organics was washed with water and brine and dried over Na$_2$SO$_4$. After concentration, the residue was purified by column chromatography (0-50% ethyl acetate in hexane) which gave ethyl 8-methyl-1,4-dioxaspiro[4.5]decane-8-carboxylate (Int-18b) (2.09 g) as an oil. HPLC-MS $t_R$=1.68 min (UV$_{254\ nm}$); mass calculated for formula C$_{12}$H$_{20}$O$_4$ 228.1, observed LCMS m/z 229.1 (M+H).

Step B—Synthesis of Int-18c

Ethyl 8-methyl-1,4-dioxaspiro[4.5]decane-8-carboxylate (Int-18b, 2.09 g, 9.17 mmol) was dissolved in acetonitrile (100 mL) and water (50 mL). Ammonium cerium nitrate (503 mg, 0.92 mmol) in water (50 mL) was added and the resulting mixture was heated up to 70° C. and stirred for 1 h. After being cooled down to room temperature, water (100 mL) was added and the mixture was extracted with ether (100 mL×3). The combined organics were washed with water, brine and dried. After concentration, the residue was purified on a column (silica gel, 0-30% ethyl acetate in hexane) which gave ethyl 1-methyl-4-oxocyclohexanecarboxylate (Int-18c) (1.72 g) as an oil.

Step C—Synthesis of Int-18d

Ethyl 1-methyl-4-oxocyclohexanecarboxylate (Int-18c, 2.65 g, 14.39 mmol) was dissolved in dry THF (10 mL) and added into LDA (17.28 mmol) in THF (20 mL) at −78° C. The resulting mixture was stirred for 30 min and N-phenyltrifluoromethanlsulfonimide (5.66 g, 15.8 mmol) on THF (10 mL) was added at −78° C. The resulting mixture was allowed to warm up to room temperature and stirred overnight. NH$_4$Cl (aq.) was added to quench the reaction which was extracted with ethyl acetate. The organics were dried and concentrated and purified on a column (silica gel, 0-30% EA in hexane) to give ethyl 1-methyl-4-(trifluoromethylsulfonyloxy)cyclohex-3-enecarboxylate (Int-18d) (3.36 g).

Step D—Synthesis of Int-18e

To a 100 mL round-bottom flask charged with ethyl 1-methyl-4-(trifluoromethylsulfonyloxy)cyclohex-3-enecarboxylate (Int-18d, 3.36 g, 10.63 mmol), Pd(dppf)Cl$_2$ (815 mg, 1.0 mmol), DPPF (554 mg, 1.0 mmol), KOAc (3.2 g, 33.0 mmol), and Bis(pinacolato)diboron (3.24 g, 12.76 mmol) was added dioxane (50 mL). The mixture was thoroughly degassed by alternately evacuating the flask under vacuum, then putting under argon atmosphere numerous times. The reaction mixture was then heated to 80° C. and stirred overnight. After cooling to room temperature, the reaction mixture was diluted with ethyl acetate (50 mL) and filtered through celite. The solvent was removed under reduced pressure and the residue was purified by column chromatography (silica gel, 0-30% ethyl acetate in hexane) which gave ethyl 1-methyl-4-(4,4,5,5-tetramethyl-1,3,2-dioxaborolan-2-yl)cyclohex-3-enecarboxylate (Int-18e, 2.03 g) as a white solid. HPLC-MS $t_R$=2.35 min (UV$_{254\ nm}$); mass calculated for formula C$_{16}$H$_{27}$BO$_4$ 294.2, observed LCMS m/z 295.3 (M+H).

Step E—Synthesis of Int-18f

To a 40 mL vial charged with 5-chloro-3-(6-phenylpyridin-3-yl)-N,N-bis((2-(trimethylsilyl)ethoxy)methyl)pyrazolo[1,5-a]pyrimidin-7-amine (Int-18e, 582 mg, 1.0 mmol), Pd(dppf)Cl$_2$ (82 mg, 0.1 mmol), K$_3$PO$_4$ (636 mg, 3.0 mmol), and ethyl 1-methyl-4-(4,4,5,5-tetramethyl-1,3,2-dioxaborolan-2-yl)cyclohex-3-enecarboxylate (441 mg, 1.5 mmol) was added dioxane (20 mL including 1 mL water). The mixture was thoroughly degassed by alternately evacuating the flask under vacuum, then placing it under an argon atmosphere numerous times. The reaction was then heated to 90° C. and stirred overnight. After cooling to room temperature, the reaction mixture was diluted with ethyl acetate (30 mL) and filtered through celite. The solvent was removed under reduced pressure and the residue was purified with column (silica gel, 0-30% ethyl acetate in hexane) gave ethyl 4-(7-(bis((2-(trimethylsilyl)ethoxy)methyl)amino)-3-(6-phenylpyridin-3-yl)pyrazolo[1,5-a]pyrimidin-5-yl)-1-methyl-cyclohex-3-enecarboxylate (Int-18f) (630 mg). HPLC-MS $t_R$=2.89 min (UV$_{254\ nm}$); mass calculated for formula C39H$_{55}$N$_5$O$_4$Si$_2$ 713.4, observed LCMS m/z 714.4 (M+H).

Step F—Synthesis of Int-18g

Ethyl 4-(7-(bis((2-(trimethylsilyl)ethoxy)methyl)amino)-3-(6-phenylpyridin-3-yl)pyrazolo[1,5-a]pyrimidin-5-yl)-1-methylcyclohex-3-enecarboxylate (Int-18f, 152 mg, 0.212 mmol) was dissolved in acetonitrile (5 mL) and NBS (38 mg, 0.212 mmol) was added. The mixture was stirred at room temperature for 3 h and then concentrated. The residue was purified with a column (silica gel, 0-30% ethyl acetate in hexane) which gave ethyl 4-(7-(bis((2-(trimethylsilyl)ethoxy)methyl)amino)-6-bromo-3-(6-phenylpyridin-3-yl)pyrazolo[1,5-a]pyrimidin-5-yl)-1-methylcyclohex-3-enecarboxylate (Int-18g) (139 mg). HPLC-MS $t_R$=3.04 min (UV$_{254\ nm}$); mass calculated for formula C39H54BrN5O4S$_{i2}$ 791.3, observed LCMS m/z 792.2 (M+H).

Step G—Synthesis of Int-18h

A mixture of ethyl 4-(7-(bis((2-(trimethylsilyl)ethoxy)methyl)amino)-6-bromo-3-(6-phenylpyridin-3-yl)pyrazolo[1,5-a]pyrimidin-5-yl)-1-methylcyclohex-3-enecarboxylate (Int-18g, 48 mg, 0.061 mmol), (Z)-1-ethoxy-2-(tributylstannyl)ethane (72 mg), Pd(PPh$_3$)$_4$ (11 mg, 0.01 mmol) in dioxane (3 ml) was stirred at 100° C. under Ar for 8 h. After cooling to rt, the reaction mixture was passed through a short SiO$_2$/KF (9:1) plug to removed majority of the Sn species. The filtrate was concentrated to give (Z)-ethyl 4-(7-(bis((2-(trimethylsilyl)ethoxy)methyl)amino)-6-(2-ethoxyvinyl)-3-(6-phenylpyridin-3-yl)pyrazolo[1,5-a]pyrimidin-5-yl)-1-methylcyclohex-3-enecarboxylate (Int-18h) which was used in the next step directly without further purification. HPLC-MS $t_R$=3.02 min (UV$_{254\ nm}$); mass calculated for formula C$_{43}$H$_{61}$N$_5$O$_5$Si$_2$ 783.4, observed LCMS m/z 784.2 (M+H).

Step H—Synthesis of Int-18i (Z)-Ethyl 4-(7-(bis((2-(trimethylsilyl)ethoxy)methyl)amino)-6-(2-ethoxyvinyl)-3-(6-phenylpyridin-3-yl)pyrazolo[1,5-a]pyrimidin-5-yl)-1-methylcyclohex-3-enecarboxylate (crude Int-18h) was treated with a mixture of 50% TFA/H$_2$O at rt overnight. The reaction mixture was evaporated to dryness and purified by Prep-LC to give ethyl 1-methyl-4-(3-(6-phenylpyridin-3-yl)-8H-pyrazolo[1,5-a]pyrrolo[3,2-e]pyrimidin-5-yl)cyclohex-3-enecarboxylate (Int-18i). HPLC-MS $t_R$=1.86 min (UV$_{254nm}$); mass calculated for formula C$_{29}$H$_{27}$N$_5$O$_2$ 477.2, observed LCMS m/z 478.3 (M+H).

Step I—Synthesis of Int-18j

Ethyl 1-methyl-4-(3-(6-phenylpyridin-3-yl)-8H-pyrazolo[1,5-a]pyrrolo[3,2-e]pyrimidin-5-yl)cyclohex-3-enecarboxylate (Int-18j, 19 mg) was dissolved in THF/Methanol (5 mL/2 mL) and LiOH (1N, 1 mL) was added. The mixture was heated to 45° C. and stirred overnight. The mixture was concentrated and water (2 mL) was added. The HCl (1N) was added to adjust the pH to around 6. The solid was collected with filtration and dried to give compound 28. HPLC-MS $t_R$=1.53 min (UV$_{254}$ nm); mass calculated for formula C$_{27}$H$_{23}$N$_5$O$_2$ 449.2, observed LCMS on/z 450.2 (M+H).

Example 19

Preparation of Compound 29

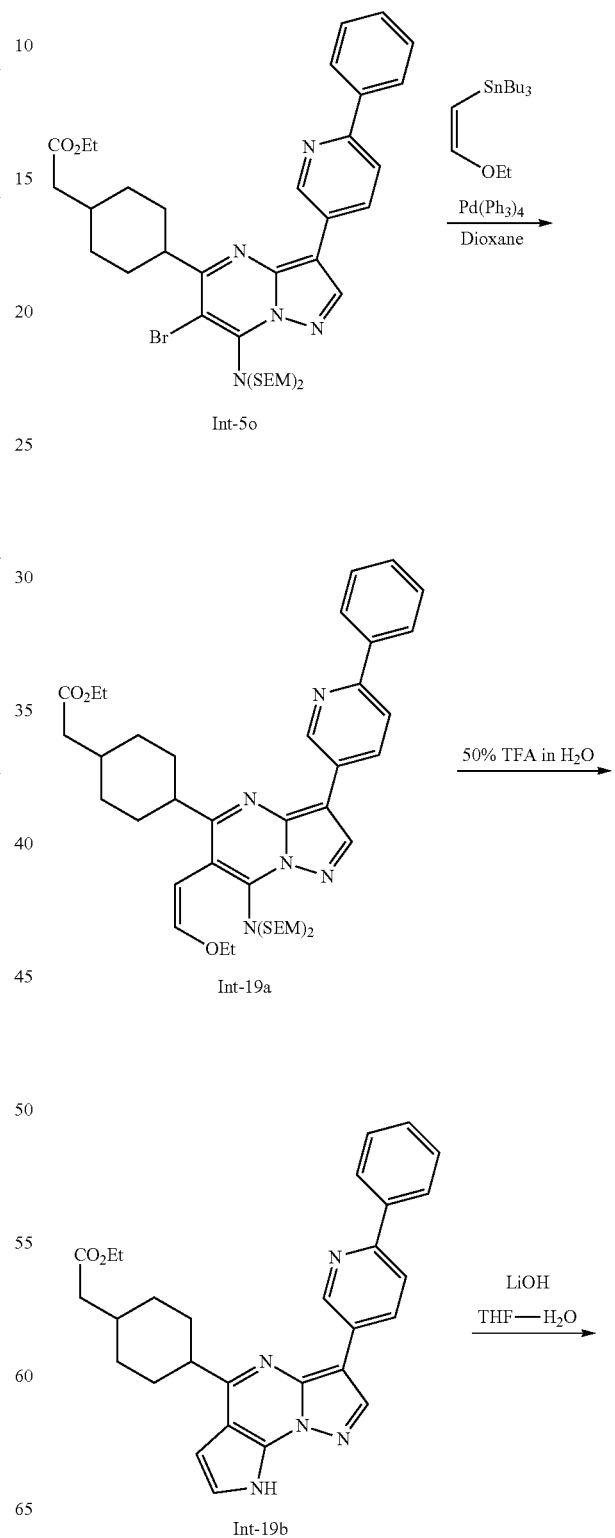

-continued

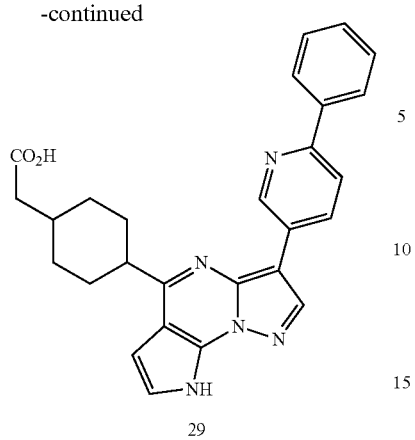

29

A degassed mixture of ethyl 2-(4-(7-(bis((2-(trimethylsilyl)ethoxy)methyl)amino)-6-bromo-3-(6-phenylpyridin-3-yl)pyrazolo[1,5-a]pyrimidin-5-yl)cyclohexyl)acetate (Int-5o from Example 5) (0.20 mmol, 161 mg), Pd(PPh₃)₄ (24 mg, 0.02 mmoL), (Z)-tributyl(2-ethoxyvinyl)stannane (110 mg, 0.30 mmoL) in dioxane (3 mL) was heated at 100° C. overnight. The reaction mixture was cooled to room temperature, filtered through 9:1 SiO₂:KF plug and concentrated in vacuo. The crude (Z)-ethyl 2-(4-(7-(bis((2-(trimethylsilyl)ethoxy)methyl)amino)-6-(2-ethoxyvinyl)-3-(6-phenylpyridin-3-yl)pyrazolo[1,5-a]pyrimidin-5-yl)cyclohexyl)acetate (Int-19a) was treated with 50% TFA in H₂O (4 mL) and stirred overnight. The reaction mixture was concentrated in vacuo. LiOH.H₂O (60 mg, 1.543 mmoL) was added to a mixture of the crude ethyl 2-(4-(3-(6-phenylpyridin-3-yl)-8H-pyrazolo[1,5-a]pyrrolo[3,2-e]pyrimidin-5-yl)cyclohexyl)acetate (Int-19b) in 2:1 THF:H₂O (3 mL). The resulting solution was stirred at room temperature overnight. The reaction mixture was concentrated and purified by prep-LC to afford the 24443-(6-phenylpyridin-3-yl)-8H-pyrazolo[1,5-a]pyrrolo[3,2-e]pyrimidin-5-yl)cyclohexyl) acetic acid (29) as a mixture of cis and trans isomers: LCMS $t_R$=3.93 Min (10 min run, $UV_{254nm}$). Mass calculated for, M+451.2, observed 452.6 (M+H).

Example 20

Preparation of Compound 36

This example describes one embodiment for incorporating a deuterium-bearing substituent at the 3-position of the fused tricyclic compound.

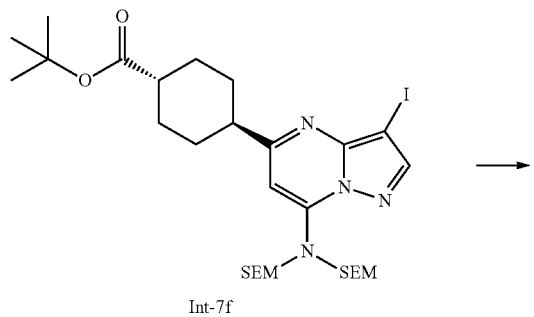

Int-7f

-continued

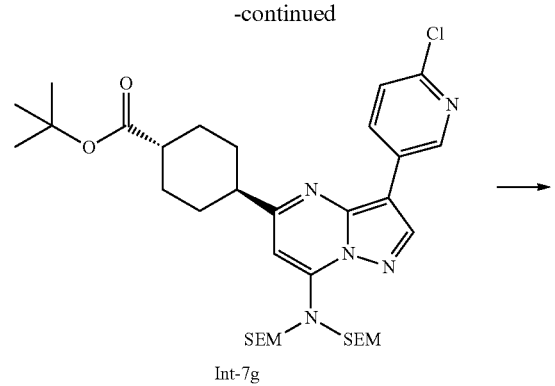

Int-7g

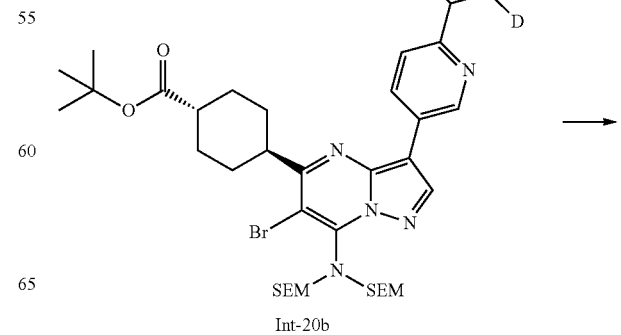

Int-20a

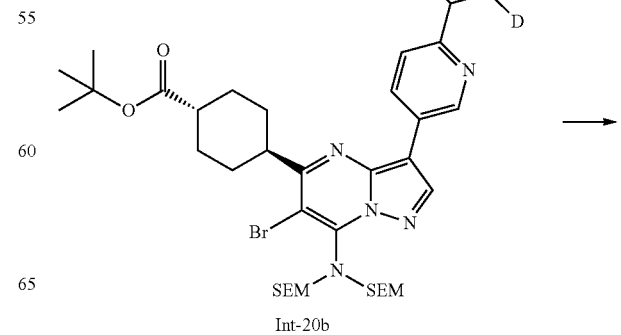

Int-20b

135
-continued

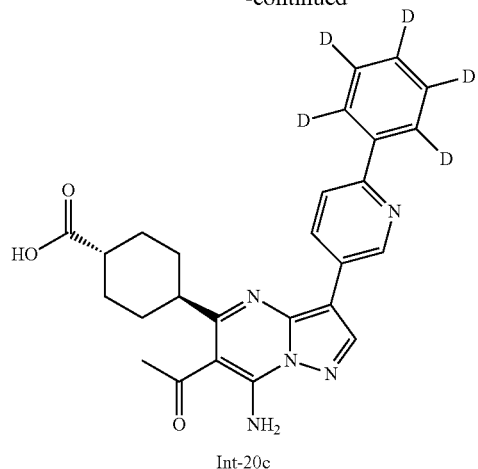
Int-20c

136
-continued

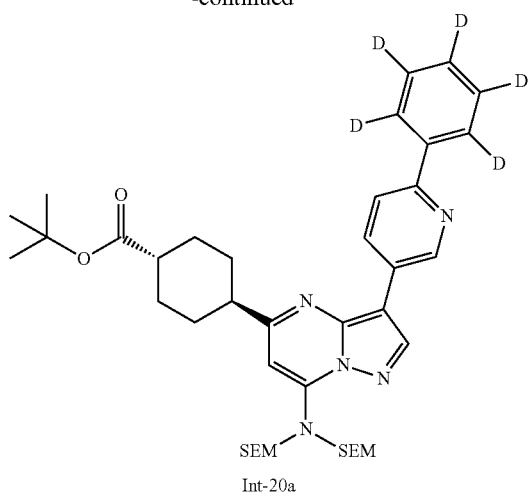
Int-20a

Tertiary butyl 4-(7-(bis((2-(trimethylsilyl)ethoxy)methyl)amino)-3-(6-chloropyridin-3-yl)pyrazolo[1,5-a]pyrimidin-5-yl)cyclohexanecarboxylate (Int-7g) is prepared according to Steps A-G of Example 7. Phenyl-$d_5$-boronic acid (1.08 mmol, 137 mg), $K_3PO_4$ (1.63 mmol, 345 mg), and $PdCl_2$(dppf), $CH_2Cl_2$ (0.054 mmol, 45 mg) is added to a solution of Int-7g (0.54 mmol, 350 mg) in dioxane (6.0 mL). To this suspension is added distilled $H_2O$ (0.6 mL). The resulting solution is stirred at 100° C. under argon for 18 hours. The reaction mixture is concentrated in vacuo and then purified via silica gel chromatography (0% to 60% ethyl acetate in hexanes gradient) to yield the title compound.

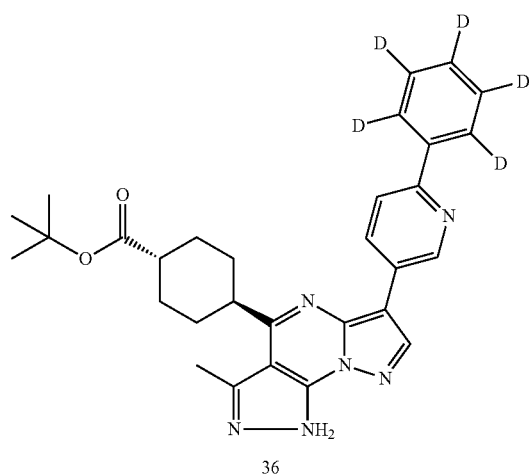
36

Step A—Synthesis of (1R,4R)-methyl 4-(7-(bis((2-(trimethylsilyl)ethoxy)methyl)amino)-3-(6-phenyl-$d_5$-pyridin-3-yl)pyrazolo[1,5-a]pyrimidin-5-yl)cyclohexanecarboxylate (Int-20a)

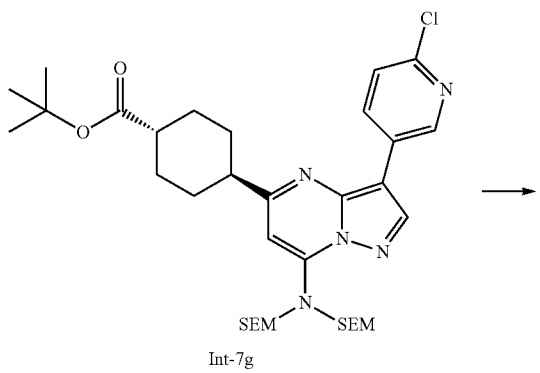
Int-7g

Step B—Synthesis of t-Butyl (1R,4R)-4-(7-amino-6-bromo-3-(6-phenyl-$d_5$-pyridin-3-yl)pyrazolo[1,5-a]pyrimidin-5-yl)cyclohexanecarboxylic acid (Int-20b)

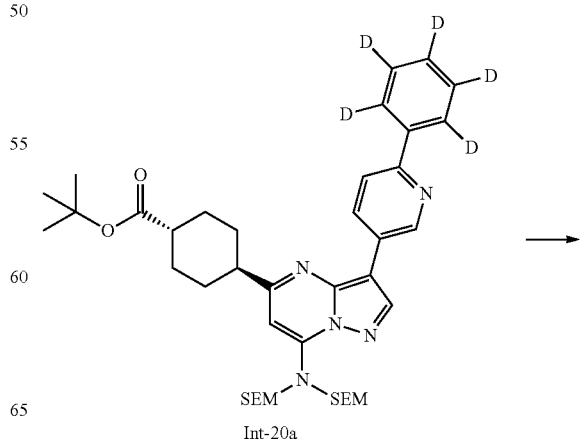
Int-20a

-continued

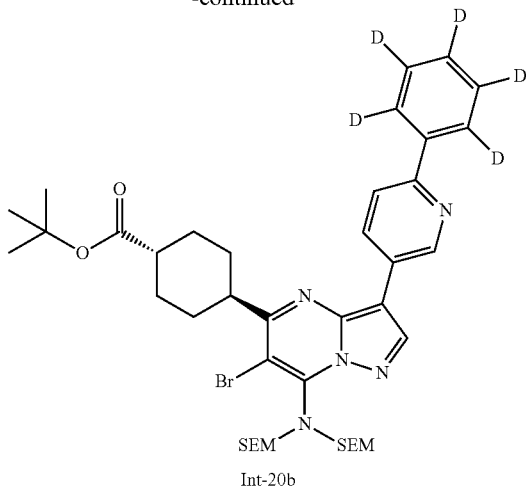
Int-20b

N-bromosuccinimide (73 mg, 0.41 mmol) is added to a solution of (1R,4R)-t-butyl 4-(7-(bis((2-(trimethylsilyl)ethoxy)methyl)amino)-3-(6-phenyl-d₅-pyridin-3-yl)pyrazolo[1,5-a]pyrimidin-5-yl)cyclohexanecarboxylate (Int-20a, 284 mg, 0.41 mmol) in acetonitrile (4 mL). The resulting solution is stirred at room temperature for 1 hour. The reaction mixture is concentrated in vacuo and purified by prep-LC to afford the title compound.

Step C—Synthesis of t-Bu 1 (1R,4R)-4-(7-amino-6-acetyl-3-(6-phenyl-d₅-pyridin-3-yl)pyrazolo[1,5-a]pyrimidin-5-yl)cyclohexanecarboxylic acid (Int-20c)

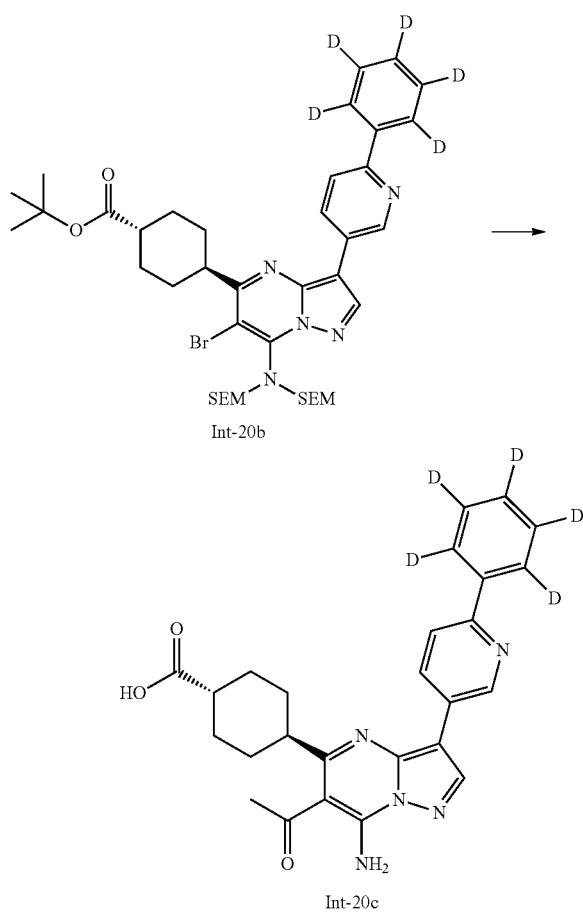

By essentially following the procedures described in Steps J and K of Example 7, Int-20b is converted to Int-20c.

Step D—Synthesis of t-Butyl (1R,4R)-4-(7-amino-6-acetyl-3-(6-phenyl-d₅-pyridin-3-yl)pyrazolo[1,5-a]pyrimidin-5-yl)cyclohexanecarboxylic acid (Compound 36)

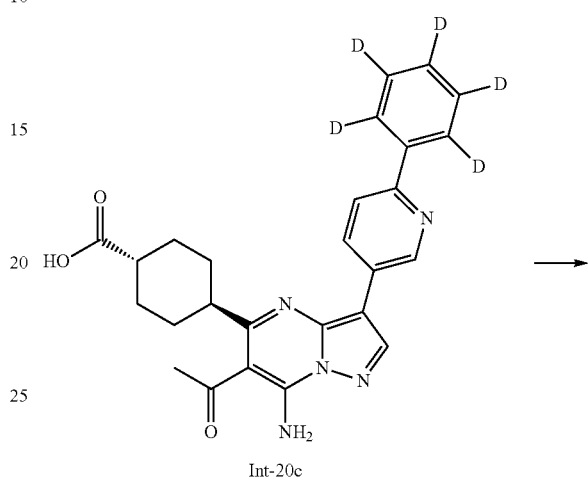

To a 20 mL scintillation vial is charged (1R,4R)-4-(6-acetyl-7-amino-3-(6-5d-phenylpyridin-3-yl)pyrazolo[1,5-a]pyrimidin-5-yl)cyclohexanecarboxylic acid (Int-20c, 50 mg, 0.11 mmol). To this vial is added NMP (0.5 mL) followed by hydrazine monohydrate (1 mL). The reaction is stirred at room temperature for 3 hours. The excess hydrazine monohydrate is removed in vacuo and the residue transferred into 2-5 mL microwave vessel. The vial is sealed and heated to 180° C. for 30 minutes in a microwave. The NMP is reduced in vacuo using chlorobenzene as a cosolvent. The residue is purified via reverse-phase preparatory HPLC to yield compound 36.

Example 21

Preparation of Compound 37

This example describes one embodiment for incorporating deuterium-bearing substituents at both the 3- and 5-positions of the fused tricyclic compound.

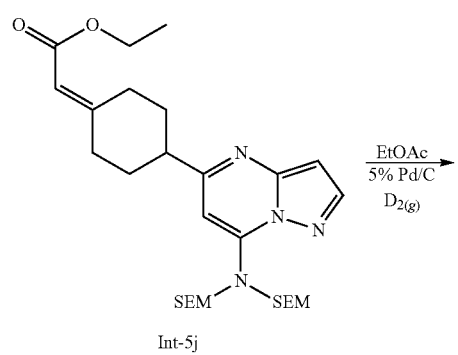
Int-5j
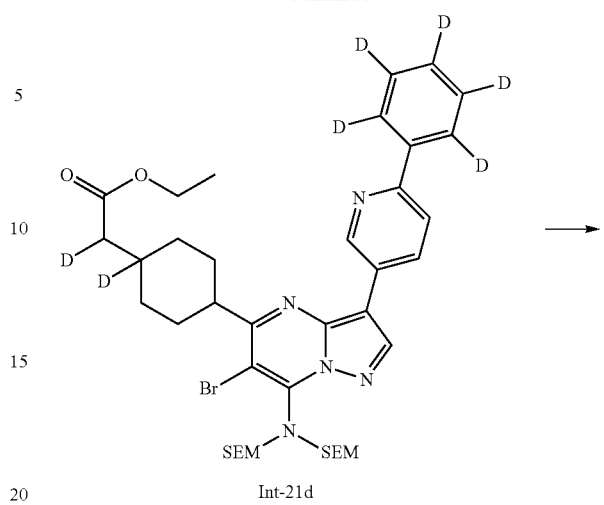
Int-21d
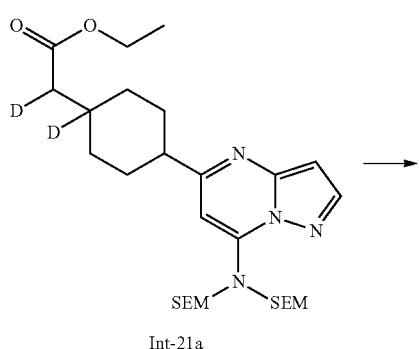
Int-21a
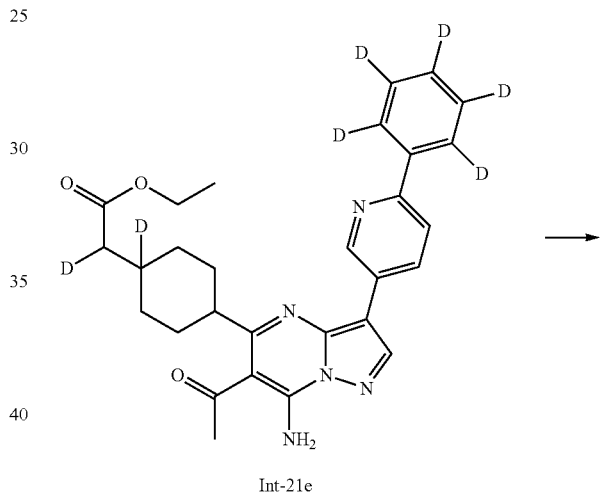
Int-21e
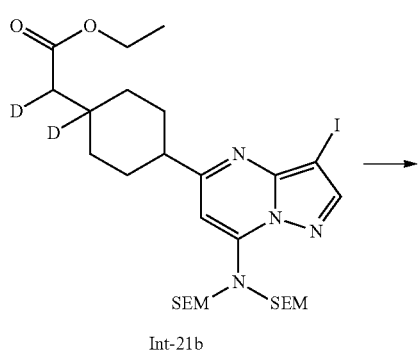
Int-21b
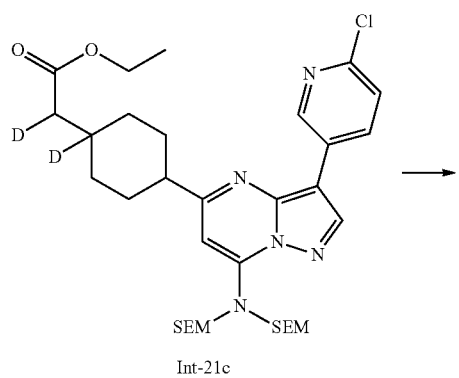
Int-21c
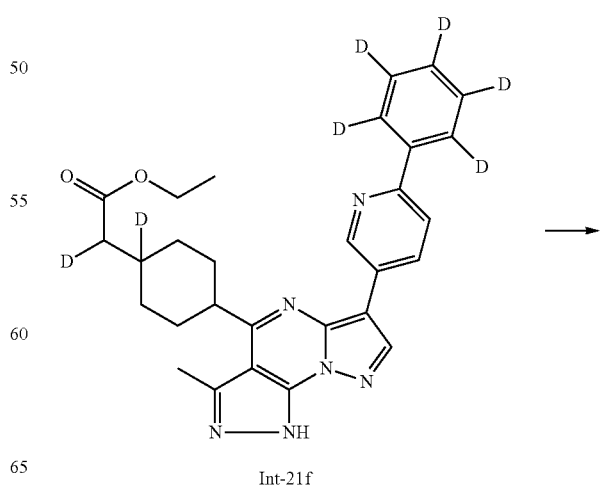
Int-21f -continued

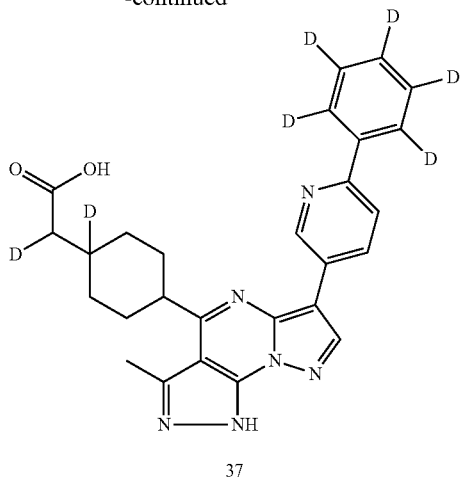

37

Synthesis of Deuterated Ethyl 2-(4-(7-(bis((2-(trimethylsilyl)ethoxy)methyl)amino)pyrazolo[1,5-a]pyrimidin-5-yl)cyclohexyl)acetate (Int-21a)

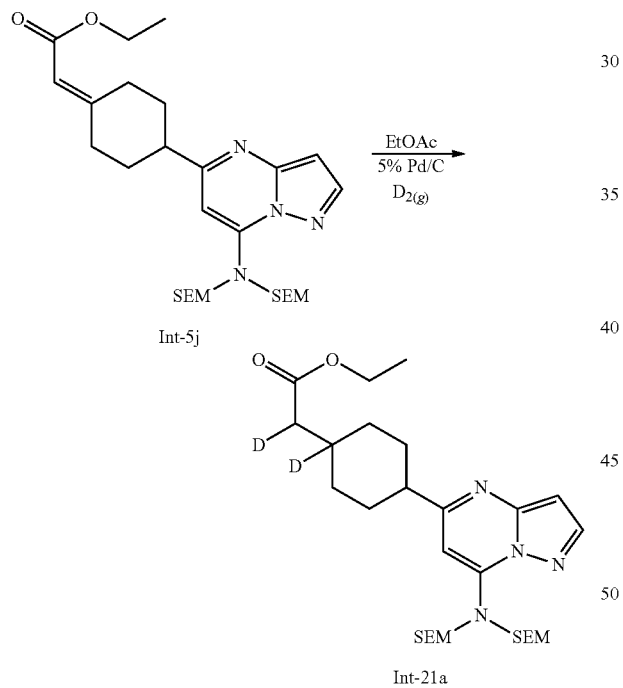

Ethyl 2-(4-(7-(bis((2-(trimethylsilyl)ethoxy)-methyl)amino)pyrazolo[1,5-a]pyrimidin-5-yl)cyclohexylidene)acetate (Int-5j) is prepared according to Steps A-I of Example 5. To a 50 mL round-bottom flask is charged Int-5j (800 mg, 1.43 mmol) and ethyl acetate (15 mL). The flask is flushed with argon, and 5% palladium on carbon (100 mg) is added. The flask is sealed and degassed under vacuum. Deuterium gas is then added via balloon. The reaction is stirred under a $D_2$ atmosphere 18 hours. The reaction is then filtered through celite to yield deuterated ethyl 2-(4-(7-(bis((2-(trimethylsilyl)ethoxy)methyl)amino)pyrazolo[1,5-a]pyrimidin-5-yl)cyclohexyl)acetate.

By essentially the same procedures described above in Steps J-P of Example 5, ethyl 2-(4-(7-amino-6,7-pyrazolo-3-(6-phenylpyridin-3-yl)pyrazolo[1,5-a]pyrimidin-5-yl)cyclohexyl)acetate (compound 37) can be prepared.

Example 22 mTOR Kinase Assay

The mTOR assay buffer contained 10 mM hepes (pH 7.4), 50 mM NaCl, 100 µg/ml BSA, 50 mM β-glycerophosphate, 10 mM $MnCl_2$ and 0.5 mM DTT. 20 ng of human mTOR enzyme was preincubated with the compound for 10 minutes. 5 µM ATP and 0.1 µM GST-S6K was added. The reaction was incubated for one hour at 30° C. Anti phospho p70-S6K (about 1.7 ng/well) and anti GST-XL665 (1:1 Ratio with the substrate GST-56K) were added after incubating. The plates were read at least 2 hours after adding the anti phospho p70-S6K and the anti GST-XL665.

$IC_{50}$ DETERMINATIONS: Dose-response curves were plotted from the inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

Compounds 1-35 were tested in the mTOR assay to determine their $IC_{50}$ values. Table 1 below lists compounds of the invention with activity data whereby the $IC_{50}$ values are rated "A", "B," or "C." The $IC_{50}$ values are rated "A" for $IC_{50}$ values less than 1 nM, "B" for $IC_{50}$ values in the range from 1 nM to 10 nM, and "C" for $IC_{50}$ values in the range from 10 nM to 100 nM. Compounds 1-35 have $IC_{50}$ values below 100 nM in the mTOR assay.

TABLE 1

| Compound No. | $IC_{50}$ |
|---|---|
| 1 | C |
| 2 | B |
| 3 | B |
| 4 | B |
| 5 | B |
| 6 | B |
| 7 | C |
| 8 | A |
| 9 | B |
| 10 | C |
| 11 | B |
| 12 | B |
| 13 | B |
| 14 | B |
| 15 | B |
| 16 | C |
| 17 | B |
| 18 | B |
| 19 | B |
| 20 | B |
| 21 | B |
| 22 | A |
| 23 | B |
| 24 | B |
| 25 | B |
| 26 | B |
| 27 | B |
| 28 | B |
| 29 | A |
| 30 | B |
| 31 | B |

TABLE 1-continued

| Compound No. | IC$_{50}$ |
| --- | --- |
| 32 | B |
| 33 | C |
| 34 | B |
| 35 | C |

Uses of the Fused Tricyclic Compounds

The Fused Tricyclic Compounds are useful in human and veterinary medicine in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, which is hereby incorporated by reference.

More specifically, the Fused Tricyclic Compounds can be useful in the treatment of a variety of cancers, including (but not limited to) the following: tumor of the bladder, breast (including BRCA-mutated breast cancer), colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;

leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma;

chronic lymphocytic leukemia ("CLL"), acute and chronic myelogenous leukemia, myelodysplastic syndrome and promyelocytic leukemia;

fibrosarcoma, rhabdomyosarcoma; head and neck, mantle cell lymphoma, myeloma;

astrocytoma, neuroblastoma, glioma, glioblastoma, malignant glial tumors, astrocytoma, hepatocellular carcinoma, gastrointestinal stromal tumors ("GIST") and schwannomas;

melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

While not being bound by any specific theory, due to the key role of kinases in the regulation of cellular proliferation in general, inhibitors of kinases could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The Fused Tricyclic Compounds may induce or inhibit apoptosis. The apoptotic response is aberrant in a variety of human diseases. The Fused Tricyclic Compounds, as modulators of apoptosis, will be useful in the treatment of cancer (including but not limited to those types mentioned hereinabove), viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

While not being bound by any specific theory, the Fused Tricyclic Compounds, as inhibitors of kinases, can modulate the level of cellular RNA and DNA synthesis. These compounds would therefore be useful in the treatment of viral infections (including but not limited to HIV, human papilloma virus, herpesvirus, poxvirus, Epstein-Barr virus, Sindbis virus and adenovirus).

In particular embodiments of the invention, Fused Tricyclic Compounds, as inhibitors of mTOR kinase could act in diseases or disorders other than cancer that are associated with dysregulated mTOR activity such as viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The Fused Tricyclic Compounds may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Fused Tricyclic Compounds may also be useful in inhibiting tumor angiogenesis and metastasis.

Another aspect of this invention is a method of treating a mammal (e.g., human) having a disease or condition associated with mTOR kinases by administering a therapeutically effective amount of at least one Fused Tricyclic Compound, or a pharmaceutically acceptable salt of said compound to the mammal.

In the therapies described above, a preferred dosage for administration to a patient is about 0.001 to 1000 mg/kg of body weight/day of the Fused Tricyclic Compound. An especially preferred dosage is about 0.01 to 25 mg/kg of body weight/day of the Fused Tricyclic Compound, or a pharmaceutically acceptable salt, of said compound.

Combination Therapies

The Fused Tricyclic Compounds may also be useful in combination (administered together or sequentially) with one or more of anti-cancer treatments such as radiation therapy, and/or one or more anti-cancer agents different from the Fused Tricyclic Compounds.

In one embodiment, the invention provides a method of treating cancer, comprising administering an amount (a dose) of a Fused Tricyclic Compound or a pharmaceutically acceptable salt thereof, and an amount (a dose) of one or more of additional anti-cancer drugs to a patient in need thereof.

In one embodiment, the Fused Tricyclic Compound and the additional anti-cancer agent(s) are administered in doses commonly employed when such agents are used as monotherapy for treating cancer.

The Fused Tricyclic Compound and the additional therapeutic agent(s) can act additively or synergistically. For instance, in one embodiment, the Fused Tricyclic Compound and the additional anti-cancer agent(s) are administered in doses lower than the doses commonly employed when such agents are used as monotherapy for treating cancer.

In another embodiment, the Fused Tricyclic Compound and the additional anti-cancer agent(s) act synergistically and are administered in doses lower than the doses commonly employed when such agents are used as monotherapy for treating cancer.

In one embodiment, the Fused Tricyclic Compound and the additional anti-cancer agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In other embodiments, the Fused Tricyclic Compounds may also be administered sequentially with known anticancer or cytotoxic agents when a combination formulation is inappropriate. The invention is not limited by the sequence of administration; the Fused Tricyclic Compounds may be administered either prior to or after administration of the known anticancer or cytotoxic agent. The order of administration for the sequence depends on the particular combinations chosen. For example, the cytotoxic activity of the cyclin-dependent kinase inhibitor flavopiridol is affected by the sequence of administration with anticancer agents. *Cancer Research*, (1997) 57, 3375. Selecting the appropriate administration sequence is well within the skill of medical practitioners, such as attending physicians.

Another aspect of the present invention is a method of treating one or more diseases associated with a mTOR protein kinase, e.g., cancer, comprising administering to a mammal in need of such treatment: an amount of a first compound, which is a compound of the present invention, or a pharmaceutically acceptable salt thereof; and an amount of at least one second compound, the second compound being an anticancer agent different from the compound of the present invention, wherein the amounts of the first compound and the second compound result in a therapeutic effect.

Non-limiting examples of suitable anti-cancer agents are selected from the group consisting of a Cytostatic agent, Cisplatin, Deforolimus (described in PCT publication No. 2003/064383), Doxorubicin, liposomal doxorubicin (e.g., Caelyx®, Myocet®, Doxil®, Taxotere, Taxol, Etoposide, Irinotecan, Camptostar, Topotecan, Paclitaxel, Docetaxel, Epothilones, Tamoxifen, 5-Fluorouracil, Methoxtrexate, Temozolomide, cyclophosphamide, SCH 66336, R115777®, L778,123®, BMS 214662®, Iressa®, Tarceva®, Antibodies to EGFR, antibodies to IGI-R (including, for example, those published in US 2005/0136063 published Jun. 23, 2005), ESK inhibitors, KSP inhibitors (such as, for example, those published in WO 2006/098962 and WO 2006/098961; ispinesib, SB-743921 from Cytokinetics), Centrosome associated protein E ("CENP-E") inhibitors (e.g., GSK-923295), Gleevec®, Intron, Ara-C, Adriamycin, Cytoxan, Gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Oxaliplatin, Leucovirin, ELOXATIN™, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, bortezomib ("Velcade"), Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225®, Satriplatin, mylotarg, Avastin, Rituxan, Panitubimab, Sutent, Sorafinib, Sprycel (dastinib), Nilotinib, Tykerb (Lapatinib) and Campath.

In one embodiment, the invention provides a method of treating cancer, the method comprising administering an amount of a Fused Tricyclic Compound or a pharmaceutically acceptable salt thereof, and an amount of one or more additional anticancer drugs to a patient in need thereof. In certain embodiments, the one or more additional anticancer drugs are selected from the group consisting of Adriamycin, Altretamine, Amidox, Aminoglutethimide, Amsacrine, Anastrazole, Antibodies to EGFR, 3-AP, Aphidicolon, Ara-C, Arsenic trioxide, L-Asparaginase, Bevacizumab, Bleomycin, BMS 214662, Bortezomib, Busulfan, Campath, Camptostar, Capecitabine, Carboplatin, Carmustine, Centrosome associated protein E ("CENP-E") inhibitors, Cetuximab, Cladribine, Chlorambucil, Chlormethine, Chlorotrianisene, Cisplatin, Clofarabine, cyclophosphamide, Cytarabine, a Cytostatic agent, Cytoxan, Dacarbazine, Dactinomycin, Daunorubicin, Dasatinib, Deforolimus, Deoxycoformycin, Didox, Diethylstilbestrol, Docetaxel, Doxorubicin, Dromostanolone, Droloxafine, Epirubicin, Epothilones, ERK inhibitors, Erlotinib, Etoposide, 17α-Ethinylestradiol, Estramustine, Exemestane, Floxuridine, Fludarabine, Fludarabine phosphate, 5-Fluorouracil, Fluoxymesterone, Flutamide, Fulvestrant, Gefitinib, Gemcitabine, Gemtuzumab ozogamicin, Goserelin, GSK-923295, Hexamethylmelamine, Hydroxyprogesterone, Hydroxyurea, Ibritumomab Tiuxetan, Idarubicin, Ifosfamide, Imatinib mesylate, Intron, Irinotecan, ispinesib, KSP inhibitors, L778,123, Lapatinib, Leucovirin, Leuprolide, Lerozole, Letrazole, Levamisole, Liposomal Doxorubicin, Liposomal, Lomustine, Lonafarnib, Medroxyprogesteroneacetate, Megestrolacetate, Melphalan, 6-Mercaptopurine, Methoxtrexate, Methylprednisolone, Methyltestosterone, Mithramycin, Mitomycin-C, Mitotane, Mitoxantrone, Navelbene, Nilotinib, Oxaliplatin, Paclitaxel, Panitubimab, Pentostatin, Pipobroman, Porfimer, Prednisolone, Prednisone propionate, Procarbazine, Reloxafine, Rituximab, Satriplatin, SB-743921, Sm11, Sorafinib, Streptozocin, Sunitinib, Tamoxifen, Taxotere, Taxol, Temozolomide, Teniposide, Testolactone, Testosterone, Tezacitabine, 6-Thioguanine, Thiotepa, Tipifarnib, Topotecan, Toremifene, Tositumomab, Trastuzumab, Triamcinolone, Triapine, Triethylenemelamine, Triethylenethiophosphoramine, Trimidox, Uracil mustard, Vinblastine, Vincristine, Vindesine, and Vinorelbine.

In one embodiment, the invention provides a method of treating cancer, the method comprising administering an amount of a Fused Tricylic Compound or a pharmaceutically acceptable salt thereof, and an amount of one or more of a MAP Kinase pathway inhibitor such as bRaf, MEK, or ERK inhibitors to a patient in need thereof.

In another embodiment, the invention provides a method of treating cancer, the method comprising administering an amount of a Fused Tricylic Compound or a pharmaceutically acceptable salt thereof, and an amount of one or more of ERK inhibitors to a patient in need thereof.

ERK inhibitors (i.e., ERK1 inhibitors and/or ERK2 inhibitors) useful in the method include but are not limited to the compounds are described in PCT publication No. WO 2007/070398, PCT publication No. WO2009/105500 (particularly, those disclosed at pages 91-104), PCT publication No. WO 2008/156739, U.S. publication No. 2007/0232610, and U.S. Publication No. 2009/0118264, all of which are hereby incorporated by reference.

Compositions and Administration

This invention is also directed to pharmaceutical compositions which comprise at least one Fused Tricyclic Compound, or a pharmaceutically acceptable salt of said compound and at least one pharmaceutically acceptable carrier.

When administered to a patient, the Fused Tricyclic Compounds can be administered as a component of a composition that comprises a pharmaceutically acceptable carrier or vehicle. The present invention provides pharmaceutical compositions comprising an effective amount of at least one Fused Tricyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semisolid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Fused Tricyclic Compounds of the present invention may also be delivered transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anticancer activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Fused Tricyclic Compound is administered orally.

In another embodiment, the Fused Tricyclic Compound is administered intravenously.

In another embodiment, the Fused Tricyclic Compound is administered topically.

In still another embodiment, the Fused Tricyclic Compounds is administered sublingually.

In one embodiment, a pharmaceutical preparation comprising at least one Fused Tricyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Compound(s) by weight or volume. In various embodiments, the present compositions can contain, in one embodiment, from about 1% to about 70% or from about 5% to about 60% of the Fused Tricyclic Compound(s) by weight or volume.

The quantity of Fused Tricyclic Compound in a unit dose of preparation may be varied or adjusted from about 1 mg to about 2500 mg. In various embodiments, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

For administration to human patients, the amount and frequency of administration of the Fused Tricyclic Compounds will be regulated according to the judgment of the attending clinician considering such factors as age, condition and size of the patient as well as severity of the symptoms being treated. Generally, a total daily dosage of the Fused Tricyclic Compounds range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Fused Tricyclic Compound or a pharmaceutically acceptable salt thereof; (ii) one or more additional therapeutic agents that are not a Fused Tricyclic Compound; and (iii) a pharmaceutically acceptable carrier, wherein the amounts in the composition are together effective to treat disease or disorder associated with dysregulated mTOR activity, such as a cancer.

Kits

Another aspect of this invention is a kit comprising a therapeutically effective amount of at least one Fused Tricylic Compound, or a pharmaceutically acceptable salt of said compound and a pharmaceutically acceptable carrier, vehicle or diluent.

Yet another aspect of this invention is a kit comprising an amount of at least one Fused Tricylic Compound, or a pharmaceutically acceptable salt of said compound and an amount of at least one anti-cancer agent listed above, wherein the amounts of the two or more active ingredients result in a desired therapeutic effect. In one embodiment, the at least one Fused Tricyclic Compounds and the at least one anti-cancer agent are provided in the same container. In one embodiment, the at least one Fused Tricyclic Compounds and the at least one additional anti-cancer agent are provided in separate containers.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound having the formula (I):

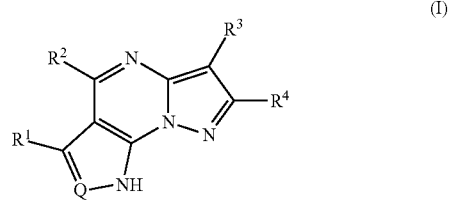

or a pharmaceutically acceptable salt thereof, wherein

Q is N or C(H);

$R^1$ is H, halo, —$NR^5R^6$, —$OR^7$, —$SR^8$, —CN, alkyl, alkenyl, alkynyl, haloalkyl, cycloalkyl, aryl, heteroaryl, heterocyclyl, cycloalkylalkyl, arylalkyl, heteroarylalkyl, or heterocyclylalkyl, wherein said cycloalkyl, aryl, heteroaryl, heterocyclyl, cycloalkylalkyl, arylalkyl, heteroarylalkyl, or heterocyclylalkyl of $R^1$ is unsubstituted or substituted with one more moieties, which can be the same or different, each moiety being selected from the group consisting of halogen, alkyl, cycloalkyl, —$CF_3$, —CN, —C(O)OH, —$(CH_2)_x$—C(O)OH, —$OCF_3$, —$OR^7$, —$C(O)R^{10}$, —$NR^5R^6$, —$C(O_2)$-alkyl, —C(O)$NR^5R^6$, —$SR^8$, and —$S(O_2)R^7$;

$R^2$ is selected from the group consisting of heterocyclyl, spiroheterocyclyl, heterocyclenyl, cycloalkyl, cycloalkenyl, heteroaryl, aryl, heterocyclylalkyl, spiroheterocyclylalkyl, heterocyclenylalkyl, cycloalkylalkyl, cycloalkenylalkyl, heteroarylalkyl, arylalkyl, —O-heterocyclyl, —S-heterocyclyl, —S(O)-heterocyclyl, —$S(O)_2$-heterocyclyl, —$N(R^9)$-heterocyclyl, and -alkyl-$N(R^9)$-heterocyclyl, wherein said heterocyclyl, spiroheterocyclyl, heterocyclenyl, cycloalkyl, cycloalkenyl, heteroaryl, aryl, heterocyclylalkyl, spiroheterocyclylalkyl, heterocyclenylalkyl, cycloalkylalkyl, cycloalkenylalkyl, heteroarylalkyl, arylalkyl, —O-heterocyclyl, —S-heterocyclyl, —S(O)-heterocyclyl, —$S(O)_2$-heterocyclyl, —$N(R^9)$-heterocyclyl, or-alkyl—$N(R^9)$-heterocyclyl is unsubstituted or substituted with one to four moieties, which can be the same or different, each moiety being selected from group X;

X is alkyl, halo, —CN, —$NR^5R^6$, $SR^8$, —$OR^7$, —C(O) alkyl, -trihaloalkyl, -dihaloalkyl, -monohaloalkyl, —$C(O)_2$alkyl, —$C(O)_2H$, hydroxyalkyl, —$S(O)_2R^8$, hydroxyl, -alkyl—$C(O)_2H$, -alkyl(CO)N($CH_3$)—O—$CH_3$, —$C(O)_2$-alkyl, -alkyl—C(O)—$NH_2$, -alkyl-CN, —C(O)—$NR^5R^6$, -alkyl-$C(O)_2$alkyl, —C(O)-hydroxyalkyl, —C(O)-alkyl-O-alkyl, -alkyl(CO)N(H)—$S(O)_2$-cycloalkyl, -alkyl(CO)N(H)—$S(O)_2$—$CF_3$, -alkyl(CO)N(H)—$S(O)_2$-alkyl, -alkyl-C(O)—N(alkyl)$_2$, -alkyl-N(H)—$S(O)_2$-alkyl, -alkyl(CO)N(H)—$S(O)_2$-cycloalkyl, —C(O)—$CO_2H$, —C(O)—CH(OH)—$CH_3$, —C(O)CH(OH)$CH_2OH$, —$C(O)_2$-alkyl-aryl, —$SO_2$—$CF_3$, or —C(O)H, or X is cycloalkyl, heterocyclyl, aryl, heteroaryl, heteroarylalkyl, —NH-heterocyclyl, —C(O)-heteroaryl, wherein each of said cycloalkyl, heterocyclyl, aryl, heteroaryl, heteroarylalkyl, —NH-heterocyclyl, —C(O)-heteroaryl of X is unsubstituted or substituted with one or more moieties, which can be the same or different, each moiety being selected from the group consisting of halogen, alkyl, cycloalkyl, —CF₃,
—CN, —C(O)OH, —SO₃H, —P(O)(OH)₂, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷;

R³ is H, halogen, alkenyl, alkynyl, —CF₃, —C(O)R¹⁰, aryl, cycloalkyl, cycloalkenyl, heteroaryl, heterocyclyl, heterocycloalkenyl, arylalkyl, cycloalkylalkyl, cycloalkenylalkyl, heteroarylalkyl, heterocyclylalkyl, heterocycloalkenylalkyl, wherein each of said aryl, cycloalkyl, cycloalkenyl, heteroaryl, heterocyclyl, heterocycloalkenyl, arylalkyl, cycloalkylalkyl, cycloalkenylalkyl, heteroarylalkyl, heterocyclylalkyl, heterocycloalkenylalkyl of R³ is unsubstituted or substituted with one or more moieties which can be the same or different, each moiety being selected from the group consisting of Y, halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷;

Y is aryl, cycloalkyl, cycloalkenyl, heteroaryl, heterocyclyl, or heterocycloalkenyl, wherein each of said cycloalkyl, cycloalkenyl, heteroaryl, heterocyclyl, or heterocycloalkenyl of Y is unsubstituted or substituted with one more moieties, which can be the same or different, each moiety being selected from the group consisting of halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷;

R⁴ is H, halo, —NR⁵R⁶, —OR⁷, —OR⁸, —SR⁹, —CN, alkyl, alkenyl, alkynyl, haloalkyl, cycloalkyl, aryl, heteroaryl, heterocyclyl, cycloalkylalkyl, arylalkyl, heteroarylalkyl, or heterocyclylalkyl;

each occurrence of R⁵ is independently H, alkyl, cycloalkyl, aryl, heteroaryl, or heterocyclyl;

each occurrence of R⁶ is independently H, alkyl, cycloalkyl, aryl, heteroaryl, or heterocyclyl, or R⁵ and R⁶ together with the nitrogen atom to which they are attached form a heterocyclyl ring;

each occurrence of R⁷ is independently H, alkyl, cycloalkyl, aryl, heteroaryl, or heterocyclyl;

each occurrence of R⁸ is independently H, alkyl, cycloalkyl, aryl, heteroaryl, or heterocyclyl;

each occurrence of R⁹ is independently H or alkyl;

R¹⁰ is alkyl, cycloalkyl, or aryl; and x is an integer from 1 to 4.

2. The compound of claim 1 or a pharmaceutically acceptable salt thereof, wherein R³ is aryl or heteroaryl, wherein said aryl or heteroaryl of R³ is unsubstituted or substituted with one or more moieties which can be the same or different, each moiety being selected from the group consisting of Y, halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)- alkyl, —C(O)NR⁵R⁶, —SR⁸, and —S(O₂)R⁷.

3. The compound of claim 2 or a pharmaceutically acceptable salt thereof, wherein said aryl or heteroaryl of R³ is substituted with one Y group.

4. The compound of claim 3 or a pharmaceutically acceptable salt thereof, wherein said Y group is aryl or heteroaryl, wherein said aryl or heteroaryl of Y is unsubstituted or substituted with one more moieties, which can be the same or different, each moiety being selected from the group consisting of halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷.

5. The compound of claim 1 or a pharmaceutically acceptable salt thereof, wherein R³ is pyridyl, quinolinyl, or pyrazolyl, wherein said pyridyl, quinolinyl, or pyrazolyl is unsubstituted or substituted with one or more moieties which can be the same or different, each moiety being selected from the group consisting of Y, halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷.

6. The compound of claim 1 or a pharmaceutically acceptable salt thereof, wherein R² is heterocyclyl, cycloalkyl, cycloalkenyl, heterocyclylalkyl, cycloalkylalkyl, —O-heterocyclyl, or -alkyl-N(H)-heterocyclyl, wherein said heterocyclyl, heterocyclylalkyl, —O-heterocyclyl, or -alkyl-N(H)-heterocyclyl of R² is unsubstituted or substituted with one to four moieties, which can be the same or different, each moiety being selected from the group consisting of alkyl, —C(O)₂H, —S(O)₂CH₃, —CH₂C(O)₂H, —C(O)—CH(OH)—CH₃, and —C(O)—CH(OH)—CH₂OH.

7. The compound of claim 1 or a pharmaceutically acceptable salt thereof, wherein R¹ is H or alkyl.

8. The compound of claim 1 or a pharmaceutically acceptable salt thereof, wherein R⁴ is H.

9. The compound of claim 1 having the formula (Ia)

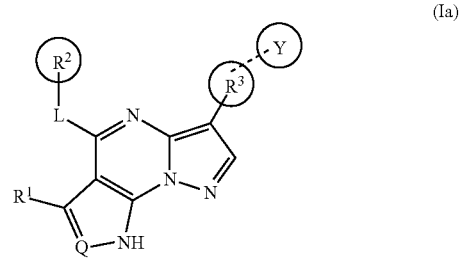

(Ia)

or a pharmaceutically acceptable salt thereof, wherein

Q is N or C(H);

L is —CH₂—, —CH₂—CH₂—, —CH₂—CH₂—CH₂—, —CH₂—CH₂—CH₂—CH₂—, —NH—CH₂—, or —O—, or L is absent such that R² is bonded directly to the illustrated pyrimidine ring;

R¹ is H, halo, or alkyl;

R² is heterocyclyl, heterocyclenyl, cycloalkyl, or cycloalkenyl, wherein said heterocyclyl, heterocyclenyl, cycloalkyl, or cycloalkenyl of R² is unsubstituted or substituted with one to four moieties, which can be the same or different, each moiety being selected from the group X;

X is alkyl, halo, —CN, —NR⁵R⁶, SR⁸, —OR⁷, —C(O) alkyl, -trihaloalkyl, -dihaloalkyl, -monohaloalkyl, —C(O)₂alkyl, —C(O)₂H, hydroxyalkyl, —S(O)₂R⁸, -alkyl-C(O)₂H, —C(O)—CH(OH)—CH₃, or —C(O)—CH(OH)—CH₂OH;

R³ is aryl, cycloalkyl, cycloalkenyl, heteroaryl, heterocyclyl, heterocycloalkenyl, wherein each of said aryl, cycloalkyl, cycloalkenyl, heteroaryl, heterocyclyl, or heterocycloalkenyl of R³ is unsubstituted or substituted with one or more moieties which can be the same or different, each moiety being selected from the group consisting of halogen, alkyl, cycloalkyl, CF₃, CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, —S(O₂)R⁷; and Y is present or absent, wherein Y, if present, is aryl or heteroaryl, wherein said aryl or heteroaryl of Y is unsubstituted or substituted with one more moieties, which can be the same or different, each moiety being selected from the group consisting of halogen, alkyl, cycloalkyl, —CF₃, CN, —C(O)OH, —(CH₂)ₓ—C(O)OH, —OCF₃, —OR⁷, —C(O)R¹⁹, —NR⁵R⁶, —C(O₂)-alkyl, —C(O)NR⁵R⁶, —SR⁸, and —S(O₂)R⁷, each occurrence of R⁵ is independently H, alkyl, cycloalkyl, aryl, heteroaryl, or heterocyclyl;

each occurrence of R⁶ is independently H, alkyl, cycloalkyl, aryl, heteroaryl, or heterocyclyl, or R⁵ and R⁶ together with the nitrogen atom to which they are attached form a heterocyclyl ring;

each occurrence of R⁷ is independently H, alkyl, cycloalkyl, aryl, heteroaryl, or heterocyclyl;

each occurrence of R⁸ is independently H, alkyl, cycloalkyl, aryl, heteroaryl, or heterocyclyl;

each occurrence of R⁹ is independently H or alkyl;

R¹⁹ is alkyl, cycloalkyl, or aryl; and x is an integer from 1 to 4.

10. The compound of claim 9 or a pharmaceutically acceptable salt thereof, wherein R² is heterocyclyl, cycloalkyl, or cycloalkenyl, wherein said heterocyclyl, cycloalkyl, or cycloalkenyl of R² is unsubstituted or substituted with one to four moieties, which can be the same or different, each moiety being alkyl, —C(O)₂H, —S(O)₂CH₃, —CH₂C(O)₂H, —C(O)—CH(OH)—CH₃, or —C(O)—CH(OH)—CH₂OH.

11. The compound of claim 9 or a pharmaceutically acceptable salt thereof, wherein R³ is pyridyl, quinolinyl, or pyrazolyl, wherein said pyridyl, quinolinyl, or pyrazolyl is unsubstituted or substituted with one or more moieties which can be the same or different, each moiety being selected from the group consisting of Y, halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷.

12. The compound of claim 10 or a pharmaceutically acceptable salt thereof, wherein said R³ is pyridyl, quinolinyl, or pyrazolyl wherein said pyridyl, quinolinyl, or pyrazolyl is unsubstituted or substituted with one or more moieties which can be the same or different, each moiety being selected from the group consisting of Y, halogen, alkyl, cycloalkyl, —CF₃, —CN, —C(O)OH, —(CH₂)ₓ—C(O)OH, —OCF₃, —OR⁷, —C(O)R¹⁰, —NR⁵R⁶, —C(O₂)-alkyl, —C(O)NR⁵R⁶, —SR⁸, and —S(O₂)R⁷.

13. A compound having one of the following formulas, or a pharmaceutically acceptable salt thereof:

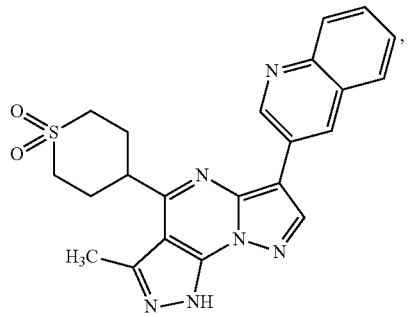

-continued

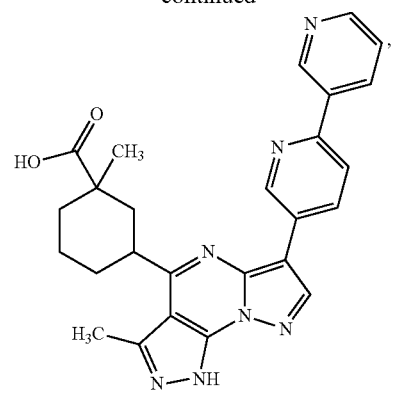

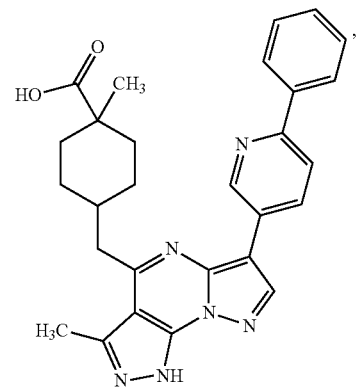

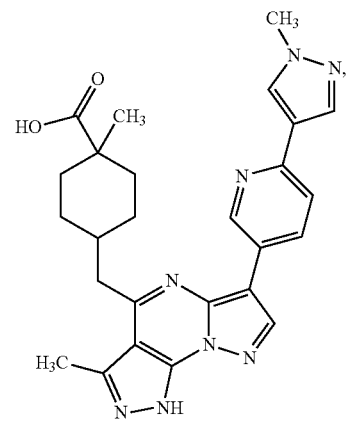

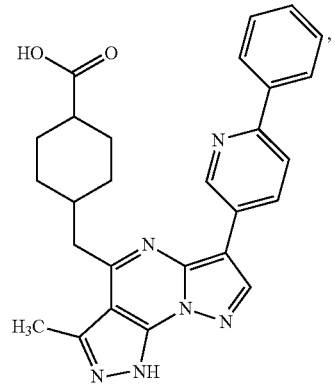

155
-continued
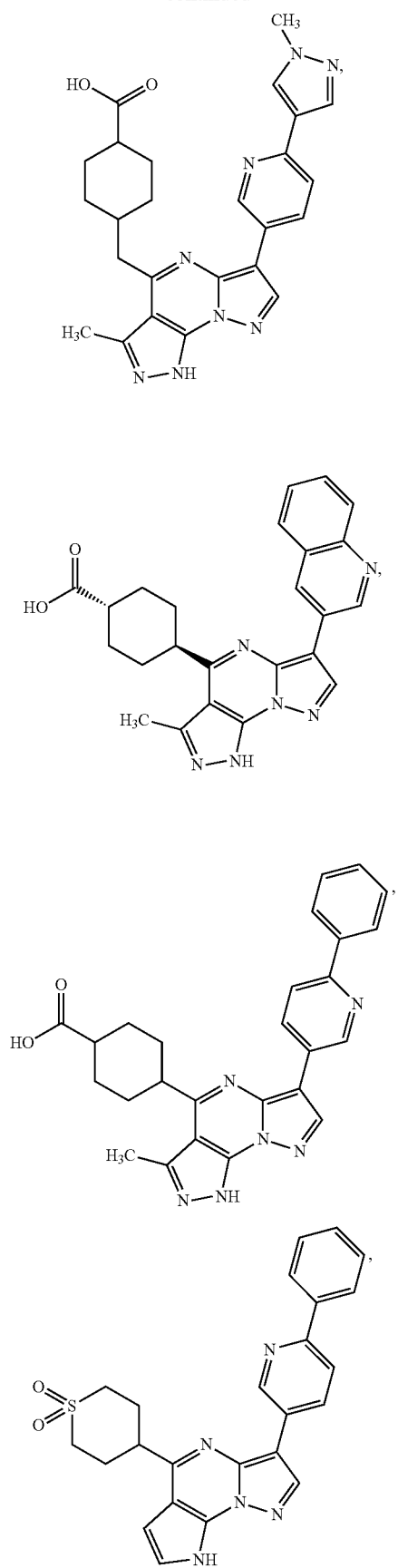
156
-continued
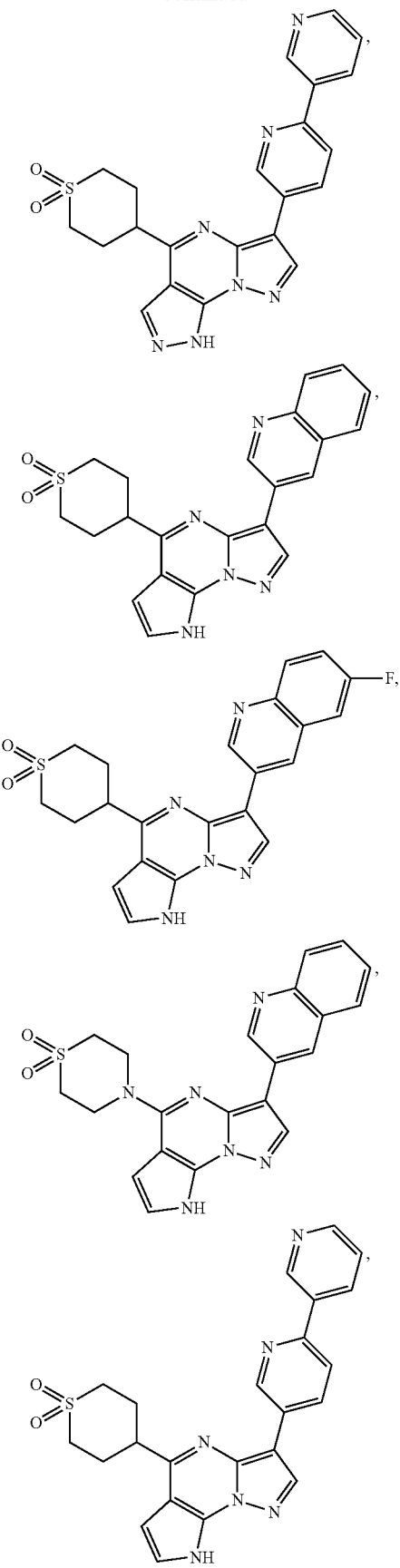

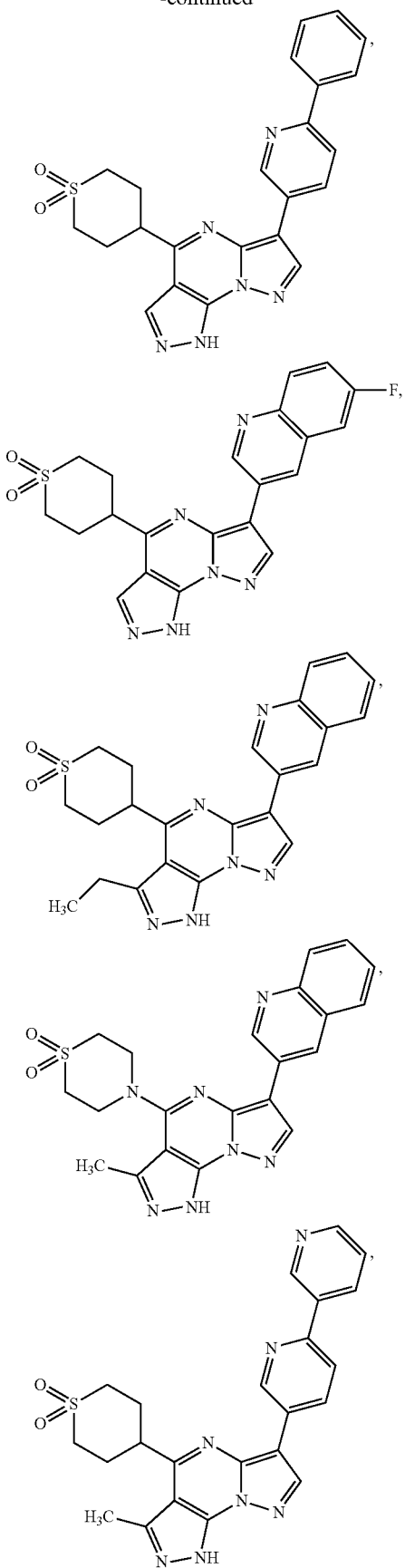
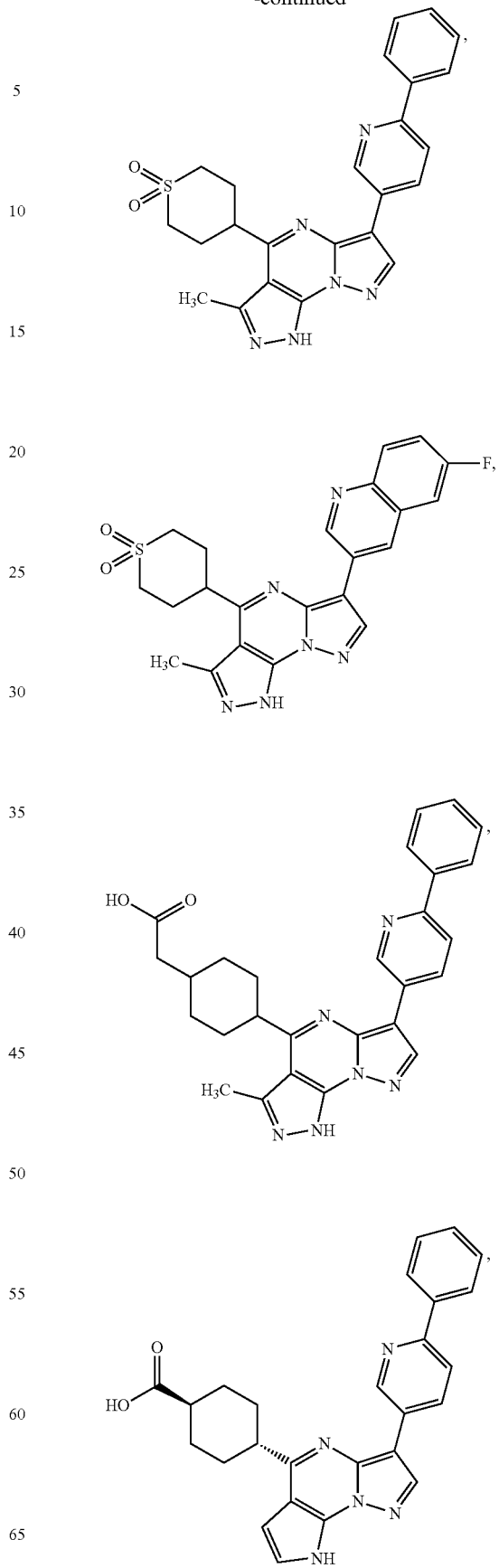

-continued
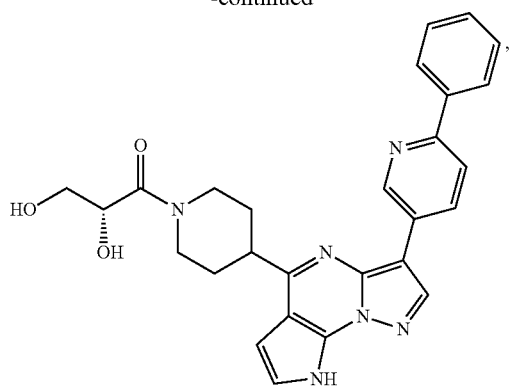
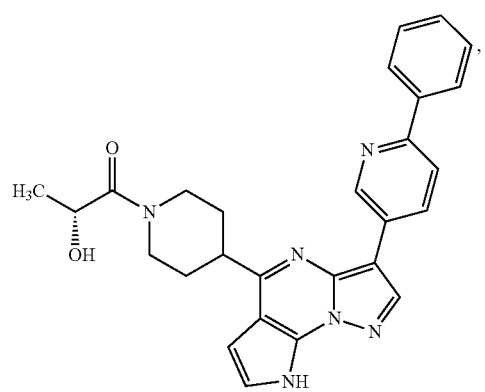
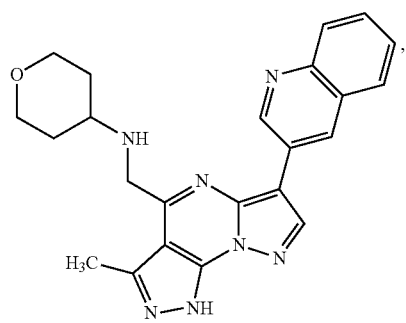
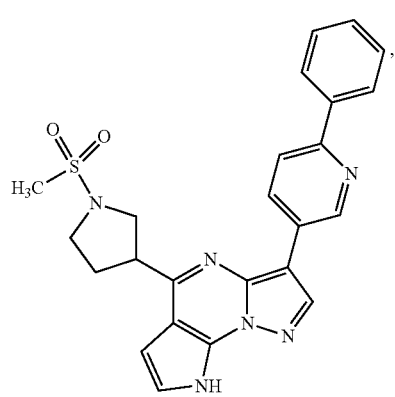
-continued
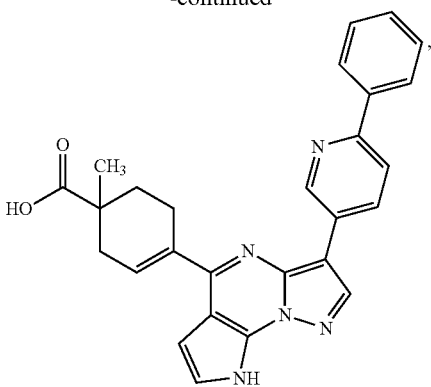
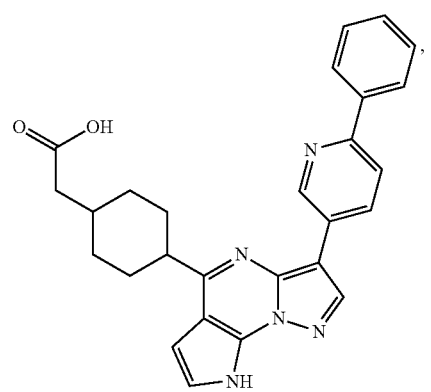
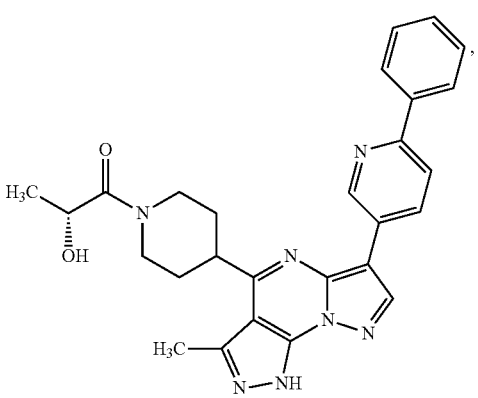
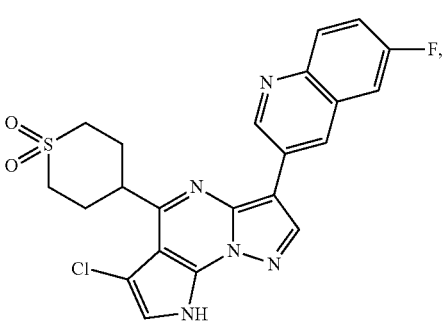

161
-continued
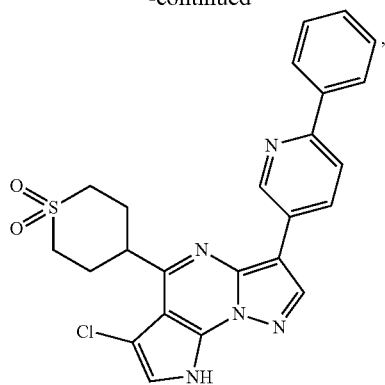
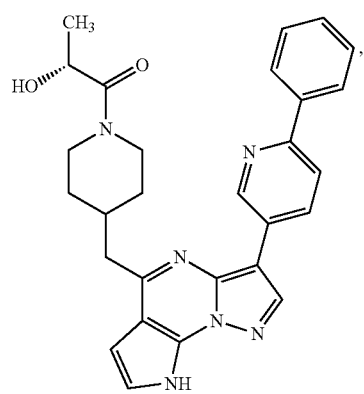
162
-continued
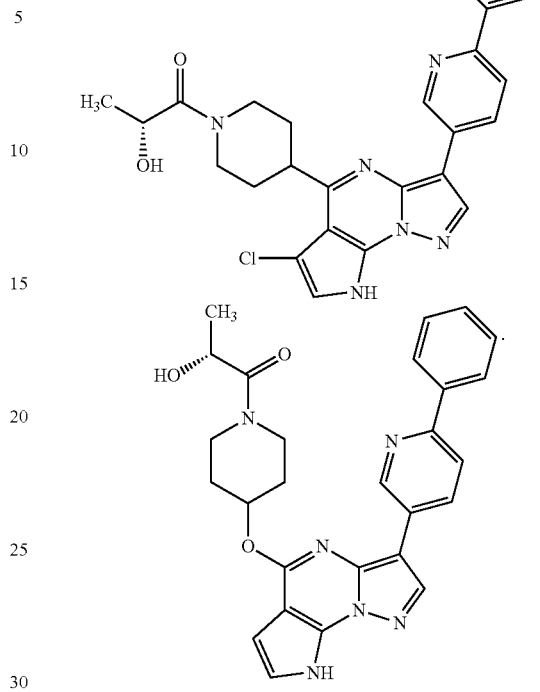
14. A pharmaceutical composition comprising the compound of claim 1, or a pharmaceutically acceptable salt thereof, and at least one pharmaceutically acceptable carrier.
* * * * *